(12) United States Patent
McEwen et al.

(10) Patent No.: US 12,385,038 B2
(45) Date of Patent: Aug. 12, 2025

(54) SYSTEMS AND METHODS FOR IDENTIFICATION OF OPTIMIZED PROTEIN PRODUCTION AND KITS THEREFOR

(71) Applicant: BRUKER CELLULAR ANALYSIS, INC., Emeryville, CA (US)

(72) Inventors: Jason M. McEwen, El Cerrito, CA (US); Troy A. Lionberger, Berkeley, CA (US); Eric K. Sackmann, Emeryville, CA (US); Volker L. S. Kurz, Emeryville, CA (US); Kellen C. Mobilia, Emeryville, CA (US)

(73) Assignee: Bruker Cellular Analysis, Inc., Emeryville, CA (US)

( * ) Notice: Subject to any disclaimer, the term of this patent is extended or adjusted under 35 U.S.C. 154(b) by 1161 days.

(21) Appl. No.: 17/226,914

(22) Filed: Apr. 9, 2021

(65) Prior Publication Data

US 2021/0292751 A1 Sep. 23, 2021

Related U.S. Application Data

(63) Continuation of application No. PCT/US2019/055953, filed on Oct. 11, 2019.

(60) Provisional application No. 62/744,578, filed on Oct. 11, 2018.

(51) Int. Cl.
*C12N 15/10* (2006.01)
*B01L 3/00* (2006.01)

(52) U.S. Cl.
CPC .... *C12N 15/1075* (2013.01); *B01L 3/502761* (2013.01); *C12N 15/1065* (2013.01); *B01L 2200/0647* (2013.01)

(58) Field of Classification Search
None
See application file for complete search history.

(56) References Cited

U.S. PATENT DOCUMENTS

| | | |
|---|---|---|
| 6,294,063 B1 | 9/2001 | Becker et al. |
| 6,942,776 B2 | 9/2005 | Medoro |
| 7,090,759 B1 | 8/2006 | Seul |
| 7,442,339 B2 | 10/2008 | Sundararajan et al. |
| 7,699,969 B2 | 4/2010 | Manaresi et al. |
| 7,956,339 B2 | 6/2011 | Ohta et al. |
| 8,581,167 B2 | 11/2013 | Lean et al. |
| 9,144,806 B2 | 9/2015 | Chen et al. |
| 9,403,172 B2 | 8/2016 | Short et al. |
| 10,723,988 B2 | 7/2020 | Lowe et al. |
| 11,007,520 B2 | 5/2021 | Lowe et al. |
| 2003/0008364 A1 | 1/2003 | Wang et al. |
| 2003/0175947 A1 | 9/2003 | Liu et al. |
| 2004/0072278 A1 | 4/2004 | Chou et al. |
| 2004/0191789 A1 | 9/2004 | Manaresi et al. |
| 2004/0197905 A1 | 10/2004 | Hafeman |
| 2005/0112548 A1 | 5/2005 | Segawa et al. |
| 2005/0129581 A1 | 6/2005 | McBride et al. |
| 2005/0175981 A1 | 8/2005 | Voldman et al. |
| 2005/0274456 A1 | 12/2005 | Roitman et al. |
| 2006/0091015 A1 | 5/2006 | Lau |
| 2006/0154361 A1 | 7/2006 | Wikswo et al. |
| 2006/0263612 A1 | 11/2006 | Chen et al. |
| 2007/0095669 A1 | 5/2007 | Lau et al. |
| 2007/0183934 A1 | 8/2007 | Diercks et al. |
| 2007/0242105 A1 | 10/2007 | Srinivasan et al. |
| 2008/0223721 A1 | 9/2008 | Cohen et al. |
| 2008/0302732 A1 | 12/2008 | Soh et al. |
| 2009/0023608 A1 | 1/2009 | Hung et al. |
| 2009/0098541 A1 | 4/2009 | Southern et al. |
| 2009/0170186 A1 | 7/2009 | Wu et al. |
| 2010/0003666 A1 | 1/2010 | Lee et al. |
| 2010/0021910 A1 | 1/2010 | Cao et al. |
| 2010/0068706 A1 | 3/2010 | Pourahmadi et al. |
| 2010/0273681 A1 | 10/2010 | Cerrina et al. |
| 2011/0053151 A1 | 3/2011 | Hansen et al. |
| 2011/0117634 A1 | 5/2011 | Halamish et al. |

(Continued)

FOREIGN PATENT DOCUMENTS

| | | |
|---|---|---|
| CN | 101275114 A | 10/2008 |
| CN | 108495712 A | 9/2018 |

(Continued)

OTHER PUBLICATIONS

Agresti et al.; Ultrahigh-Throughput Screening in Drop-Based Microfluidics for Directed Evolution; Proceedings of the National Academy of Sciences, 107(9); pp. 4004-4009; Mar. 2, 2010.

Beaumont et al.; Mulitparameter Cell Characterization Using Nanofluidic Technology Facilities Real-Time Phenotypic and Genotypic Elucidation of Intratumor-Heterogeneity; bioRxiv, pp. 1-33; Oct. 31, 2018.

Chiou et al.; Massively Parallel Manipulation of Single Cells and Microparticles Using Optical Images; Nature; (436) pp. 370-372; Jul. 2005.

Chiou: Massively parallel optical manipulation of single cells, mirco- and nano-particles on optoelectronic devices; University of California at Berkeley; 147 pages (Dissertation); (year of pub. sufficiently earlier than effective US filing date and any foreign priority date) Fall 2005.

(Continued)

*Primary Examiner* — Kaijiang Zhang
(74) *Attorney, Agent, or Firm* — Shay Glenn LLP

(57) ABSTRACT

Systems, methods, and kits therefor, enabling rapid protein evolution are described herein. A system useful in the methods described herein include a DNA synthesis component; a microfluidic system including a microfluidic device having a microfluidic channel and sequestration pens; and a computing component, which is configured to analyze assay results and, based upon the analysis, design improved DNA sequences for iterative protein evolution. The microfluidic system is configured to permit correlation of DNA sequence on a bead to its location within the microfluidic device, permit cell free protein expression of a DNA sequence captured to a bead, and to permit assay of the protein so produced.

22 Claims, 15 Drawing Sheets

(56) References Cited

U.S. PATENT DOCUMENTS

| | | | |
|---|---|---|---|
| 2011/0143964 | A1 | 6/2011 | Zhou et al. |
| 2011/0262906 | A1 | 10/2011 | Dimov et al. |
| 2012/0009671 | A1 | 1/2012 | Hansen et al. |
| 2012/0015347 | A1 | 1/2012 | Singhal et al. |
| 2012/0015382 | A1 | 1/2012 | Weitz et al. |
| 2012/0118740 | A1 | 5/2012 | Garcia et al. |
| 2012/0156675 | A1 | 6/2012 | Lueerssen et al. |
| 2012/0208266 | A1 | 8/2012 | Bookbinder et al. |
| 2012/0325665 | A1 | 12/2012 | Chiou et al. |
| 2013/0115606 | A1 | 5/2013 | Hansen et al. |
| 2013/0118905 | A1 | 5/2013 | Morimoto et al. |
| 2013/0130232 | A1 | 5/2013 | Weibel et al. |
| 2013/0146459 | A1 | 6/2013 | Bazant et al. |
| 2013/0171628 | A1 | 7/2013 | Di Carlo et al. |
| 2013/0190212 | A1 | 7/2013 | Handique et al. |
| 2013/0204076 | A1 | 8/2013 | Han et al. |
| 2013/0261021 | A1 | 10/2013 | Bocchi et al. |
| 2014/0116881 | A1 | 5/2014 | Chapman et al. |
| 2014/0154703 | A1 | 6/2014 | Skelley et al. |
| 2014/0154791 | A1 | 6/2014 | North et al. |
| 2015/0018226 | A1 | 1/2015 | Hansen et al. |
| 2015/0148264 | A1 | 5/2015 | Esfandyapour et al. |
| 2015/0151298 | A1 | 6/2015 | White et al. |
| 2015/0151307 | A1 | 6/2015 | Breinlinger et al. |
| 2015/0165436 | A1 | 6/2015 | Chapman et al. |
| 2015/0166326 | A1 | 6/2015 | Chapman et al. |
| 2015/0167043 | A1 | 6/2015 | Goluch et al. |
| 2016/0171686 | A1 | 6/2016 | Du et al. |
| 2016/0184821 | A1 | 6/2016 | Hobbs et al. |
| 2016/0199837 | A1 | 7/2016 | Breinlinger et al. |
| 2016/0252495 | A1 | 9/2016 | Ricicova et al. |
| 2017/0021366 | A1 | 1/2017 | Chapman et al. |
| 2017/0165667 | A1 | 6/2017 | Beaumont et al. |
| 2017/0276679 | A1 | 9/2017 | Chapman et al. |
| 2018/0068055 | A1* | 3/2018 | Ofran et al. ............ G16B 15/00 |
| 2018/0272294 | A1* | 9/2018 | Griffiths et al. .. B01L 3/502746 |
| 2018/0298318 | A1 | 10/2018 | Kurz et al. |
| 2019/0085375 | A1 | 3/2019 | McEwen |
| 2019/0240665 | A1 | 8/2019 | Lionberger et al. |
| 2019/0345488 | A1 | 11/2019 | Soumillon et al. |
| 2020/0064337 | A1 | 2/2020 | Park et al. |
| 2020/0171501 | A1 | 6/2020 | McEwen et al. |
| 2020/0392567 | A1 | 12/2020 | Bennett et al. |
| 2021/0115436 | A1 | 4/2021 | Ramenani et al. |

FOREIGN PATENT DOCUMENTS

| | | | | |
|---|---|---|---|---|
| JP | 2001184381 | A | | 7/2001 |
| JP | 2005519384 | A | | 6/2005 |
| JP | 2008515421 | A | | 5/2008 |
| JP | 2012034641 | A | | 2/2012 |
| JP | 2015529094 | A | | 10/2015 |
| JP | 2016504924 | A | | 2/2016 |
| JP | 2016537699 | A | | 12/2016 |
| JP | 2017534601 | A | | 11/2017 |
| KR | 20100008222 | A | | 1/2010 |
| KR | 20130130563 | A | | 12/2013 |
| KR | 20150130453 | A | | 11/2015 |
| KR | 20170140305 | A | | 12/2017 |
| KR | 20180030108 | A | | 3/2018 |
| KR | 20180097536 | A | | 8/2018 |
| KR | 20190066037 | A | | 6/2019 |
| TW | 201211242 | A | | 3/2012 |
| WO | WO00/46595 | A1 | | 8/2000 |
| WO | WO02/088702 | A2 | | 11/2002 |
| WO | WO03/075129 | A2 | | 9/2003 |
| WO | WO2004/040001 | A2 | | 5/2004 |
| WO | WO2004/089810 | A2 | | 10/2004 |
| WO | WO2005/100541 | A2 | | 10/2005 |
| WO | WO2006/038035 | A2 | | 4/2006 |
| WO | WO2007/008609 | A2 | | 1/2007 |
| WO | WO2007/024701 | A2 | | 3/2007 |
| WO | WO2007/092713 | A2 | | 8/2007 |
| WO | WO2008/119066 | A1 | | 10/2008 |
| WO | WO2009/130694 | A2 | | 10/2009 |
| WO | WO2010/040851 | A2 | | 4/2010 |
| WO | WO2010/115167 | A2 | | 10/2010 |
| WO | WO2010/147078 | A1 | | 12/2010 |
| WO | WO2011/160430 | A1 | | 12/2011 |
| WO | WO2012/024658 | A2 | | 2/2012 |
| WO | WO2012/037030 | A2 | | 3/2012 |
| WO | WO2012/072823 | A1 | | 6/2012 |
| WO | WO2012/162779 | A1 | | 12/2012 |
| WO | WO2013/019491 | A1 | | 2/2013 |
| WO | WO2011/149032 | A1 | | 7/2013 |
| WO | WO2013/130714 | A1 | | 9/2013 |
| WO | WO2014/036915 | A1 | | 3/2014 |
| WO | WO2014/084672 | A1 | | 6/2014 |
| WO | WO2014/120821 | A1 | | 8/2014 |
| WO | WO2015/048573 | A1 | | 4/2015 |
| WO | WO2015/199162 | A1 | | 12/2015 |
| WO | WO2016/048994 | A2 | | 3/2016 |
| WO | WO2016/054557 | A1 | | 4/2016 |
| WO | WO2017/181135 | A2 | | 10/2017 |
| WO | WO2018/064640 | A1 | | 4/2018 |
| WO | WO-2018076024 | A2 | * 4/2018 | ........ B01L 3/502715 |
| WO | WO2018/126205 | A1 | | 7/2018 |
| WO | WO2020/077274 | A1 | | 4/2020 |

OTHER PUBLICATIONS

Chung et al., Imaging single-cell signaling dynamics with a deterministic high-density single-cell trap array; Anal.Chem.; 83(18); pp. 7044-7052; 14 p. (Author Manuscript); Aug. 23, 2011.
CN101275114A, Lou—Machine Translation, Oct. 1, 2008, 8 pages.
Hsu et al.; Sorting Of Differentiated Neurons Using Phototransistor-Based Optoelectronic Tweezers for Cell Replacement Therapy of Neurodegenerative Diseases; Transducers 2009 Conf.; pp. 1598-1601; Jun. 2009.
Hung et al.; Continuous Perfusion Microfluidic Cell Culture Array for High-Throughput Cell-Based Assays; Biotech and Bioengineering 89(1); pp. 1-8 ; Jan. 2005.
Iliescu et al.; Continuous field-flow separation of particle populations in a dielectrophoretic chip with three dimensional electrodes; Applied Physics Letters 90(23); pp. 234104, 4pages; Jun. 2007.
JP2012034641_Centre Nat Rec Scien—Fourmy—Machine Translation, Feb. 23, 2012, 13 pages.
Lee et al.; Microchip-based one step DNA extraction and real-time PCR in one chamber for rapid pathogen identification; Lab on Chip; 6(7); pp. 886-895; (year of pub. sufficiently earlier than effective US filing date and any foreign priority date) 2006.
KIPO computer-generated English language translation of KR 201000008222A_Kyun; 10 pages.
Nevill et al.; Integrated Microfluidic Cell Culture and Lysis on a Chip; Lab Chip; (12) pp. 1689-1695; Oct. 2007.
Ramadan et al.; Simulataneous cell lysis and bead trapping in continuous flow microfluidic device; Sensors and Actuators B; 138(19); pp. 944-955; Jun. 2005.
Somaweera et al.; "Generation of a Chemical Gradient Across an Array of 256 Cell Cultures in a Single Chip"; Analyst; 138(19); pp. 5566-5571; 14 pgs.; (Author Manuscript); Oct. 2013.
TW201211242A Geneasys Pty Ltd.—Silverbrook—Machine tranlation, Mar. 16, 2012; 59 pages.
Valley et al.; Optoelectronic Tweezers as a Tool for Parallel Single-Cell Manipulation and Stimulation; IEEE Trans Biomed Circuits Syst.; 3(6); pp. 424-431; Dec. 2009.
WO2010147078, University of Tokyo, Machine Translation, Dec. 23, 2010; 12 pages.
Xu et al.; Recent Trends in Dielectrophoresis; Informacije MIDEM; 40(4) pp. 253-262; Dec. 2010.
Yi et al.; Microfluidics Technology for Manipulation and Analysis of Biological Cells; Anal Chim Acta; (560) pp. 1-23; Feb. 2006.
Chen et al.; Microfluidic approaches for cancer cell detection, characterization, and separation; Lab on a Chip; 12(10); pp. 1753-1767; 2012 (the year of publication is sufficiently earlier than the effective U.S. filing date and any foreign priority date so that the particular month of publication is not an issue).

(56) References Cited

OTHER PUBLICATIONS

Zhang et al.; "Click" Chemistry-Based Surface Modification of poly(dimethylsiloxane) for Protein Separation in a Microfluidic Chip; Electrophoresis; 31(18); p. 3129-3136; Sep. 20, 2010.
Zhang et al.;Azide Functional Monolayers Grafted to a Germanium Surface Model Substrates for ATR-IR Studies of interfacial Click Reactions; Langmuir ; 28(1); pp. 486-493; Dec. 8, 2011.

* cited by examiner

704 DNA Barcode
706 Gene Sequence

710
Design mutational library for target protein-of-interest, encoded by known barcode sequences.

722
704
706

720
Synthesize bead-based library.

730
Import library of beads containing individual mutated gene sequence into microfluidic chip.

Imoport a single bead into an individual unswept region 708 of the microfluidic chip Read out barcodes 704 from beads in each unswept region; correlate gene sequences 702, 702', 702" on bead to location of unswept region.

Introduce a phenotypic reporter 724 into unswept region 708 with individual bead 722

Flow cell-free expression system through channels and permit diffusion into unswept region 708.

SYSTEMS AND METHODS FOR IDENTIFICATION OF OPTIMIZED PROTEIN PRODUCTION AND KITS THEREFOR

CROSS REFERENCE TO RELATED APPLICATIONS

This application is a continuation of International Appln. No. PCT/US2019/055953, filed Oct. 11, 2019; which claims the benefit of U.S. Provisional Application No. 62/744,578, filed Oct. 11, 2018, entitled "SYSTEMS AND METHODS FOR IDENTIFICATION OF OPTIMIZED PROTEIN PRODUCTION AND KITS THEREFOR", which disclosures are herein incorporated by reference in their entirety.

BACKGROUND OF THE INVENTION

In biosciences and related fields, it can be useful to develop optimized proteins for therapeutic or synthetic biologics discovery and production. Some embodiments of the present invention include apparatuses and processes for rapid protein evolution including cycles of gene or sub-gene design and DNA synthesis, cell-free protein production and detection/evaluation of the product protein function.

SUMMARY OF THE INVENTION

In a first aspect, a system for rapid protein evolution is provided, the system including a microfluidic device; and a microfluidic system component (e.g., instrument) configured to: import a plurality of beads into the microfluidic device, each bead of the plurality including (i) one nucleic acid sequence of a first plurality of nucleic acid sequences, wherein each nucleic acid of the first plurality comprises a sequence variant of a nucleic acid sequence encoding a protein of interest, and (ii) a barcode; incubate the plurality of beads located within the microfluidic device under conditions conducive to expression of a corresponding protein encoded by the one nucleic acid sequence of each bead of the plurality of beads, thereby producing a plurality of corresponding proteins; and assay for a desired property in the plurality of corresponding proteins produced from the nucleic acid sequences of the plurality of beads. The system may include a plurality of protein aggregation beads which specifically bind to an epitope of the protein of interest or a protein tag (e.g., epitope tags, such as FLAG-tag, metal chelating tag like His6, FlASH, ReAsH, and the like).

In some variations, the system may include a nucleic acid synthesis component configured to synthesize the first plurality of nucleic acid sequences (e.g., and any subsequent plurality of nucleic acid sequences). Each nucleic acid sequence of the first plurality of nucleic acid sequences may encode for a sequence variant of the protein of interest. The system may include a bead preparation component configured to connect each of the first plurality of nucleic acid sequences to a bead (e.g., thereby generating the first plurality of beads and/or any subsequent plurality of beads). The bead preparation component may be a separate apparatus from the nucleic acid synthesis component, or it may be part of the same component.

In some variations, the system may include a barcode detection component, configured to correlate the nucleic acid sequence of each bead of the plurality of beads with the location of the corresponding bead of the plurality of beads within the microfluidic device. The barcode detection component may include an optical subsystem of the microfluidic system component, configured to detect the barcode visually. The barcode detection component may include a nucleic acids sequencing component configured to determine the barcode by sequencing.

In some variations, the system may include a computational component (e.g., computer) configured to correlate results from the desired property assay with individual nucleic acid sequences of the first plurality of nucleic acid sequences; and, based upon the correlation, design a second plurality of nucleic acid sequences, each encoding for a further sequence variant of the protein of interest. The computational component may further be configured to communicate the design of the second plurality of nucleic acid sequences to the nucleic acids synthesis component.

In some variations, the microfluidic device may include a housing including a base and a microfluidic structure disposed on a surface of the base, wherein the base and the microfluidic structure define an interior chamber for holding a first liquid medium and micro-objects suspended therein. The microfluidic structure of the microfluidic device may include a flow path for the first liquid medium; and a plurality of physical sequestration pens. Each sequestration pen of the plurality may include an enclosure; and a single opening to the flow path, and wherein the enclosure encloses an interior space structured to hold a micro-object suspended in a second liquid medium. Each sequestration pen of the plurality may further include an inner wall extending from the opening into the enclosure. The opening of each sequestration pen of the plurality of sequestration pens of the microfluidic device may be oriented such that no part is facing directly into the flow path, whereby, when the channel contains a flow of the first liquid medium and the sequestration pen contains the second liquid medium, a direct flow of the first liquid medium into the second liquid medium in the interior space is impeded while diffusive mixing of the first liquid medium with the second liquid medium in the interior space is allowed. Each sequestration pen of the plurality may include an isolation region and a connection region that fluidically connects the isolation region to the flow path, and wherein the isolation region is an unswept region in the microfluidic device. The connection region may include a proximal opening into the flow path having a width $W_{con}$ ranging from about 20 microns to about 100 microns and a distal opening into the isolation region, and wherein a length $L_{con}$ of the connection region from the proximal opening to the distal opening is as least 1.0 times the width $W_{con}$ of the proximal opening of the connection region. The flow path may include a microfluidic channel, and wherein each sequestration pen of the plurality opens to the microfluidic channel.

In some variations, the microfluidic device may further include a DEP configuration including: a first electrode; an electrode activation substrate; and a second electrode, where the first electrode is part of a first wall of the interior chamber and the electrode activation substrate and the second electrode are part of a second wall of the interior chamber, and wherein the electrode activation substrate comprises a photoconductive material, semiconductor integrated circuits, or phototransistors.

In another aspect, a process for evolving a protein is provided, the process including disposing a first library of nucleic acid sequences within a microfluidic device, wherein individual nucleic acid sequences of the first library are bound to corresponding beads, and wherein the microfluidic device includes a housing including a base and a microfluidic structure disposed on a surface of the base, wherein the base and the microfluidic structure define an interior chamber for holding a first liquid medium and micro-objects suspended therein, and further wherein each nucleic acid sequence of the first library includes one or more variations from a nucleic acid sequence encoding an protein sequence of interest (e.g., an original protein sequence of interest, which may be from a naturally occurring protein or a non-naturally occurring protein, in either case having a characterized activity); introducing a phenotypic reporter into the microfluidic device and disposing it in proximity to each nucleic acid sequence of the first library, wherein the phenotypic reporter includes a solution phase reagent and/or a plurality of micro-objects, and is configured to provide a phenotypic readout from the protein sequence of interest; introducing a reagent mixture into the microfluidic device and disposing it in proximity to each nucleic acid sequence of the first library, wherein the reagent mixture is configured to express a protein sequence from each nucleic acid sequence of the first library; expressing the protein sequence from each nucleic acid sequence of the first library; detecting the phenotypic readout from a region proximal to one or more nucleic acid sequences of the first library; identifying individual nucleic acid sequences from the first library having a corresponding proximal region with a desired phenotypic readout; and determining the sequence of the identified nucleic acid sequences of the first library.

In some variations, the process may further include correlating the individual nucleic acid sequences of the first library with the phenotypic readout detected in the corresponding proximal regions; and designing a second library of nucleic acid sequences, wherein each nucleic acid sequence of the second library includes one or more variations from the nucleic acid sequence encoding the protein sequence of interest, with the one or more variations of the nucleic acid sequences of the second library selected in light of the correlation. Each nucleic acid sequence of the first library can be linked to a corresponding bead of a first plurality of beads. Each bead of the first plurality of beads may include a plurality of linked nucleic acids, each linked nucleic acid including the same variation of the nucleic acid sequence encoding the protein sequence of interest In some variations, the may process further include designing the nucleic acid sequences of the first library to vary from the nucleic acid sequence encoding the protein sequence of interest; synthesizing the nucleic acid sequences of the first library; and connecting each nucleic acid sequence of the first library to a corresponding bead of the first plurality of beads, thereby forming a first library of nucleic acid bearing beads.

In some variations, each bead of the first plurality of beads may further include a corresponding distinct barcode. The distinct barcodes may include distinct nucleic acid sequences. The process may further include reading the barcode of each bead of the first plurality of beads after disposing the first library of nucleic acid sequences in the microfluidic device, thereby identifying a location of each bead and its corresponding nucleic acid sequence within the microfluidic device. The process may further include reading the barcode of each bead of the first plurality of beads (e.g., after detecting the phenotypic readout).

In some variations, the process may further include disposing a plurality of protein aggregation beads within the microfluidic device and disposing one or more protein aggregation beads of the plurality in proximity to each nucleic acid sequence of the first library, wherein the protein aggregation beads of the plurality specifically bind to (i) an epitope of the protein sequence of interest or (ii) a protein tag (e.g., an epitope tag) encoded by each nucleic acid sequence of the first library so as to be functionally included in the protein sequence expressed therefrom. The process may further include capturing the expressed protein from each nucleic acid sequence of the first library to the one or more protein aggregation beads disposed in proximity thereto.

In some variations, the process may further include flowing a flushing medium through the microfluidic device after expressing the protein sequence, thereby displacing the reagent mixture. Flowing the flushing medium through the microfluidic device may be performed before detecting the phenotypic reporter. Introducing the phenotypic reporter and disposing it in proximity to each nucleic acid of the first plurality may be performed after disposing the reagent mixture in proximity to each nucleic acid sequence of the first library and/or flowing the flushing medium through the microfluidic device.

In some variations, the microfluidic structure of the microfluidic device may include (i) a flow path for the first liquid medium; and (ii) a plurality of physical sequestration pens. Each sequestration pen of the plurality may include an enclosure; and a single opening to the flow path; wherein the enclosure encloses an interior space structured to hold a biological micro-object suspended in a second liquid medium. Each sequestration pen of the plurality may further include an inner wall extending from the opening into the enclosure. The opening of each sequestration pen of the plurality of sequestration pens of the microfluidic device may be oriented such that no part is facing directly into the flow path, whereby, when the flow path contains a flow of the first liquid medium and the sequestration pen contains the second liquid medium, a direct flow of the first liquid medium into the second liquid medium in the interior space is impeded while diffusive mixing of the first liquid medium with the second liquid medium in the interior space is allowed. In some embodiments, the microfluidic device may further include a DEP configuration including: a first electrode; an electrode activation substrate; and a second electrode, wherein the first electrode is part of a first wall of the interior chamber and the electrode activation substrate and the second electrode are part of a second wall of the interior chamber, and wherein the electrode activation substrate comprises a photoconductive material, semiconductor integrated circuits, or phototransistors.

Disposing the first library of nucleic acid sequences within the microfluidic device may include introducing individual beads of the first plurality of beads into individual sequestration pens of the plurality of sequestration pens. No more than one bead of the first plurality of beads may introduced into each sequestration pen of the plurality of sequestration pens.

In some variations, introducing the phenotypic reporter into the microfluidic device may include introducing one or more micro-objects of the plurality of micro-objects into individual sequestration pens containing a nucleic acid sequence of the first library of nucleic acid sequences.

In some variations, the protein of interest includes an enzyme. The protein of interest may include a domain which binds to a cell surface marker. The cell surface marker may be a cell surface receptor (e.g., a receptor involved in intercellular signaling) or a glycoprotein. The protein of interest may include an antibody (e.g., an antibody fragment such as a single-chain antibody, e.g., a single chain variable domain, a nanobody, or the like, and optionally, an antibody that lacks glycosylation).

In some variations, the phenotypic reporter may include a solution phase reagent providing a detectable signal when contacted by the protein of interest (e.g., the reagent could be cleaved by the protein of interest, and the cleavage could result in the emission of detectable light). The phenotypic reporter may include micro-objects including binding sites for the protein of interest, reporter cells configured to report a function of the protein of interest, or micro-objects providing enzymatic substrates for an enzymatic activity of the protein of interest.

In some variations, correlating the individual nucleic acid sequences of the first library with the phenotypic readout detected in the corresponding proximal regions may be performed by a first computer component configured to identify a function of the expressed protein from the identified nucleic acid sequences that is more desirable than the function of the protein of interest. Designing the second library of nucleic acid sequences may be performed by a second computer component, based on the correlation of the expressed protein function with the nucleic acid sequences of the first library of nucleic acid sequences. The first computer component may be the same as the second computer component. The first computer component may employ a machine learning algorithm to perform the correlation. The second computer component may employ a machine learning algorithm to design the second library of nucleic acid sequences.

In some variations, the reagent mixture may include a cell free protein expression reaction mixture. Introducing the reagent mixture may include flowing the reagent mixture into the flow path and permitting the reagent mixture to diffuse into the sequestration pens. The first (and/or the second) library of nucleic acid sequences may be synthesized by a parallel nucleic acids synthesizer. The parallel nucleic acids synthesizer may be a massively parallel nucleic acids synthesizer. The parallel nucleic acids synthesizer may be configured to assemble a plurality of short-length synthesized nucleic acids into a longer conjoined nucleic acid. The parallel nucleic acids synthesizer configured to assemble longer conjoined nucleic acids may further be configured to assemble a plurality of longer conjoined nucleic acids in parallel. Each of the second library of nucleic acid sequences may be linked to a corresponding bead to form a second library of nucleic acid bearing beads.

In some variations, the process of disposing a first library of nucleic acid sequences, introducing a phenotypic reporter, expressing the protein sequence, detecting the phenotypic readout, identifying individual nucleic acid sequences, and determining the sequence of the identified nucleic acid sequences is repeated using the second library of nucleic acid sequences in place of the first library of nucleic acid sequences. A further library of nucleic acid sequences may be designed and synthesized. The nucleic acid sequences of the further library of nucleic acid sequences may be linked to corresponding beads to form a further library of nucleic acid bearing beads. The first library of nucleic acid sequences may include variations within a sub-region of the nucleic acid sequence encoding the protein of interest. The sub-region of the nucleic acid sequence encoding the protein of interest may encode for a region of the protein producing a function of interest. The sub-region may encode for an enzymatic active site or a binding site (e.g., an antigen recognition site or a protein-protein binding site) of the original protein of interest.

In some variations, the first library of nucleic acid sequences may include variations throughout the length of the nucleic acid sequence encoding the protein of interest. The second library of nucleic acid sequences and/or the further library of nucleic acid sequences may include variations within a sub-region of the nucleic acid sequence encoding the protein of interest. The sub-region of the nucleic acid sequence encoding the protein of interest may encode for a region of the protein producing a function of interest. The sub-region may encode for an enzymatic active site or a binding site (e.g., an antigen recognition site or a protein-protein binding site) of the protein of interest. The second library of nucleic acid sequences and/or the further library of nucleic acid sequences may include variations throughout the length of the nucleic acid sequence encoding the protein of interest.

In another aspect, a kit for rapid evolution of a protein of interest is provided, the kit including a microfluidic device, wherein the microfluidic device includes a housing including a base and a microfluidic structure disposed on a surface of the base, wherein the base and the microfluidic structure define an interior chamber for holding a first liquid medium and micro-objects suspended therein; and a phenotypic reporter. The phenotypic reporter may include a solution phase reagent providing a detectable signal when contacted by the protein of interest (e.g., the reagent could be cleaved by the protein of interest, and the cleavage could result in the emission of detectable light).

In some variations, the phenotypic reporter may include a plurality of micro-objects, each micro-object configured to provide a phenotypic readout from the protein sequence of interest. The micro-objects of the plurality of micro-objects may include binding sites for the protein of interest, include enzymatic substrates for an enzymatic activity of the protein of interest, and/or are reporter cells configured to report a function of the protein of interest.

In some embodiments, the microfluidic structure of the microfluidic device may include (i) a flow path for the first liquid medium; and (ii) a plurality of physical sequestration pens. Each sequestration pen of the plurality of sequestration pens may include an enclosure; and a single opening to the flow path; wherein the enclosure encloses an interior space structured to hold a micro-object suspended in a second liquid medium. The sequestration pen may include an inner wall extending from the opening into the enclosure. The opening of each sequestration pen of the plurality of sequestration pens of the microfluidic device may be oriented such that no part is facing directly into the flow path of the channel, whereby, when the channel contains a flow of the first liquid medium and the sequestration pen contains the second liquid medium, a direct flow of the first liquid medium into the second liquid medium in the interior space is impeded while diffusive mixing of the first liquid medium with the second liquid medium in the interior space is allowed. In some variations, the microfluidic device may further include a DEP configuration including: a first electrode; an electrode activation substrate; and a second electrode, wherein the first electrode is part of a first wall of the interior chamber and the electrode activation substrate and the second electrode are part of a second wall of the interior chamber, and wherein the electrode activation substrate comprises a photoconductive material, semiconductor integrated circuits, or phototransistors.

In some variations, the kit may further include a reagent mixture for expressing protein from a nucleic acid sequence in vitro. The reagent mixture may be a cell free protein expression mixture. The kit further may further include a plurality of beads, each configured to bind to a nucleic acid sequence. Each bead of the plurality of beads may include a unique barcode. The unique barcode may be a unique nucleic acid sequence. The kit may further include a plurality of protein aggregation beads. Each of the plurality of protein aggregation beads may specifically bind an epitope of the protein of interest or a protein tag.

In some variations, kit may further include machine readable instructions for a computer component or computer components. The machine readable instructions may enable the computer component or computer components to correlate individual nucleic acid sequences of a library of nucleic acid sequences with phenotypes associated with the individual nucleic acid sequences; and/or design a library of nucleic acid sequences, wherein each nucleic acid sequence of the library includes one or more variations from a nucleic acid sequence encoding an protein sequence of interest and, optionally, wherein the library design is based upon a correlation between a plurality of individual nucleic acid sequences and phenotypes associated with the individual nucleic acid sequences.

DETAILED DESCRIPTION

Figure 1A:
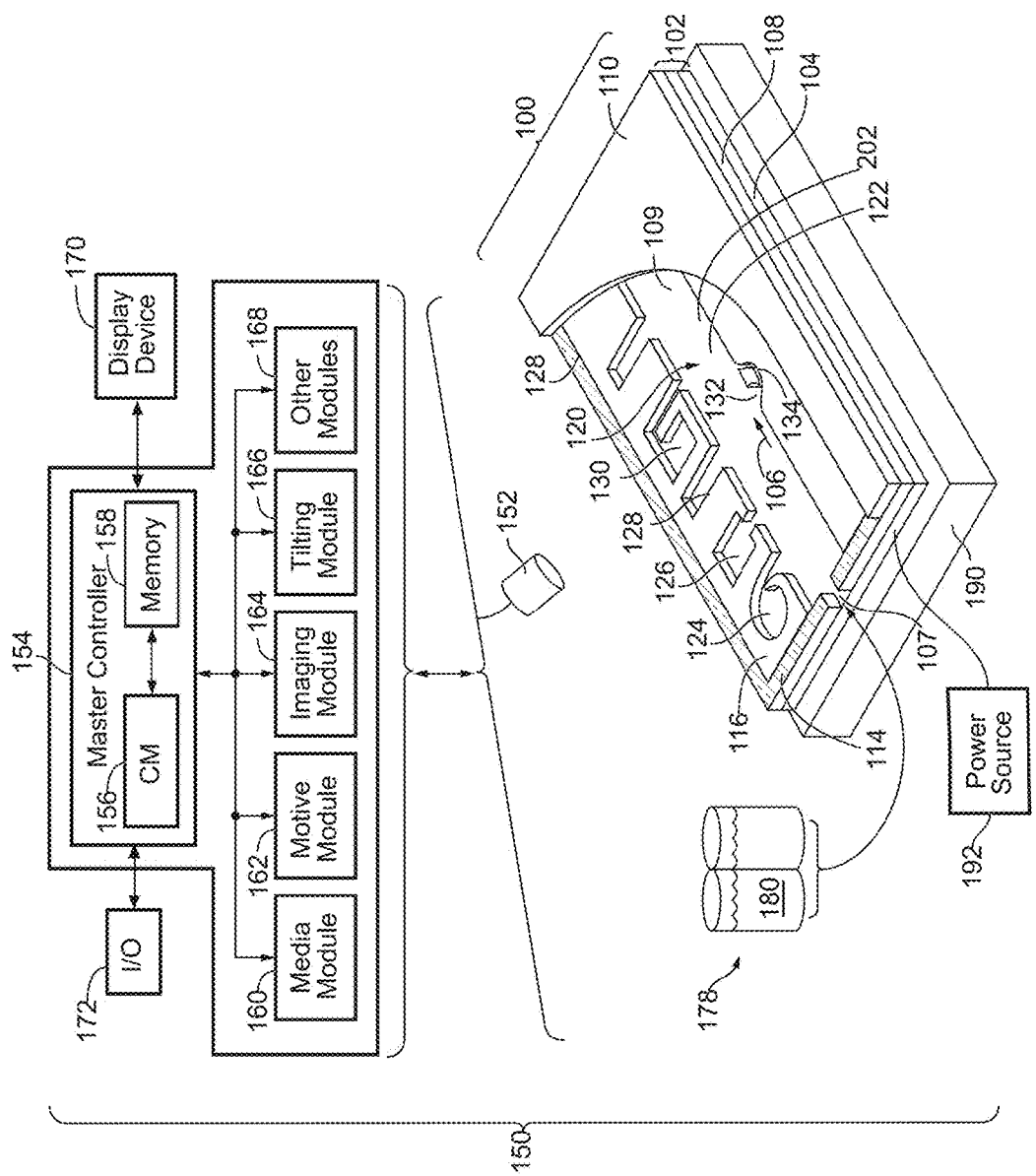
FIG. 1A illustrates a microfluidic device and a system with associated control equipment according to some embodiments of the disclosure.

This specification describes exemplary embodiments and applications of the disclosure. The disclosure, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms "on," "attached to," "connected to," "coupled to," or similar words are used herein, one element (e.g., a material, a layer, a substrate, etc.) can be "on," "attached to," "connected to," or "coupled to" another element regardless of whether the one element is directly on, attached to, connected to, or coupled to the other element or there are one or more intervening elements between the one element and the other element. Also, unless the context dictates otherwise, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements. Section divisions in the specification are for ease of review only and do not limit any combination of elements discussed.

Where dimensions of microfluidic features are described as having a width or an area, the dimension typically is described relative to an x-axial and/or y-axial dimension, both of which lie within a plane that is parallel to the substrate and/or cover of the microfluidic device. The height of a microfluidic feature may be described relative to a z-axial direction, which is perpendicular to a plane that is parallel to the substrate and/or cover of the microfluidic device. In some instances, a cross sectional area of a microfluidic feature, such as a channel or a passageway, may be in reference to an x-axial/z-axial, a y-axial/z-axial, or an x-axial/y-axial area.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

The term "ones" means more than one.

As used herein, the term "plurality" can be 2, 3, 4, 5, 6, 7, 8, 9, 10, or more.

As used herein: μm means micrometer, $μm^3$ means cubic micrometer, pL means picoliter, nL means nanoliter, and μL (or uL) means microliter.

As used herein, the term "disposed" encompasses within its meaning "located."

As used herein, a "microfluidic device" or "microfluidic apparatus" is a device that includes one or more discrete microfluidic circuits configured to hold a fluid, each microfluidic circuit comprised of fluidically interconnected circuit elements, including but not limited to region(s), flow path(s), channel(s), chamber(s), and/or pen(s), and at least one port configured to allow the fluid (and, optionally, micro-objects suspended in the fluid) to flow into and/or out of the microfluidic device. Typically, a microfluidic circuit of a microfluidic device will include a flow region, which may include or be a microfluidic channel, and at least one chamber, and will hold a volume of fluid of less than about 1 mL, e.g., less than about 750, 500, 250, 200, 150, 100, 75, 50, 25, 20, 15, 10, 9, 8, 7, 6, 5, 4, 3, or 2 microliters. In certain embodiments, the microfluidic circuit holds about 1-2, 1-3, 1-4, 1-5, 2-5, 2-8, 2-10, 2-12, 2-15, 2-20, 5-20, 5-30, 5-40, 5-50, 10-50, 10-75, 10-100, 20-100, 20-150, 20-200, 50-200, 50-250, or 50-300 microliters. The microfluidic circuit may be configured to have a first end fluidically connected with a first port (e.g., an inlet) in the microfluidic device and a second end fluidically connected with a second port (e.g., an outlet) in the microfluidic device.

As used herein, a "nanofluidic device" or "nanofluidic apparatus" is a type of microfluidic device having a microfluidic circuit that contains at least one circuit element configured to hold a volume of fluid of less than about 1 microliters, e.g., less than about 750, 500, 250, 200, 150, 100, 75, 50, 25, 20, 15, 10, 9, 8, 7, 6, 5, 4, 3, 2, 1 nL or less. A nanofluidic device may comprise a plurality of circuit elements (e.g., at least 2, 3, 4, 5, 6, 7, 8, 9, 10, 15, 20, 25, 50, 75, 100, 150, 200, 250, 300, 400, 500, 600, 700, 800, 900, 1000, 1500, 2000, 2500, 3000, 3500, 4000, 4500, 5000, 6000, 7000, 8000, 9000, 10,000, or more). In certain embodiments, one or more (e.g., all) of the at least one circuit elements is configured to hold a volume of fluid of about 100 pL to 1 nL, 100 pL to 2 nL, 100 pL to 5 nL, 250 pL to 2 nL, 250 pL to 5 nL, 250 pL to 10 nL, 500 pL to 5 nL, 500 pL to 10 nL, 500 pL to 15 nL, 750 pL to 10 nL, 750 pL to 15 nL, 750 pL to 20 nL, 1 to 10 nL, 1 to 15 nL, 1 to 20 nL, 1 to 25 nL, or 1 to 50 nL. In other embodiments, one or more (e.g., all) of the at least one circuit elements are configured to hold a volume of fluid of about 20 nL to 200 nL, 100 to 200 nL, 100 to 300 nL, 100 to 400 nL, 100 to 500 nL, 200 to 300 nL, 200 to 400 nL, 200 to 500 nL, 200 to 600 nL, 200 to 700 nL, 250 to 400 nL, 250 to 500 nL, 250 to 600 nL, or 250 to 750 nL.

A microfluidic device or a nanofluidic device may be referred to herein as a "microfluidic chip" or a "chip"; or "nanofluidic chip" or "chip".

A "microfluidic channel" or "flow channel" as used herein refers to flow region of a microfluidic device having a length that is significantly longer than both the horizontal and vertical dimensions. For example, the flow channel can be at least 5 times the length of either the horizontal or vertical dimension, e.g., at least 10 times the length, at least 25 times the length, at least 100 times the length, at least 200 times the length, at least 500 times the length, at least 1,000 times the length, at least 5,000 times the length, or longer. In some embodiments, the length of a flow channel is about 100,000 microns to about 500,000 microns, including any value therebetween. In some embodiments, the horizontal dimension is about 100 microns to about 1000 microns (e.g., about 150 to about 500 microns) and the vertical dimension is about 25 microns to about 200 microns, (e.g., from about 40 to about 150 microns). It is noted that a flow channel may have a variety of different spatial configurations in a microfluidic device, and thus is not restricted to a perfectly linear element. For example, a flow channel may be, or include one or more sections having, the following configurations: curve, bend, spiral, incline, decline, fork (e.g., multiple different flow paths), and any combination thereof. In addition, a flow channel may have different cross-sectional areas along its path, widening and constricting to provide a desired fluid flow therein. The flow channel may include valves, and the valves may be of any type known in the art of microfluidics. Examples of microfluidic channels that include valves are disclosed in U.S. Pat. No. 6,408,878 (Unger et al.) and U.S. Pat. No. 9,227,200 (Chiou et al.), each of which is herein incorporated by reference in its entirety.

As used herein in reference to a fluidic medium, "diffuse" and "diffusion" refer to thermodynamic movement of a component of the fluidic medium down a concentration gradient.

The phrase "flow of a medium" means bulk movement of a fluidic medium primarily due to any mechanism other than diffusion. For example, flow of a medium can involve movement of the fluidic medium from one point to another point due to a pressure differential between the points. Such flow can include a continuous, pulsed, periodic, random, intermittent, or reciprocating flow of the liquid, or any combination thereof. When one fluidic medium flows into another fluidic medium, turbulence and mixing of the media can result.

The phrase "substantially no flow" refers to a rate of flow of a fluidic medium that, averaged over time, is less than the rate of diffusion of components of a material (e.g., an analyte of interest) into or within the fluidic medium. The rate of diffusion of components of such a material can depend on, for example, temperature, the size of the components, and the strength of interactions between the components and the fluidic medium.

As used herein in reference to different regions within a microfluidic device, the phrase "fluidically connected" means that, when the different regions are substantially filled with fluid, such as fluidic media, the fluid in each of the regions is connected so as to form a single body of fluid. This does not mean that the fluids (or fluidic media) in the different regions are necessarily identical in composition. Rather, the fluids in different fluidically connected regions of a microfluidic device can have different compositions (e.g., different concentrations of solutes, such as proteins, carbohydrates, ions, or other molecules) which are in flux as solutes move down their respective concentration gradients and/or fluids flow through the microfluidic device.

As used herein, a "flow path" refers to one or more fluidically connected circuit elements (e.g., channel(s), region(s), chamber(s) and the like) that define, and are subject to, the trajectory of a flow of medium. A flow path is thus an example of a swept region of a microfluidic device. Other circuit elements (e.g., unswept regions) may be fluidically connected with the circuit elements that comprise the flow path without being subject to the flow of medium in the flow path.

As used herein, "isolating a micro-object" constitutes confining a micro-object to a defined area within the microfluidic device.

As used herein, an "isolation region" refers to a region within a microfluidic device that is configured to hold a micro-object such that the micro-object is not drawn away from the region as a result of fluid flowing through the microfluidic device. Depending upon context, the term "isolation region" can further refer to the structures that define the region, which can include a base/substrate, walls (e.g., made from microfluidic circuit material), and a cover.

A microfluidic (or nanofluidic) device can comprise "swept" regions and "unswept" regions. As used herein, a "swept" region is comprised of one or more fluidically interconnected circuit elements of a microfluidic circuit, each of which experiences a flow of medium when fluid is flowing through the microfluidic circuit. The circuit elements of a swept region can include, for example, regions, channels, and all or parts of chambers. As used herein, an "unswept" region is comprised of one or more fluidically interconnected circuit element of a microfluidic circuit, each of which experiences substantially no flux of fluid when fluid is flowing through the microfluidic circuit. An unswept region can be fluidically connected to a swept region, provided the fluidic connections are structured to enable diffusion but substantially no flow of media between the swept region and the unswept region. The microfluidic device can thus be structured to substantially isolate an unswept region from a flow of medium in a swept region, while enabling substantially only diffusive fluidic communication between the swept region and the unswept region. For example, a flow channel of a micro-fluidic device is an example of a swept region while an isolation region (described in further detail below) of a microfluidic device is an example of an unswept region.

As used herein, the term "transparent" refers to a material which allows visible light to pass through without substantially altering the light as is passes through.

As used herein, "brightfield" illumination and/or image refers to white light illumination of the microfluidic field of view from a broad-spectrum light source, where contrast is formed by absorbance of light by objects in the field of view.

As used herein, "structured light" is projected light that is modulated to provide one or more illumination effects. A first illumination effect may be projected light illuminating a portion of a surface of a device without illuminating (or at least minimizing illumination of) an adjacent portion of the surface, e.g., a projected light pattern, as described more fully below, used to activate DEP forces within a DEP substrate. When using structured light patterns to activate DEP forces, the intensity, e.g., variation in duty cycle of a structured light modulator such as a DMD, may be used to change the optical power applied to the light activated DEP actuators, and thus change DEP force without changing the nominal voltage or frequency. Another illumination effect that may be produced by structured light includes projected light that may be corrected for surface irregularities and/or for irregularities associated with the light projection itself, e.g., fall-off at the edge of an illuminated field. Structured light is typically generated by a structured light modulator, such as a digital mirror device (DMD), a microshutter array system (MSA), a liquid crystal display (LCD), or the like. Illumination of a small area of the surface, e.g., a selected area of interest, with structured light improves the signal-to-noise-ratio (SNR), as illumination of only the selected area of interest reduces stray/scattered light, thereby lowering the dark level of the image. An important aspect of structured light is that it may be changed quickly over time. A light pattern from the structured light modulator, e.g., DMD, may be used to autofocus on difficult targets such as clean mirrors or surfaces that are far out of focus. Using a clean mirror, a number of self-test features may be replicated such as measurement of modulation transfer function and field curvature/tilt, without requiring a more expensive Shack-Hartmann sensor. In another use of structured light patterns, spatial power distribution may be measured at the sample surface with a simple power meter, in place of a camera. Structured light patterns may also be used as a reference feature for optical module/system component alignment as well used as a manual readout for manual focus. Another illumination effect made possible by use of structured light patterns is selective curing, e.g., solidification, of hydrogels within the microfluidic device.

As used herein, the "clear aperture" of a lens (or lens assembly) is the diameter or size of the portion of the lens (or lens assembly) that can be used for its intended purpose. In some instances, the clear aperture can be substantially equal to the physical diameter of the lens (or lens assembly). However, owing to manufacturing constraints, it can be difficult to produce a clear aperture equal to the actual physical diameter of the lens (or lens assembly).

As used herein, the term "active area" refers to the portion of an image sensor or structured light modulator that can be used, respectively, to image or provide structured light to a field of view in a particular optical apparatus. The active area is subject to constraints of the optical apparatus, such as the aperture stop of the light path within the optical apparatus. Although the active area corresponds to a two-dimensional surface, the measurement of active area typically corresponds to the length of a diagonal line through opposing corners of a square having the same area.

As used herein, an "image light beam" is an electromagnetic wave that is reflected or emitted from a device surface, a micro-object, or a fluidic medium that is being viewed by an optical apparatus. The device can be any microfluidic device as described herein. The micro-object and the fluidic medium can be located within such a microfluidic device.

As used herein, the term "micro-object" refers generally to any microscopic object that may be isolated and/or manipulated in accordance with the present disclosure. Non-limiting examples of micro-objects include: inanimate micro-objects such as microparticles; microbeads (e.g., polystyrene beads, Luminex™ beads, or the like); magnetic beads; microrods; microwires; quantum dots, and the like; biological micro-objects such as cells; biological organelles; vesicles, or complexes; synthetic vesicles; liposomes (e.g., synthetic or derived from membrane preparations); lipid nanorafts, and the like; or a combination of inanimate micro-objects and biological micro-objects (e.g., microbeads attached to cells, liposome-coated micro-beads, liposome-coated magnetic beads, or the like). Beads may include moieties/molecules covalently or non-covalently attached, such as fluorescent labels, nucleic acids (e.g., oligonucleotides), proteins, carbohydrates, antigens, small molecule signaling moieties, or other chemical/biological species capable of use in an assay. Lipid nanorafts have been described, for example, in Ritchie et al. (2009) "Reconstitution of Membrane Proteins in Phospholipid Bilayer Nanodiscs," Methods Enzymol., 464:211-231.

As used herein, the term "cell" is used interchangeably with the term "biological cell." Non-limiting examples of biological cells include: eukaryotic cells, plant cells, animal cells, such as mammalian cells, reptilian cells, avian cells, fish cells, or the like; prokaryotic cells, bacterial cells, fungal cells, protozoan cells, or the like; cells dissociated from a tissue, such as muscle, cartilage, fat, skin, liver, or lung cells, neurons, glial cells, and the like; immunological cells, such as T cells, B cells, plasma cells, natural killer cells, macrophages, and the like; embryos (e.g., zygotes), germ cells, such as oocytes, ova, and sperm cells, and the like; fusion cells, hybridomas, cultured cells, cells from a cell line, cancer cells, infected cells, transfected and/or transformed cells, reporter cells, and the like. A mammalian cell can be, for example, from a human, a mouse, a rat, a horse, a goat, a sheep, a cow, a pig, a primate, or the like.

A colony of biological cells is "clonal" if all of the living cells in the colony that are capable of reproducing are daughter cells derived from a single parent cell. In certain embodiments, all the daughter cells in a clonal colony are derived from the single parent cell by no more than 10 divisions. In other embodiments, all the daughter cells in a clonal colony are derived from the single parent cell by no more than 14 divisions. In other embodiments, all the daughter cells in a clonal colony are derived from the single parent cell by no more than 17 divisions. In other embodiments, all the daughter cells in a clonal colony are derived from the single parent cell by no more than 20 divisions. The term "clonal cells" refers to cells of the same clonal colony.

As used herein, a "colony" of biological cells refers to 2 or more cells (e.g. about 2 to about 20, about 4 to about 40, about 6 to about 60, about 8 to about 80, about 10 to about 100, about 20 to about 200, about 40 to about 400, about 60 to about 600, about 80 to about 800, about 100 to about 1000, or greater than about 1000 cells).

As used herein, the terms "maintaining a cells" and "maintaining cells" refer to providing an environment comprising both fluidic and gaseous components and, optionally a surface that provides the conditions necessary to keep the cell(s) viable and/or expanding.

As used herein, the term "expanding" when referring to cells, refers to increasing in cell number.

A "component" of a fluidic medium is any chemical or biochemical molecule present in the medium, including solvent molecules, ions, small molecules, antibiotics, nucleotides and nucleosides, nucleic acids, amino acids, peptides, proteins, sugars, carbohydrates, lipids, fatty acids, cholesterol, metabolites, or the like.

As used herein, "antibody" refers to an immunoglobulin (Ig) and includes both polyclonal and monoclonal antibodies; multichain antibodies, such as IgG, IgM, IgA, IgE, and IgD antibodies; single chain antibodies, such as camelid antibodies; mammalian antibodies, including primate antibodies (e.g., human), rodent antibodies (e.g., mouse, rat, guinea pig, hamster, and the like), lagomorph antibodies (e.g., rabbit), ungulate antibodies (e.g., cow, pig, horse, donkey, camel, and the like), and canidae antibodies (e.g., dog); primatized (e.g., humanized) antibodies; chimeric antibodies, such as mouse-human, mouse-primate antibodies, or the like; and may be an intact molecule or a fragment thereof (such as a light chain variable region (VL), heavy chain variable region (VH), scFv, Fv, Fd, Fab, Fab' and F(ab)'2 fragments), or multimers or aggregates of intact molecules and/or fragments; and may occur in nature or be produced, e.g., by immunization, synthesis or genetic engineering. An "antibody fragment," as used herein, refers to fragments, derived from or related to an antibody, which bind antigen. In some embodiments, antibody fragments may be derivatized to exhibit structural features that facilitate clearance and uptake, e.g., by the incorporation of galactose residues. The capability of biological micro-objects (e.g., biological cells) to produce specific biological materials (e.g., proteins, such as antibodies) can be assayed in such a microfluidic device. In a specific embodiment of an assay, sample material comprising biological micro-objects (e.g., cells) to be assayed for production of an analyte of interest can be loaded into a swept region of the microfluidic device. Ones of the biological micro-objects (e.g., mammalian cells, such as human cells) can be selected for particular characteristics and disposed in unswept regions. The remaining sample material can then be flowed out of the swept region and an assay material flowed into the swept region. Because the selected biological micro-objects are in unswept regions, the selected biological micro-objects are not substantially affected by the flowing out of the remaining sample material or the flowing in of the assay material. The selected biological micro-objects can be allowed to produce the analyte of interest, which can diffuse from the unswept regions into the swept region, where the analyte of interest can react with the assay material to produce localized detectable reactions, each of which can be correlated to a particular unswept region. Any unswept region associated with a detected reaction can be analyzed to determine which, if any, of the biological micro-objects in the unswept region are sufficient producers of the analyte of interest.

An antigen, as referred to herein, is a molecule or portion thereof that can bind with specificity to another molecule, such as an Ag-specific receptor. An antigen may be any portion of a molecule, such as a conformational epitope or a linear molecular fragment, and often can be recognized by highly variable antigen receptors (B-cell receptor or T-cell receptor) of the adaptive immune system. An antigen may include a peptide, polysaccharide, or lipid. An antigen may be characterized by its ability to bind to an antibody's variable Fab region. Different antibodies have the potential to discriminate among different epitopes present on the antigen surface, the structure of which may be modulated by the presence of a hapten, which may be a small molecule.

In some embodiments, an antigen is a cancer cell-associated antigen. The cancer cell-associated antigen can be simple or complex; the antigen can be an epitope on a protein, a carbohydrate group or chain, a biological or chemical agent other than a protein or carbohydrate, or any combination thereof; the epitope may be linear or conformational.

The cancer cell-associated antigen can be an antigen that uniquely identifies cancer cells (e.g., one or more particular types of cancer cells) or is upregulated on cancer cells as compared to its expression on normal cells. Typically, the cancer cell-associated antigen is present on the surface of the cancer cell, thus ensuring that it can be recognized by an antibody. The antigen can be associated with any type of cancer cell, including any type of cancer cell that can be found in a tumor known in the art or described herein. In particular, the antigen can be associated with lung cancer, breast cancer, melanoma, and the like. As used herein, the term "associated with a cancer cells," when used in reference to an antigen, means that the antigen is produced directly by the cancer cell or results from an interaction between the cancer cell and normal cells.

The capability of biological micro-objects (e.g., biological cells) to produce specific biological materials (e.g., proteins, including but not limited to enzymes or antibodies) can be assayed in a microfluidic device. In a specific embodiment of an assay, sample material comprising biological micro-objects (e.g., cells, organelles, or membranes) to be assayed for production of an analyte of interest can be loaded into a swept region of the microfluidic device. Ones of the biological micro-objects (e.g., mammalian cells or components thereof, such as human cells or components thereof) can be selected for particular characteristics and disposed in unswept regions. The remaining sample material can then be flowed out of the swept region and an assay material flowed into the swept region. Because the selected biological micro-objects are in unswept regions, the selected biological micro-objects are not substantially affected by the flowing out of the remaining sample material or the flowing in of the assay material. The selected biological micro-objects can be allowed to produce analytes of interest. In this specific embodiment, the analytes of interest may diffuse from the unswept regions into the swept region, where the analytes of interest can react with the assay material to produce localized detectable reactions, each of which can be correlated to a particular unswept region. Alternatively, or in addition, assays may be performed upon the analytes of interest while they are still within the unswept regions, or in a swept region adjacent to the unswept regions of the microfluidic device. Generally, the assays can produce localized detectable reactions which may be correlated to a particular unswept region where a particular analyte of interest was produced.

Rapid improvement in the function of target proteins is currently limited by (1) time required to iterate on the design-build-test-learn paradigm, and (2) the ability to generate diversity in mutant libraries (the parameter space for a 100 amino acid protein is astronomical: 20100 possible sequences).

Figure 6:
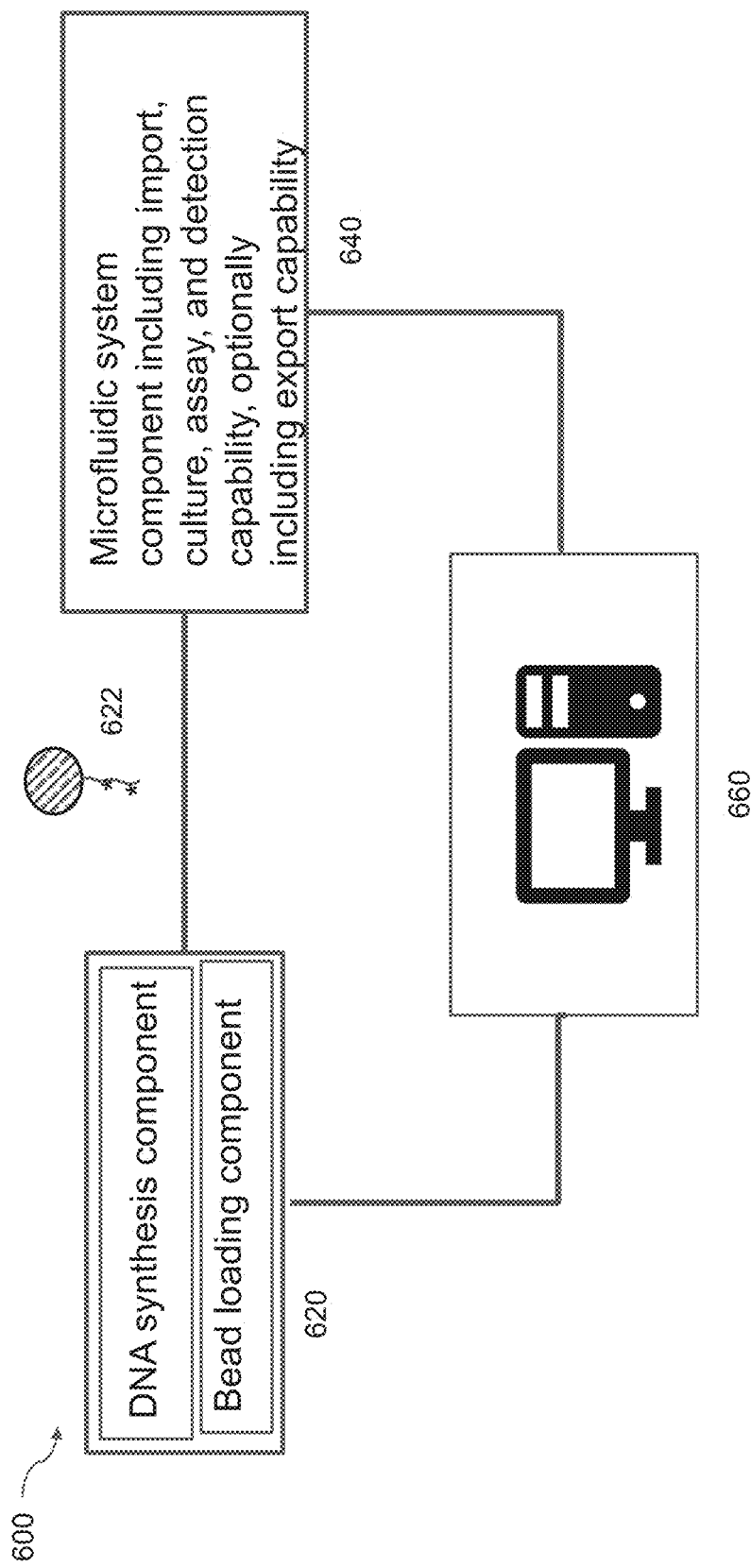
FIG. 6 illustrates a system for rapid protein evolution according to some embodiments of the disclosure.

A fully autonomous, end-to-end workflow can completely automate the design-build-test-learn loop with no human intervention is described and the system for rapid protein evolution 600 is shown in FIG. 6. However, the invention is not so limited that human intervention may not be used where desired. In short, an upfront nucleic acids synthesis component 620 such as a DNA-writing module or DNA synthesizer in combination with a bead loading component can be interfaced with a microfluidic system 640 which includes a microfluidic device configured for import, culturing, assay and, optionally, export of micro-objects such as biological cells and/or beads. The nucleic acids synthesis component 620 can generate tens of thousands of beads 622, each encoding a unique mutated sequence of the target protein. A barcode is also included, such that the identity of the bead may be determined using an in-situ hybridization method, such as that described in International Patent Application No. PCT/US2017/054628 filed on Sep. 29, 2017, entitled "DNA Barcode Compositions and Methods of In Situ Identification in a Microfluidic Device", and incorporated by reference herein for all purposes in its entirety. In some other embodiments of the system, the system includes a nucleic acids sequencing component. The barcode and/or variant nucleic acid sequence may be alternatively be determined by sequencing the nucleic acid sequence of the barcode attached to the bead.

The beads may be flowed into the microfluidic device of microfluidic system 640. In some embodiments, each bead 622 may be sorted into a sequestration pen of the microfluidic device, which may be any sequestration pen as described herein, so that only one bead is present per sequestration pen. Further, the bead may be introduced in the isolation region of the sequestration pen, an unswept region, to minimize influx of expressed protein materials from other sequestration pens. A cell-free expression system is then introduced to enable protein synthesis in the pens. The mutant protein library can then be screened for improvement in desired phenotype-of-interest. The barcode would denote the identity of the mutants, and the sequence information and functional readout could then be used to determine a further optimized set of variant nucleic acid sequences. The correlations may be introduced to a computing component 660 which can use an algorithm, such as a neural network or other machine learning process (e.g., a "deep learning" process) to narrow the diversity or refocus the variations within of a subsequent round of variant nucleic acid sequences. The computing component 660 may generate newly refined nucleic acid sequences which may then be sent to the nucleic acids synthesis module 620 (e.g., a DNA writer) to repeat the process. This general solution applies for applications ranging from evolving enzymes to improve catalytic activity to evolving more functional antibodies. This process may be run without human intervention, completing a full learning loop in 24 hours or less, and use the analysis resulting out of the test portion of the experimental loop to intelligently screen diversities that would not be possible with current technologies.

System. A system for rapid protein evolution is provided, including: a microfluidic device; and a microfluidic system component (e.g., instrument) configured to: import a plurality of beads into the microfluidic device, each bead of the plurality including (i) one nucleic acid sequence of a first plurality of nucleic acid sequences, and (ii) a barcode; incubate the plurality of beads located within the microfluidic device under conditions conducive to expression of a corresponding protein encoded by the one nucleic acid sequence of each bead of the plurality of beads, thereby producing a plurality of corresponding proteins; and assay for a desired property in the plurality of corresponding proteins produced from the nucleic acid sequences of the plurality of beads.

The system may further include a plurality of protein aggregation beads which are configured to specifically bind to an epitope of the original protein of interest or a protein tag (e.g., epitope tags, such as FLAG-tag, metal chelating tag like His6, FlASH, ReAsH, and the like), which may be any suitable protein tag as described below. One or more protein aggregation beads may be disposed within the microfluidic device in proximity to a nucleic acid labelled bead within the microfluidic device. The one or more protein aggregation beads may bind expressed protein produced from a nucleic acid sequence linked to the bead (e.g., a corresponding protein), and concentrate the expressed protein for the assay of the desired property of the corresponding protein.

In some variations, the system may further include a nucleic acid synthesis component configured to synthesize the first plurality of nucleic acid sequences (e.g., and any subsequent plurality of nucleic acid sequences). Each nucleic acid sequence of the first plurality of nucleic acid sequences may encode for a sequence variant of a protein of interest.

The system may further include a bead preparation component configured to connect each of the first plurality of nucleic acid sequences to a bead (e.g., thereby generating the first plurality of beads and/or any subsequent plurality of beads). In some variations, the bead preparation component may be a separate apparatus from the nucleic acid synthesis component.

In some variations, the system may further include a barcode detection component, configured to correlate the nucleic acid sequence of each bead of the plurality of beads with the location of the corresponding bead of the plurality of beads within the microfluidic device. In some embodiments, the barcode detection component may include an optical subsystem of the microfluidic system component, configured to detect the barcode visually.

In some variations, the barcode detection component may include a nucleic acids sequencing component configured to determine the barcode by sequencing the nucleic acid sequence of the barcode. The nucleic acids sequencing component may in addition or alternatively, determine the sequence of the variant nucleic acid present on the nucleic acid labelled bead.

The system may further include a computational component (e.g., computer) configured to: correlate results from the desired property assay with individual nucleic acid sequences of the first plurality of nucleic acid sequences; and, based upon the correlation, design a second plurality of nucleic acid sequences, each encoding for a further sequence variant of the protein of interest. In some variations, the computational component may be further configured to communicate the design of the second plurality of nucleic acid sequences to the nucleic acids synthesis component. In some embodiments, the computational component configured to correlate the results from the desired property assay may be a first computer and the computational component configured to design the second plurality of nucleic acid sequences is a second computer, where the first computer is configured to communicate the results to the second computer. Whether the first computer is the same as the second computer, or the two computers are different, the design of the second library (and further libraries) is based on the correlation of the expressed protein function with the nucleic acid sequences of the tested library. Additionally, the first and/or second computer may employ a machine learning algorithm to design the second (and further) library of nucleic acid sequences.

In some variations, the microfluidic device may include: a housing including a base and a microfluidic structure disposed on a surface of the base, wherein the base and the microfluidic structure define an interior chamber for holding a first liquid medium and micro-objects suspended therein. The microfluidic structure of the microfluidic device may include a flow path for the first liquid medium; and a plurality of physical sequestration pens. Each sequestration pen of the plurality may include an enclosure; and a single opening to the flow path, and wherein the enclosure encloses an interior space structured to hold a micro-object suspended in a second liquid medium. In some variations, each sequestration pen of the plurality may further include an inner wall extending from the opening into the enclosure. In some variations, the opening of each sequestration pen of the plurality of sequestration pens of the microfluidic device may be oriented such that no part is facing directly into the flow path, whereby, when the channel contains a flow of the first liquid medium and the sequestration pen contains the second liquid medium, a direct flow of the first liquid medium into the second liquid medium in the interior space is impeded while diffusive mixing of the first liquid medium with the second liquid medium in the interior space is allowed. Each sequestration pen of the plurality may include an isolation region and a connection region that fluidically connects the isolation region to the flow path. The isolation region is an unswept region in the microfluidic device. In some embodiments, the connection region may include a proximal opening into the flow path having a width $W_{con}$ ranging from about 20 microns to about 100 microns and a distal opening into the isolation region, and wherein a length $L_{con}$ of the connection region from the proximal opening to the distal opening is as least 1.0 times the width $W_{con}$ of the proximal opening of the connection region. In some variations, the flow path may include a microfluidic channel, and each sequestration pen of the plurality opens to the microfluidic channel.

In some variations, the microfluidic device may further include a DEP configuration including: a first electrode; an electrode activation substrate; and a second electrode, wherein the first electrode is part of a first wall of the interior chamber and the electrode activation substrate and the second electrode are part of a second wall of the interior chamber, and wherein the electrode activation substrate comprises a photoconductive material, semiconductor integrated circuits, or phototransistors.

In some variations, the microfluidic device may be like any microfluidic device described herein and may have any combination of features as described for microfluidic devices microfluidic 100, 175, 200, 300, 320, 400, 450, 520 and system attributes as described in FIGS. 1A-5B.

Nucleic acid labelled beads. A nucleic acid labelled bead may be made of any suitable material, such as polymer, metal, ceramic, glass, or any combination thereof. The nucleic acid labelled bead may be magnetic or may not be magnetic. The nucleic acid labelled bead may include a nucleic acid sequence encoding a sequence variant of a protein of interest. The nucleic acid sequence may encode the entire protein sequence of the protein of interest or may encode a selected region of the entire protein sequence. A sequence variant (when referring to a sequence variant including nucleic acid, may also be referred to as a variant nucleic acid sequence or variant sequence) as used herein refers to a protein/nucleic acid sequence that contains one or more nucleotides/amino acids that are different from the nucleic acid sequence encoding the original protein of interest or different from the amino acid sequence of the original protein of interest. For any sequence variant, the variation may be at one, two or more nucleotides of the nucleic acid sequence encoding the original protein of interest. The nucleic acid sequence variant may result in a protein sequence that is different at one, two or more amino acids of the amino acid sequence of the original protein of interest. In the methods described herein, a first library of nucleic acid labelled beads includes a first library of sequence variants of a nucleic acid sequence encoding a protein of interest. After the first set of testing and learning has been completed, a second library of sequence variants may be designed, based on the results of the testing/learning. Each of the sequence variants of the second library of sequence variants are referred to herein as "further sequence variants", as the variation of the nucleic acid sequences from that of the first library of nucleic acid sequence variants (and, in turn, variation from the nucleic acid sequence encoding the amino acid sequence of the original protein of interest) depend upon the results of the phenotypic readout The nucleic acid sequence of the nucleic acid labelled beads may further include a barcode sequence of nucleic acids. The barcode nucleic acid sequence may contain about 6 to about 70 nucleotides; about 6 to about 60 nucleotides; about 6 to about 50 nucleotides; about 6 to about 40 nucleotides, or any number of nucleotides therebetween. The barcode may be designed to be detected visually, as described further herein or may be designed to be determined by sequencing the nucleic acid sequence of the barcode, as is known in the art.

In some variations, the nucleic acid sequence of the nucleic acid labelled beads may further include a nucleic acid sequence encoding a protein tag. The protein tag, when expressed, in the methods described herein, permit the expressed protein to be captured to a protein aggregation bead and concentrated for the phenotypic readout assay. The protein tag may be any suitable protein tag, as described further below.

In some variations, the nucleic acid sequence of the nucleic acid labelled beads may further include a protein expression promoter sequence, as is known in the art. The promoter sequence may be any suitable promoter sequence, such as, but not limited to a T7 promoter sequence. The promoter sequence may assist the cell free expression system used in the methods described herein to more effectively express the protein encoded in the sequence variant portion of the nucleic acid labelled beads.

In some variations, the nucleic acid sequence of the nucleic acid labelled beads may further include an adapter sequence. The adapter sequence may be included within the nucleic acid sequence for massively parallel sequencing of the barcode nucleic acid sequence and/or the variant nucleic acid sequence (or further variant sequence). The adapter sequence may be any suitable adapter sequence as is generally known in the art.

The disposition of each variant (or further variant) nucleic sequence, barcode sequence, protein aggregation tag sequence (if present), protein expression promoter sequence (if present); and/or adapter sequence (if present) along the nucleic acid sequence of the nucleic acid labeled beads, from 5' terminus to 3' terminus may be selected as suitable and known in the art. For example, the promoter sequence may be located upstream (e.g., closer to the 5' terminus) of the variant nucleic acid sequence. The design of the disposition of each of these sequences can be chosen to ensure that functionality of the nucleic acid or the protein expressed therefrom is not adversely affected.

Protein aggregation beads. A protein aggregation bead may be made of any suitable material, such as polymer, metal, ceramic, glass, or any combination thereof. The protein aggregation bead may be magnetic or may not be magnetic. The protein aggregation bead includes a capture moiety configured to bind at least a portion of the protein expressed from the variant nucleic acid attached to beads of the test library. As used herein, "capture moiety" is a chemical or biological species, functionality, or motif that provides a recognition site for a portion of a protein, such as a peptide sequence, e.g., a protein tag. In some variations, the capture moiety of the protein aggregation bead may include a peptide sequence configured to bind to a protein tag which may comprise an epitope of the original protein sequence of interest. In some variations, the capture moiety of the protein aggregation bead may bind to an epitope tag (e.g., a protein tag) including, but not limited to FLAG-tag, E-tag, Myc-tag, T7, NE-tag, Spot-tag, V5-tag, VSV-tag, and the like, which are known in the art. The capture moiety may be an antibody which can specifically recognize and bind to the epitope tag, of which many are known in the art and commercially available such as a FLAG tag antibody (ThermoFisher Cat. No. 701629). In some variations, the protein aggregation bead includes a metal chelate species which can recognize a protein tag such as a His-tag (poly Histidine, which is chelated by a nickel or cobalt chelate. The nickel chelate may be Ni (II)-nitrilotriacetic acid (Ni-NTA). Another metal chelating tag is TC tag (which is bound by FLAsH or ReAsH biarsenical compounds). Any suitable protein tag may be used to capture expressed protein to the protein aggregation bead.

In the methods described herein, one or more protein aggregation beads may be introduced into an unswept region, e.g., an isolation region, for example, of a sequestration pen, to capture protein expressed from the variant nucleic acid linked to the nucleic acid labelled bead. In any of the methods, the protein aggregation beads including captured expressed protein may be exported selectively from the microfluidic device, after a phenotypic readout has been obtained. The exported protein aggregation bead including the expressed protein may be retested with the same phenotypic readout assay; may be tested in a different assay; or may be subjected to a different kind of analysis, such as mass spectrometric analysis of the expressed protein.

Cell-free expression system. Any suitable cell-free expression system may be used, according to its suitability for the protein of interest, to effect transcription/translation. Some nonlimiting examples include myTXTL® (Arbor biosciences, Sigma 70 Master Mix kit, Cat. No. 507024); Retic Lysate IVT kit for mammalian proteins (ThermoFisher Cat. No. AM1200); 1-Step Human Coupled IVT kit for mammalian proteins (ThermoFisher Cat. No. 88881); 1-Step Human High Yield IVT kit for mammalian proteins (ThermoFisher Cat. No. 88890); Expressway™ Maxi Cell-Free *E coli* Expression System (ThermoFisher Cat. No. K990100); *E. coli* S39 Extract system for linear templates (Promega Cat. No. L1030); *E coli* S30 T7 High-yield Protein Expression system, including T7 RNA polymerase (Promega Cat. No. L1110, L1115), and the like. One of skill can select an appropriate cell-free expression system from these or other commercially available systems for the particular protein of interest. Other components may also be included, such as functional fragments of endoplasmic reticulum, which may be used to help fold expressed proteins to the proper secondary structure needed for function of the protein of interest.

Phenotype Reporter. The phenotype reporter (also referred to herein as a phenotypic reporter) can be any type of reagent or object that indicates activity of a protein of interest. The phenotype reporter may include luminescent and/or fluorescent proteins to produce visually identifiable binding, function or enzymatic activity. In some cases, additional luminescent and/or fluorescent labels may be added to detect the amount of binding, function or enzymatic activity. In some embodiments, the phenotypic reporter includes a solution phase reagent providing a detectable result of protein function. In other embodiments, the phenotypic reporter is a micro-object, such as a micro-bead. In some embodiments, the phenotypic reporter is a reporter cell that is configured to report a function of the protein of interest. In some embodiments, the phenotypic reporter is a micro-object that includes binding affinity sites and provides a phenotypic readout. For example, the micro-object may include an enzymatic substrate that is configured to report out enzymatic activity of a protein of interest. In some examples, the phenotypic reporter is a bead including a substrate that may be used in an amylase assay. In some examples, the phenotypic reporter is a solution phase reagent, one nonlimiting example of which is EnzChek™ Ultra Amylase Assay (ThermoFisher Cat. No. E33651), which may be used in combination with a Ni-NTA magnetic bead-based assay using polyhistidine (His6) tagged affinity tags. Any suitable phenotypic reporter reagent/micro-object may be used, and may be selected by one of skill, based on the function of the original protein of interest, and the disclosure is not limited by the specific examples recited here. The phenotypic reporter may be used to detect activity of any type of protein using any type of assay. In some examples, the phenotypic reporter may be used to detect activity of enzymes, antibodies and/or protein fragments. The phenotypic reporter may be used to detect cytoplasmic function and/or membrane-bound function of a protein of interest. In some examples, the phenotypic reporter is used in assays to test a library of variant genes, to detect fitness differences of the variant nucleic acid sequences and/or to find genotype-phenotype links. In some examples, the phenotypic reporter is used to detect the evolution of a protein of interest. For example, the phenotypic reporter may be used in assays to investigate the evolution of gene or subgene structure for individual proteins of interest. The devices described herein may provide a controlled environment to control selection pressure when performing such assays.

Figure 9:
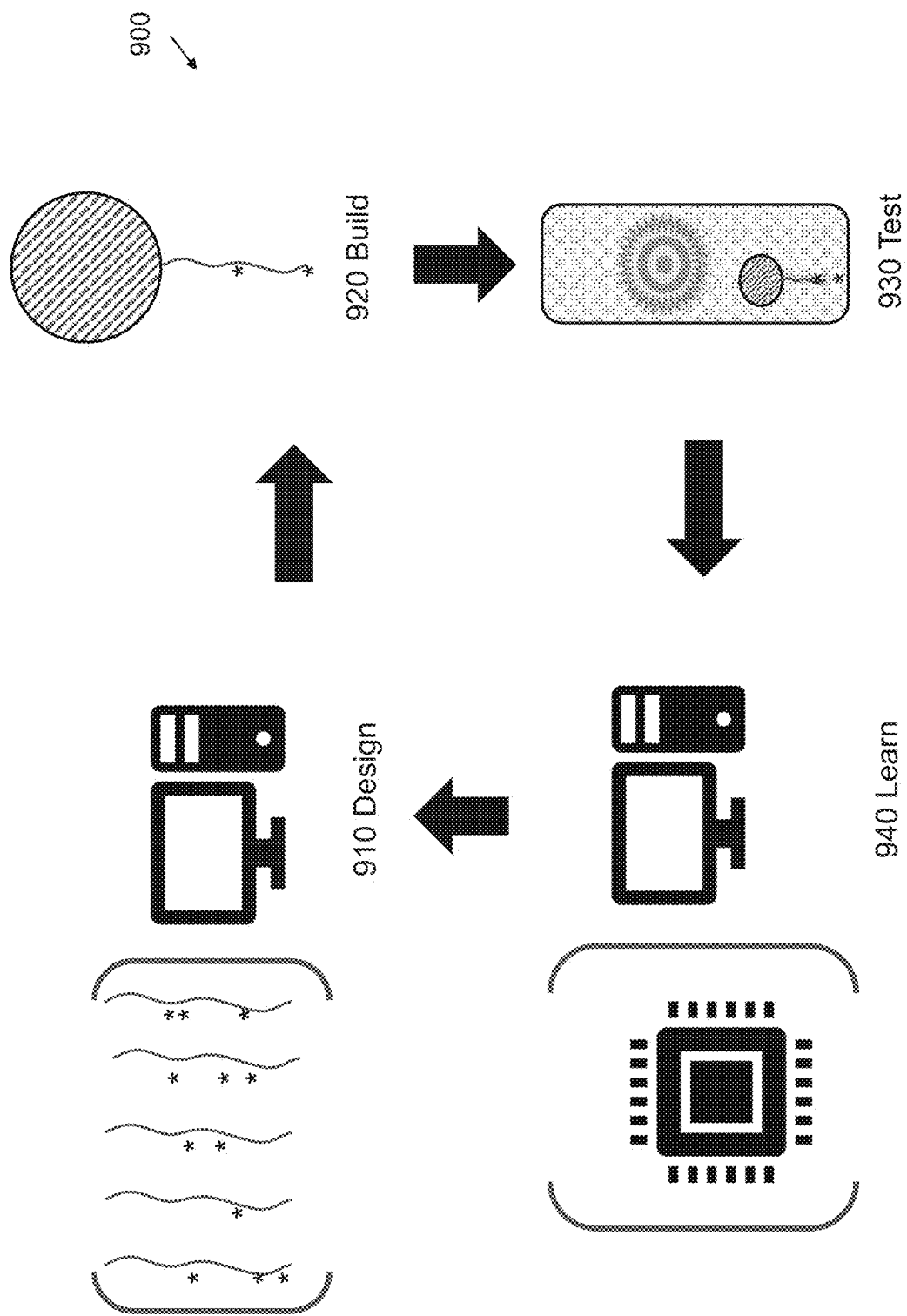
FIG. 9 illustrates an iterative process for rapidly evolving a protein sequence to identify an optimized sequence using the system as described herein.

Process for rapid evolution of protein sequence and function. A process for evolving a protein of interest—and, more particularly, a protein activity of a protein of interest—is provided, as shown in FIG. 9, the process including: disposing a first library of nucleic acid sequences within a microfluidic device, where the individual nucleic acid sequences of the first library are bound to corresponding beads. Each nucleic acid sequence of the first library includes one or more variations (e.g., single nucleotide replacements, insertions or deletions, or replacements, insertions of deletions of a series of adjacent nucleotides) from a nucleic acid sequence encoding an original protein sequence of interest (e.g., a naturally or non-naturally occurring protein, or fragment thereof, that optionally has a defined activity). The microfluidic device has a housing including a base and a microfluidic structure disposed on a surface of the base, where the base and the microfluidic structure define an interior chamber for holding a first liquid medium and micro-objects suspended therein. The method further includes introducing a phenotypic reporter into the microfluidic device and disposing it proximal to each nucleic acid sequence of the first library. Proximal, as used in this instance, includes a region that overlaps and/or is adjacent to the nucleic acid sequence or to the bead that contains the nucleic acid sequence. For example, "proximal" may be a point of disposition that is within about 300 microns of the nucleic acid sequence (e.g., within about 250 microns, about 200 microns, about 150 microns, about 100 microns or less). Proximal may also include disposing the phenotypic reporters providing the phenotypic readout in other locations such that the phenotype readout may be detected in the isolation region, the connection region and/or in the channel (e.g., adjacent to the opening of the sequestration pen into the channel. The phenotypic reporter may include a solution phase reagent and/or a plurality of micro-objects, and provides a phenotypic readout from the original protein sequence of interest. The phenotypic reporter may be any phenotypic reporter as described herein and may provide any suitable detectable signal as at least part of the phenotypic readout. The method includes introducing a reagent mixture into the microfluidic device and disposing it in proximity to each nucleic acid sequence of the first library, wherein the reagent mixture comprises one or more components which permit expression of a protein sequence from each nucleic acid sequence of the first library. The method includes expressing the protein sequence from each nucleic acid sequence of the first library; and further includes detecting the phenotypic readout from a region proximal to one or more nucleic acid sequences of the first library. The method includes identifying individual nucleic acid sequences from the first library having a corresponding proximal region with a desired phenotypic readout; and determining the sequence of the identified nucleic acid sequences of the first library.

In some embodiments, the phenotypic reporter may include a solution phase reagent providing a detectable signal when contacted by the original protein of interest (e.g., the reagent could be cleaved by the original protein of interest, and the cleavage could result in the emission of detectable light). In some variations, the phenotypic reporter may include micro-objects including binding sites for the original protein of interest, reporter cells configured to report a function of the original protein of interest, or micro-objects providing enzymatic substrates for an enzymatic activity of the protein of interest.

In some variations, correlating the individual nucleic acid sequences of the first library with the phenotypic readout detected in the corresponding proximal regions may then be performed; and a second library of nucleic acid sequences may be designed, where each nucleic acid sequence of the second library includes one or more variations from the nucleic acid sequence encoding the original protein sequence of interest, and are selected in light of the correlation. As referred to herein, "selected in light of the correlations" may include designing the nucleic acid sequences of the second library to include a new combination of variations present in the first library, or may include designing the nucleic acid sequences of the second library to include new variations that increase the diversity of the second library.

In some variations, each nucleic acid sequence of the first library is linked to a corresponding bead of a first plurality of beads. Each bead of the first plurality of beads may include a plurality of linked nucleic acids, each linked nucleic acid having the same variation of the nucleic acid sequence encoding the original protein sequence of interest.

In some variations, the process may further include designing the nucleic acid sequences of the first library to vary from the nucleic acid sequence encoding the original protein sequence of interest; synthesizing the nucleic acid sequences of the first library; and connecting each nucleic acid sequence of the first library to a corresponding bead of the first plurality of beads, thereby forming a first library of nucleic acid bearing beads.

Each bead of the plurality of beads forming the first (second or further) library may further include a corresponding distinct barcode. The distinct barcodes may include distinct nucleic acid sequences. The barcodes may be any suitable barcode as known in the art, and may have a nucleic acid sequence having a length as described herein.

In some variations, the process may further include reading the barcode (e.g., detecting or determining) of each bead of the first plurality of beads after disposing the first library of nucleic acid sequences in the microfluidic device, thereby identifying a location of each bead and its corresponding nucleic acid sequence within the microfluidic device. This may be performed at any suitable timepoint in the process, which may vary, depending on whether the barcode is detected visually or by determining its sequence by sequencing. In some embodiments, reading the barcode may be performed before detecting the phenotypic readout. In some embodiments, reading the barcode of each bead of the first plurality of beads may be performed after detecting the phenotypic readout. When reading the barcode includes determining the barcode by sequencing the nucleic acid sequence of the barcode, the nucleic acid labeled bead may be exported selectively out of the microfluidic device for further processing, in order to sequence the barcode.

In some variations, the reagent mixture may include a cell free protein expression reaction mixture. The cell free protein expression reaction mixture may be any suitable reaction mixture that can transcribe/translate the nucleic acids of the nucleic acid-labelled bead, as is known in the art, non-limiting examples of which are described herein. Introducing the reagent mixture may include flowing the reagent mixture into the flow path of a microfluidic device and permitting the reagent mixture to diffuse into the sequestration pens. Expressing the protein from the variant nucleic acid sequences of the library may be performed for any suitable period, as desired, to produce enough protein from the variant nucleic acid sequence. The period of expressing the protein may last from minutes to hours, and may be continued for 1 h, 2 h, 4 h, 6 h, 8 h, 12 h, 18 h, or longer.

In some variations, the process may further include disposing a plurality of protein aggregation beads within the microfluidic device, and disposing one or more protein aggregation beads of the plurality in proximity to each nucleic acid sequence of the first (second and further) library. One, two, five or more protein aggregation beads may be disposed in proximity to each nucleic acid sequence of the first library. The one or more protein aggregation beads may be disposed within about 300 microns, about 250 microns, about 200 microns, about 150 microns, about 100 microns or less. In proximity to the nucleic acid sequences may further include disposing the one or more protein aggregation beads in the connection region of the sequestration pen and/or in the channel(s). The protein aggregation beads of the plurality can specifically bind to (i) an epitope of the original protein sequence of interest or (ii) a protein tag encoded by each nucleic acid sequence of the first library so as to functionally include the protein sequence expressed therefrom. The protein tag may be any suitable protein tag known in the art, and exemplary protein tags classes are described herein. In various embodiments, the process may further include capturing the expressed protein from each nucleic acid sequence of the first library to the one or more protein aggregation beads disposed in proximity thereto. Capturing the expressed protein may be performed throughout the entire period of expressing the protein and may be continued for a period of time of about 30 min or 1 hr after protein expression has stopped, or capturing may end when the period of expressing the protein ends. The protein-labeled aggregation beads may be exposed to the phenotypic reporter, after sufficient protein has been captured to the protein-labeled aggregation beads.

In some embodiments, the process further includes flowing a flushing medium through the microfluidic device after expressing the protein sequence, thereby displacing the reagent mixture. The flushing medium may be a solution, such as a saline solution (e.g., PBS or the like), which is compatible with the phenotypic reporter. In some embodiments, the flushing medium may be the same or substantially similar to the first liquid medium. In some embodiments, flowing the flushing medium through the microfluidic device may be performed before detecting the phenotypic reporter. In some other embodiments, introducing the phenotypic reporter and disposing it in proximity to each nucleic acid of the first plurality may be performed after disposing the reagent mixture in proximity to each nucleic acid sequence of the first library.

In some variations, the microfluidic structure of the microfluidic device may include (i) a flow path for the first liquid medium; and (ii) a plurality of physical sequestration pens. Each sequestration pen of the plurality may include an enclosure; and a single opening to the flow path; where the enclosure encloses an interior space structured to hold a biological micro-object suspended in a second liquid medium. Each sequestration pen of the plurality may further include an inner wall extending from the opening into the enclosure. In some embodiments, the opening of each sequestration pen of the plurality of sequestration pens of the microfluidic device may be oriented such that no part is facing directly into the flow path, whereby, when the flow path contains a flow of the first liquid medium and the sequestration pen contains the second liquid medium, a direct flow of the first liquid medium into the second liquid medium in the interior space is impeded while diffusive mixing of the first liquid medium with the second liquid medium in the interior space is allowed. In some variations, the microfluidic device may further include a DEP configuration including: a first electrode; an electrode activation substrate; and a second electrode, wherein the first electrode is part of a first wall of the interior chamber and the electrode activation substrate and the second electrode are part of a second wall of the interior chamber, and wherein the electrode activation substrate comprises a photoconductive material, semiconductor integrated circuits, or phototransistors.

In some variations, disposing the first library of nucleic acid sequences within the microfluidic device may include introducing individual beads of the first plurality of beads into individual sequestration pens of the plurality of sequestration pens. In some embodiments, no more than one bead of the first plurality of beads may be introduced into each sequestration pen of the plurality of sequestration pens.

In some variations, introducing the phenotypic reporter into the microfluidic device may include introducing one or more micro-objects of the plurality of micro-objects into individual sequestration pens containing a nucleic acid sequence of the first library of nucleic acid sequences.

In various embodiments of the process, the protein of interest may include an enzyme. In other embodiments, the protein of interest may include a domain which binds to a cell surface marker. The cell surface marker may be a cell surface receptor (e.g., a receptor involved in intercellular signaling) or a glycoprotein. The cell surface receptor may be a protein, such as a glycoprotein or a protein complex.

In some embodiments, the protein of interest may include an antibody. The antibody may be a single chain antibody, e.g., having no disulfide bonds; a nanobody, e.g., a heavy chain antibody from a camelid species; a single chain variable fragment; and/or may have no sugar modifications.

In some variations, correlating the individual nucleic acid sequences of the first library with the phenotypic readout detected in the corresponding proximal regions may be performed by a first computer component configured to identify a function of the expressed protein from the identified nucleic acid sequences that is more desirable than the function of the original protein of interest. In some embodiments, designing the second library of nucleic acid sequences may be performed by a second computer component, based on the correlation of the expressed protein function with the nucleic acid sequences of the first library of nucleic acid sequences. In some variations, the first computer component may be the same as the second computer component. In some embodiments, the first computer component may employ a machine learning algorithm to perform the correlation. In some variations, the second computer component may employ a machine learning algorithm to design the second library of nucleic acid sequences.

The first (and/or the second) library of nucleic acid sequences may be synthesized by a parallel nucleic acid synthesizer. In some embodiments, the parallel nucleic acids synthesizer may be a massively parallel nucleic acids synthesizer. In some embodiments, the parallel nucleic acids synthesizer may be configured to assemble a plurality of short-length synthesized nucleic acids into a longer conjoined nucleic acid. The plurality of short-length synthesized nucleic acids to be assembled may each have a length (e.g., number of nucleotides in the short-length synthesized nucleic acids) of less than about 200 nucleotides, less than about 150 nucleotides, less than about 100 nucleotides, or less than about 50 nucleotides. In some embodiments, the parallel nucleic acids synthesizer configured to assemble longer conjoined nucleic acids may be further configured to assemble a plurality of longer conjoined nucleic acids in parallel.

In some variations of the process, each of the second library of nucleic acid sequences may be linked to a corresponding bead to form a second library of nucleic acid bearing beads. The second library of nucleic acids sequences may be subjected to any processes described herein, in any combination, to provide a second set of correlated phenotypic readouts with nucleic acid sequences of the second library. In some embodiments, a further library of nucleic acid sequences may be designed and synthesized. The nucleic acid sequences of the further library of nucleic acid sequences may be linked to corresponding beads to form a further library of nucleic acid bearing beads. The further library of nucleic acids sequences may be subjected to any processes described herein, in any combination, to provide a further set of correlated phenotypic readouts with nucleic acid sequences of the second library.

In some variations, the first library of nucleic acid sequences may include variations within a sub-region of the nucleic acid sequence encoding the original protein of interest. The sub-region of the nucleic acid sequence encoding the original protein of interest may encode for a region of the protein producing a function of interest. In some embodiments, the sub-region may encode for an enzymatic active site or a binding site (e.g., an antigen recognition site or a protein-protein binding site) of the original protein of interest. In some variations, the first library of nucleic acid sequences may include variations throughout the length of the nucleic acid sequence encoding the original protein of interest.

In some variations, the second library of nucleic acid sequences and/or the further library of nucleic acid sequences may include variations within a sub-region of the nucleic acid sequence encoding the original protein of interest. The sub-region of the nucleic acid sequence encoding the original protein of interest may encode for a region of the protein producing a function of interest. The sub-region may encode for an enzymatic active site or a binding site (e.g., an antigen recognition site or a protein-protein binding site) of the original protein of interest. In some other embodiments, the second library of nucleic acid sequences and/or the further library of nucleic acid sequences may include variations throughout the length of the nucleic acid sequence encoding the original protein of interest.

However the method is not limited to being performed within a sequestration pen having an isolation region, but may be performed within any suitable isolation region of a microfluidic device. That is, any unswept region of a microfluidic device may be used to hold a nucleic acid labeled bead. Further, while this process has been described as being performed in a microfluidic device, it may alternatively be performed in other formats, such as within a microarray or a plurality of wells of a microwell plate, and the disclosure is not so limited.

Kits. A kit for rapid evolution of a protein of interest is provided, the kit including: a microfluidic device, wherein the microfluidic device includes: a housing including a base and a microfluidic structure disposed on a surface of the base, where the base and the microfluidic structure define an interior chamber for holding a first liquid medium and micro-objects suspended therein; and a phenotypic reporter. In some variations, the phenotypic reporter may include a solution phase reagent providing a detectable signal when contacted by the original protein of interest (e.g., the reagent could be cleaved by the original protein of interest, and the cleavage could result in the emission of detectable light). In some variations, the phenotypic reporter may include a plurality of micro-objects, each micro-object configured to provide a phenotypic readout from the original protein sequence of interest. The micro-objects of the plurality of micro-objects may include binding sites for the original protein of interest, include enzymatic substrates for an enzymatic activity of the original protein of interest, and/or are reporter cells configured to report a function of the original protein of interest.

In some variations, the microfluidic structure of the microfluidic device may include (i) a flow path for the first liquid medium; and (ii) a plurality of physical sequestration pens. In some embodiments, each sequestration pen of the plurality of sequestration pens may include an enclosure; and a single opening to the flow path; wherein the enclosure encloses an interior space structured to hold a micro-object suspended in a second liquid medium. In some embodiments, the sequestration pen may include an inner wall extending from the opening into the enclosure. In some variations, the opening of each sequestration pen of the plurality of sequestration pens of the microfluidic device may be oriented such that no part is facing directly into the flow path of the channel, whereby, when the channel contains a flow of the first liquid medium and the sequestration pen contains the second liquid medium, a direct flow of the first liquid medium into the second liquid medium in the interior space is impeded while diffusive mixing of the first liquid medium with the second liquid medium in the interior space is allowed. In some variations, the microfluidic device may further include a DEP configuration including: a first electrode; an electrode activation substrate; and a second electrode, wherein the first electrode is part of a first wall of the interior chamber and the electrode activation substrate and the second electrode are part of a second wall of the interior chamber, and where the electrode activation substrate comprises a photoconductive material, semiconductor integrated circuits, or phototransistors.

In some variations, the kit may further include a reagent mixture for expressing protein from a nucleic acid sequence in vitro. The reagent mixture may be a cell free protein expression mixture.

In some variations, the kit may further include a plurality of beads, each configured to bind to a nucleic acid sequence. In some embodiments, each bead of the plurality of beads may include a unique barcode. In some variations, the unique barcode may be a unique nucleic acid sequence.

In some variations, the kit may further include a plurality of protein aggregation beads. In some embodiments, each of the plurality of protein aggregation beads specifically bind an epitope of the original protein sequence of interest or a protein tag.

In some variations, the kit may further include machine readable instructions for a computer component or computer components. In some embodiments, the machine readable instructions may enable the computer component or computer components to correlate individual nucleic acid sequences of a library of nucleic acid sequences with phenotypes associated with the individual nucleic acid sequences; and/or design a library of nucleic acid sequences, wherein each nucleic acid sequence of the library includes one or more variations from a nucleic acid sequence encoding an original protein sequence of interest and, optionally, wherein the library design is based upon a correlation between a plurality of individual nucleic acid sequences and phenotypes associated with the individual nucleic acid sequences.

Microfluidic device/system feature cross-applicability. It should be appreciated that various features of microfluidic devices, systems, and motive technologies described herein may be combinable or interchangeable. For example, features described herein with reference to the microfluidic device 100, 175, 200, 300, 320, 400, 450, 520 and system attributes as described in FIGS. 1A-5B may be combinable or interchangeable.

Microfluidic devices. FIG. 1A illustrates an example of a microfluidic device 100. A perspective view of the microfluidic device 100 is shown having a partial cut-away of its cover 110 to provide a partial view into the microfluidic device 100. The microfluidic device 100 generally comprises a microfluidic circuit 120 comprising a flow path 106 through which a fluidic medium 180 can flow, optionally carrying one or more micro-objects (not shown) into and/or through the microfluidic circuit 120.

As generally illustrated in FIG. 1A, the microfluidic circuit 120 is defined by an enclosure 102. Although the enclosure 102 can be physically structured in different configurations, in the example shown in FIG. 1A the enclosure 102 is depicted as comprising a support structure 104 (e.g., a base), a microfluidic circuit structure 108, and a cover 110. The support structure 104, microfluidic circuit structure 108, and cover 110 can be attached to each other.

For example, the microfluidic circuit structure 108 can be disposed on an inner surface 109 of the support structure 104, and the cover 110 can be disposed over the microfluidic circuit structure 108. Together with the support structure 104 and cover 110, the microfluidic circuit structure 108 can define the elements of the microfluidic circuit 120, forming a three-layer structure.

The support structure 104 can be at the bottom and the cover 110 at the top of the microfluidic circuit 120 as illustrated in FIG. 1A. Alternatively, the support structure 104 and the cover 110 can be configured in other orientations. For example, the support structure 104 can be at the top and the cover 110 at the bottom of the microfluidic circuit 120. Regardless, there can be one or more ports 107 each comprising a passage into or out of the enclosure 102. Examples of a passage include a valve, a gate, a pass-through hole, or the like. As illustrated, port 107 is a pass-through hole created by a gap in the microfluidic circuit structure 108. However, the port 107 can be situated in other components of the enclosure 102, such as the cover 110. Only one port 107 is illustrated in FIG. 1A but the microfluidic circuit 120 can have two or more ports 107. For example, there can be a first port 107 that functions as an inlet for fluid entering the microfluidic circuit 120, and there can be a second port 107 that functions as an outlet for fluid exiting the microfluidic circuit 120. Whether a port 107 function as an inlet or an outlet can depend upon the direction that fluid flows through flow path 106.

The support structure 104 can comprise one or more electrodes (not shown) and a substrate or a plurality of interconnected substrates. For example, the support structure 104 can comprise one or more semiconductor substrates, each of which is electrically connected to an electrode (e.g., all or a subset of the semiconductor substrates can be electrically connected to a single electrode). The support structure 104 can further comprise a printed circuit board assembly ("PCBA"). For example, the semiconductor substrate(s) can be mounted on a PCBA.

The microfluidic circuit structure 108 can define circuit elements of the microfluidic circuit 120. Such circuit elements can comprise spaces or regions that can be fluidly interconnected when microfluidic circuit 120 is filled with fluid, such as flow regions (which may include or be one or more flow channels), chambers (which class of circuit elements may also include sub-classes including sequestration pens), traps, and the like. Circuit elements can also include barriers, and the like. In the microfluidic circuit 120 illustrated in FIG. 1A, the microfluidic circuit structure 108 comprises a frame 114 and a microfluidic circuit material 116. The frame 114 can partially or completely enclose the microfluidic circuit material 116. The frame 114 can be, for example, a relatively rigid structure substantially surrounding the microfluidic circuit material 116. For example, the frame 114 can comprise a metal material. However, the microfluidic circuit structure need not include a frame 114. For example, the microfluidic circuit structure can consist of (or consist essentially of) the microfluidic circuit material 116.

The microfluidic circuit material 116 can be patterned with cavities or the like to define the circuit elements and interconnections of the microfluidic circuit 120, such as chambers, pens and microfluidic channels. The microfluidic circuit material 116 can comprise a flexible material, such as a flexible polymer (e.g. rubber, plastic, elastomer, silicone, polydimethylsiloxane ("PDMS"), or the like), which can be gas permeable. Other examples of materials that can form the microfluidic circuit material 116 include molded glass, an etchable material such as silicone (e.g. photo-patternable silicone or "PPS"), photo-resist (e.g., SU8), or the like. In some embodiments, such materials—and thus the microfluidic circuit material 116—can be rigid and/or substantially impermeable to gas. Regardless, microfluidic circuit material 116 can be disposed on the support structure 104 and inside the frame 114.

The microfluidic circuit 120 can include a flow region in which one or more chambers can be disposed and/or fluidically connected thereto. A chamber can have one or more openings fluidically connecting the chamber with one or more flow regions. In some embodiments, a flow region comprises or corresponds to a microfluidic channel 122. Although a single microfluidic circuit 120 is illustrated in FIG. 1A, suitable microfluidic devices can include a plurality (e.g., 2 or 3) of such microfluidic circuits. In some embodiments, the microfluidic device 100 can be configured to be a nanofluidic device. As illustrated in FIG. 1A, the microfluidic circuit 120 may include a plurality of microfluidic sequestration pens 124, 126, 128, and 130, where each sequestration pens may have one or more openings. In some embodiments of sequestration pens, a sequestration pen may have only a single opening in fluidic communication with the flow path 106. In some other embodiments, a sequestration pen may have more than one opening in fluidic communication with the flow path 106, e.g., n number of openings, but with n-1 openings that are valved, such that all but one opening is closable. When all the valved openings are closed, the sequestration pen limits exchange of materials from the flow region into the sequestration pen to occur only by diffusion. In some embodiments, the sequestration pens comprise various features and structures (e.g., isolation regions) that have been optimized for retaining microobjects within the sequestration pen (and therefore within a microfluidic device such as microfluidic device 100) even when a medium 180 is flowing through the flow path 106.

The cover 110 can be an integral part of the frame 114 and/or the microfluidic circuit material 116. Alternatively, the cover 110 can be a structurally distinct element, as illustrated in FIG. 1A. The cover 110 can comprise the same or different materials than the frame 114 and/or the microfluidic circuit material 116. In some embodiments, the cover 110 can be an integral part of the microfluidic circuit material 116. Similarly, the support structure 104 can be a separate structure from the frame 114 or microfluidic circuit material 116 as illustrated, or an integral part of the frame 114 or microfluidic circuit material 116. Likewise, the frame 114 and microfluidic circuit material 116 can be separate structures as shown in FIG. 1A or integral portions of the same structure. Regardless of the various possible integrations, the microfluidic device can retain a three-layer structure that includes a base layer and a cover layer that sandwich a middle layer in which the microfluidic circuit 120 is located.

In some embodiments, the cover 110 can comprise a rigid material. The rigid material may be glass or a material with similar properties. In some embodiments, the cover 110 can comprise a deformable material. The deformable material can be a polymer, such as PDMS. In some embodiments, the cover 110 can comprise both rigid and deformable materials. For example, one or more portions of cover 110 (e.g., one or more portions positioned over sequestration pens 124, 126, 128, 130) can comprise a deformable material that interfaces with rigid materials of the cover 110. Microfluidic devices having covers that include both rigid and deformable materials have been described, for example, in U.S. Pat. No. 10,058,865 (Breinlinger et al.), the contents of which are incorporated herein by reference. In some embodiments, the cover 110 can further include one or more electrodes. The one or more electrodes can comprise a conductive oxide, such as indium-tin-oxide (ITO), which may be coated on glass or a similarly insulating material. Alternatively, the one or more electrodes can be flexible electrodes, such as single-walled nanotubes, multi-walled nanotubes, nanowires, clusters of electrically conductive nanoparticles, or combinations thereof, embedded in a deformable material, such as a polymer (e.g., PDMS). Flexible electrodes that can be used in microfluidic devices have been described, for example, in U.S. Pat. No. 9,227,200 (Chiou et al.), the contents of which are incorporated herein by reference. In some embodiments, the cover 110 and/or the support structure 104 can be transparent to light. The cover 110 may also include at least one material that is gas permeable (e.g., PDMS or PPS).

In the example shown in FIG. 1A, the microfluidic circuit 120 is illustrated as comprising a microfluidic channel 122 and sequestration pens 124, 126, 128, 130. Each pen comprises an opening to channel 122, but otherwise is enclosed such that the pens can substantially isolate micro-objects inside the pen from fluidic medium 180 and/or micro-objects in the flow path 106 of channel 122 or in other pens. The walls of the sequestration pen extend from the inner surface 109 of the base to the inside surface of the cover 110 to provide enclosure. The opening of the sequestration pen to the microfluidic channel 122 is oriented at an angle to the flow 106 of fluidic medium 180 such that flow 106 is not directed into the pens. The vector of bulk fluid flow in channel 122 may be tangential or parallel to the plane of the opening of the sequestration pen, and is not directed into the opening of the pen. In some instances, pens 124, 126, 128, 130 are configured to physically isolate one or more micro-objects within the microfluidic circuit 120. Sequestration pens in accordance with the present disclosure can comprise various shapes, surfaces and features that are optimized for use with DEP, OET, OEW, fluid flow, magnetic forces, centripetal, and/or gravitational forces, as will be discussed and shown in detail below.

The microfluidic circuit 120 may comprise any number of microfluidic sequestration pens. Although five sequestration pens are shown, microfluidic circuit 120 may have fewer or more sequestration pens. As shown, microfluidic sequestration pens 124, 126, 128, and 130 of microfluidic circuit 120 each comprise differing features and shapes which may provide one or more benefits useful for maintaining, isolating, assaying or culturing biological micro-objects. In some embodiments, the microfluidic circuit 120 comprises a plurality of identical microfluidic sequestration pens.

Figure 1B:
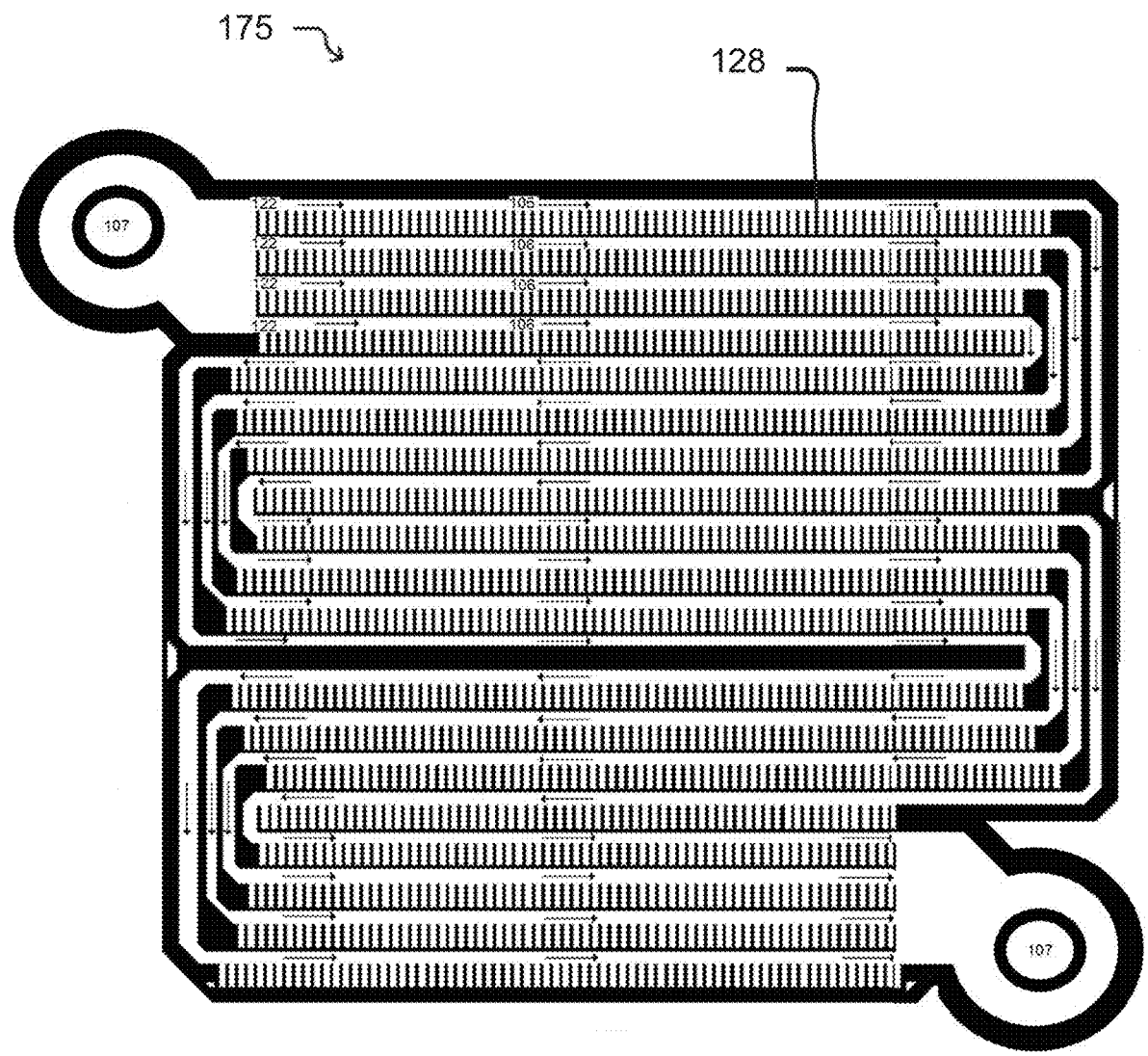
FIG. 1B illustrates a microfluidic device with sequestration pens according to an embodiment of the disclosure.

In the embodiment illustrated in FIG. 1A, a single flow path 106 containing a single channel 122 is shown. However, other embodiments may contain multiple channels 122 within a single flow path 106, as shown in FIG. 1B. The microfluidic circuit 120 further comprises an inlet valve or port 107 in fluid communication with the flow path 106, whereby fluidic medium 180 can access the flow path 106 (and channel 122). In some instances, the flow path 106 comprises a substantially straight path. In other instances, the flow path 106 is arranged in a non-linear or winding manner, such as a zigzag pattern, whereby the flow path 106 travels across the microfluidic device 100 two or more times, e.g., in alternating directions. The flow in the flow path 106 may proceed from inlet to outlet or may be reversed and proceed from outlet to inlet.

One example of a multi-channel device, microfluidic device 175, is shown in FIG. 1B, which may be like microfluidic device 100 in other respects. Microfluidic device 175 and its constituent circuit elements (e.g., channels 122 and sequestration pens 128) may have any of the dimensions discussed herein. The microfluidic circuit illustrated in FIG. 1B has two inlet/outlet ports 107 and a flow path 106 containing four distinct channels 122. The number of channels into which the microfluidic circuit is sub-divided may be chosen to reduce fluidic resistance. For example, the microfluidic circuit may include 1, 2, 3, 4, 5, 6, 7, 8, 9, 10, or more channels to provide a selected range of fluidic resistance. Microfluidic device 175 further comprises a plurality of sequestration pens opening off of each channel 122, where each of the sequestration pens is similar to sequestration pen 128 of FIG. 1A, and may have any of the dimensions or functions of any sequestration pen as described herein. However, the sequestration pens of microfluidic device 175 can have different shapes, such as any of the shapes of sequestration pens 124, 126, or 130 of FIG. 1A or as described anywhere else herein. Moreover, microfluidic device 175 can include sequestration pens having a mixture of different shapes. In some instances, a plurality of sequestration pens is configured (e.g., relative to a channel 122) such that the sequestration pens can be loaded with target micro-objects in parallel.

Returning to FIG. 1A, microfluidic circuit 120 further may include one or more optional micro-object traps 132. The optional traps 132 may be formed in a wall forming the boundary of a channel 122, and may be positioned opposite an opening of one or more of the microfluidic sequestration pens 124, 126, 128, 130. The optional traps 132 may be configured to receive or capture a single micro-object from the flow path 106, or may be configured to receive or capture a plurality of micro-objects from the flow path 106. In some instances, the optional traps 132 comprise a volume approximately equal to the volume of a single target micro-object.

Sequestration pens. The microfluidic devices described herein may include one or more sequestration pens, where each sequestration pen is suitable for holding one or more micro-objects (e.g., biological cells, or groups of cells that are associated together). The sequestration pens may be disposed within and open to a flow region, which in some embodiments is a microfluidic channel. Each of the sequestration pens can have one or more openings for fluidic communication to one or more microfluidic channels. In some embodiments, a sequestration pen may have only one opening to a microfluidic channel.

Figure 2A:
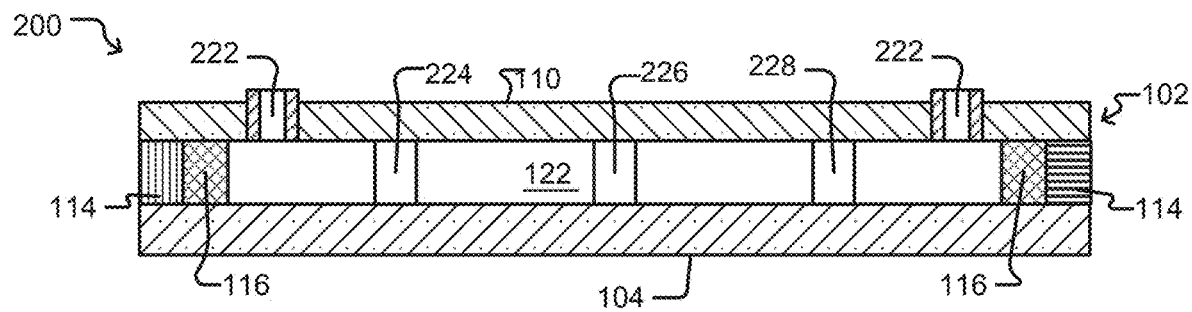
FIGS. 2A-2B illustrate a microfluidic device having sequestration pens according to some embodiments of the disclosure.
Figure 2B:
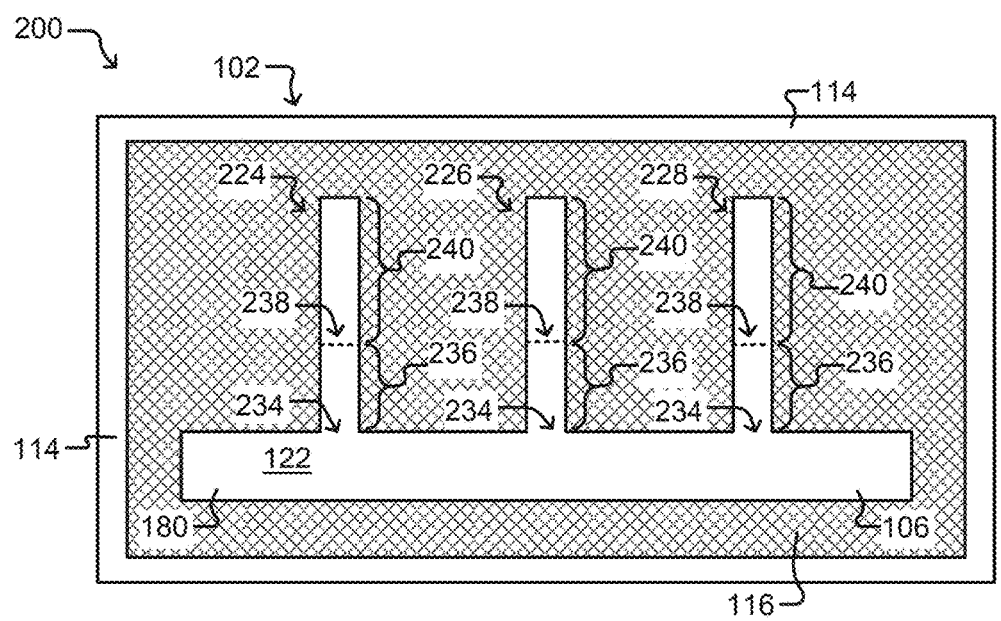
Figure 2C:
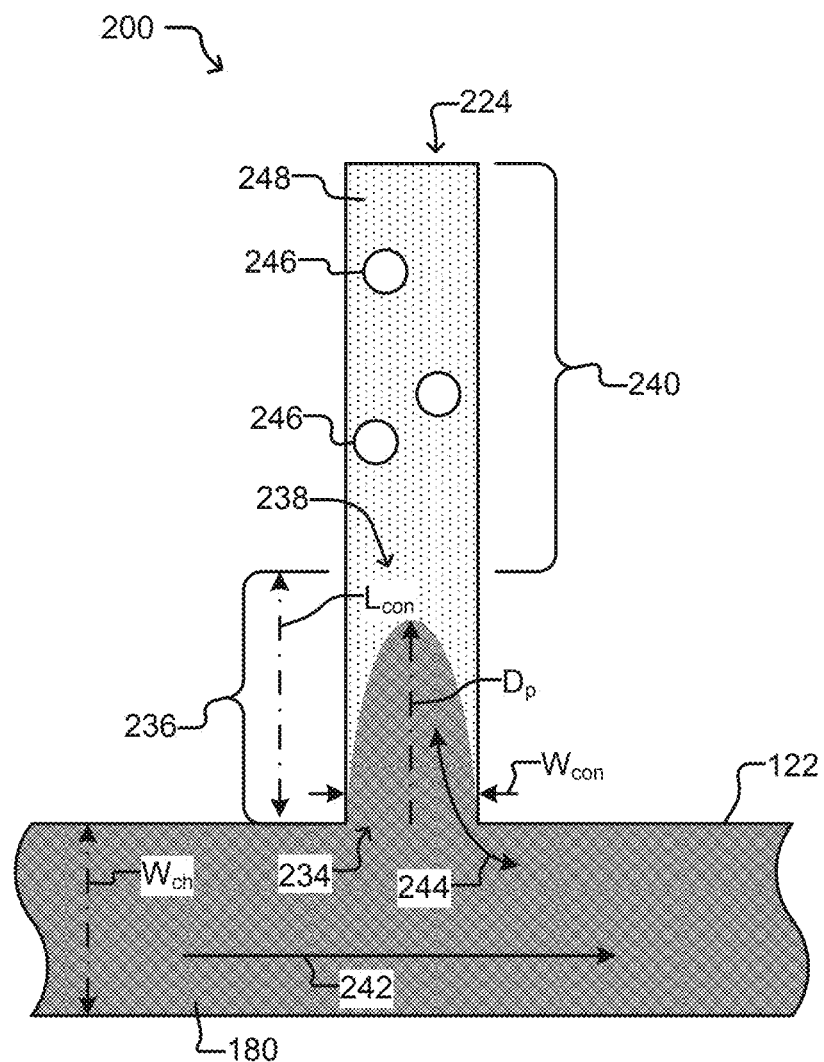
FIG. 2C illustrates a sequestration pen of a microfluidic device according to some embodiments of the disclosure.

FIGS. 2A-2C show sequestration pens 224, 226, and 228 of a microfluidic device 200, which may be like sequestration pen 128 of FIG. 1A. Each sequestration pen 224, 226, and 228 can comprise an isolation region 240 and a connection region 236 fluidically connecting the isolation region 240 to a flow region, which may, in some embodiments include a microfluidic channel, such as channel 122. The connection region 236 can comprise a proximal opening 234 to the flow region (e.g., microfluidic channel 122) and a distal opening 238 to the isolation region 240. The connection region 236 can be configured so that the maximum penetration depth of a flow of a fluidic medium (not shown) flowing in the microfluidic channel 122 past the sequestration pen 224, 226, and 228 does not extend into the isolation region 240, as discussed below for FIG. 2C. In some embodiments, streamlines from the flow in the microfluidic channel do not enter the isolation region. Thus, due to the connection region 236, a micro-object (not shown) or other material (not shown) disposed in the isolation region 240 of a sequestration pen 224, 226, and 228 can be isolated from, and not substantially affected by, a flow of fluidic medium 180 in the microfluidic channel 122.

The sequestration pens 224, 226, and 228 of FIGS. 2A-2C each have a single opening which opens directly to the microfluidic channel 122. The opening of the sequestration pen may open laterally from the microfluidic channel 122, as shown in FIG. 2A, which depicts a vertical cross-section of microfluidic device 200. FIG. 2B shows a horizontal cross-section of microfluidic device 200. An electrode activation substrate 206 can underlie both the microfluidic channel 122 and the sequestration pens 224, 226, and 228. The upper surface of the electrode activation substrate 206 within an enclosure of a sequestration pen, forming the floor of the sequestration pen, can be disposed at the same level or substantially the same level of the upper surface of the electrode activation substrate 206 within the microfluidic channel 122 (or flow region if a channel is not present), forming the floor of the flow channel (or flow region, respectively) of the microfluidic device. The electrode activation substrate 206 may be featureless or may have an irregular or patterned surface that varies from its highest elevation to its lowest depression by less than about 3 micrometers (microns), 2.5 microns, 2 microns, 1.5 microns, 1 micron, 0.9 microns, 0.5 microns, 0.4 microns, 0.2 microns, 0.1 microns or less. The variation of elevation in the upper surface of the substrate across both the microfluidic channel 122 (or flow region) and sequestration pens may be equal to or less than about 10%, 7%, 5%, 3%, 2%, 1%. 0.9%, 0.8%, 0.5%, 0.3% or 0.1% of the height of the walls of the sequestration pen. Alternatively, the variation of elevation in the upper surface of the substrate across both the microfluidic channel 122 (or flow region) and sequestration pens may be equal to or less than about 2%, 1%. 0.9%, 0.8%, 0.5%, 0.3%, 0.2%, or 0.1% of the height of the substrate. While described in detail for the microfluidic device 200, this may also apply to any of the microfluidic devices described herein.

The microfluidic channel 122 and connection region 236 can be examples of swept regions, and the isolation regions 240 of the sequestration pens 224, 226, and 228 can be examples of unswept regions. Sequestration pens like 224, 226, 228 have isolation regions wherein each isolation region has only one opening, which opens to the connection region of the sequestration pen. Fluidic media exchange in and out of the isolation region so configured can be limited to occurring substantially only by diffusion. As noted, the microfluidic channel 122 and sequestration pens 224, 226, and 228 can be configured to contain one or more fluidic media 180. In the example shown in FIGS. 2A-2B, ports 222 are connected to the microfluidic channel 122 and allow the fluidic medium 180 to be introduced into or removed from the microfluidic device 200. Prior to introduction of the fluidic medium 180, the microfluidic device may be primed with a gas such as carbon dioxide gas. Once the microfluidic device 200 contains the fluidic medium 180, the flow 242 (see FIG. 2C) of fluidic medium 180 in the microfluidic channel 122 can be selectively generated and stopped. For example, as shown, the ports 222 can be disposed at different locations (e.g., opposite ends) of the flow region (microfluidic channel 122), and a flow 242 of the fluidic medium can be created from one port 222 functioning as an inlet to another port 222 functioning as an outlet.

FIG. 2C illustrates a detailed view of an example of a sequestration pen 224, which may contain one or more micro-objects 246, according to some embodiments. The flow 242 of fluidic medium 180 in the microfluidic channel 122 past the proximal opening 234 of the connection region 236 of sequestration pen 224 can cause a secondary flow 244 of the fluidic medium 180 into and out of the sequestration pen 224. To sequester the micro-objects 246 in the isolation region 240 of the sequestration pen 224 from the secondary flow 244, the length $L_{con}$ of the connection region 236 of the sequestration pen 224 (i.e., from the proximal opening 234 to the distal opening 238) should be greater than the penetration depth $D_p$ of the secondary flow 244 into the connection region 236. The penetration depth $D_p$ depends upon a number of factors, including the shape of the microfluidic channel 122, which may be defined by a width $W_{con}$ of the connection region 236 at the proximal opening 234; a width $W_{ch}$ of the microfluidic channel 122 at the proximal opening 234; a height $H_{ch}$ of the channel 122 at the proximal opening 234; and the width of the distal opening 238 of the connection region 236. Of these factors, the width $W_{con}$ of the connection region 236 at the proximal opening 234 and the height $H_{ch}$ of the channel 122 at the proximal opening 234 tend to be the most significant. In addition, the penetration depth $D_p$ can be influenced by the velocity of the fluidic medium 180 in the channel 122 and the viscosity of fluidic medium 180. However, these factors (i.e., velocity and viscosity) can vary widely without dramatic changes in penetration depth $D_p$. For example, for a microfluidic chip 200 having a width $W_{con}$ of the connection region 236 at the proximal opening 234 of about 50 microns, a height $H_{ch}$ of the channel 122 at the proximal opening 122 of about 40 microns, and a width $W_{ch}$ of the microfluidic channel 122 at the proximal opening 122 of about 100 microns to about 150 microns, the penetration depth $D_p$ of the secondary flow 244 ranges from less than 1.0 times $W_{con}$ (i.e., less than 50 microns) at a flow rate of 0.1 microliters/see to about 2.0 times $W_{con}$ (i.e., about 100 microns) at a flow rate of 20 microliters/see, which represents an increase in $D_p$ of only about 2.5-fold over a 200-fold increase in the velocity of the fluidic medium 180.

In some embodiments, the walls of the microfluidic channel 122 and sequestration pen 224, 226, or 228 can be oriented as follows with respect to the vector of the flow 242 of fluidic medium 180 in the microfluidic channel 122: the microfluidic channel width $W_{ch}$ (or cross-sectional area of the microfluidic channel 122) can be substantially perpendicular to the flow 242 of medium 180; the width $W_{con}$ (or cross-sectional area) of the connection region 236 at opening 234 can be substantially parallel to the flow 242 of medium 180 in the microfluidic channel 122; and/or the length $L_{con}$ of the connection region can be substantially perpendicular to the flow 242 of medium 180 in the microfluidic channel 122. The foregoing are examples only, and the relative position of the microfluidic channel 122 and sequestration pens 224, 226 and 228 can be in other orientations with respect to each other.

In some embodiments, for a given microfluidic device, the configurations of the microfluidic channel 122 and the opening 234 may be fixed, whereas the rate of flow 242 of fluidic medium 180 in the microfluidic channel 122 may be variable. Accordingly, for each sequestration pen 224, a maximal velocity $V_{max}$ for the flow 242 of fluidic medium 180 in channel 122 may be identified that ensures that the penetration depth $D_p$ of the secondary flow 244 does not exceed the length $L_{con}$ of the connection region 236. When $V_{max}$ is not exceeded, the resulting secondary flow 244 can be wholly contained within the connection region 236 and does not enter the isolation region 240. Thus, the flow 242 of fluidic medium 180 in the microfluidic channel 122 (swept region) is prevented from drawing micro-objects 246 out of the isolation region 240, which is an unswept region of the microfluidic circuit, resulting in the micro-objects 246 being retained within the isolation region 240. Accordingly, selection of microfluidic circuit element dimensions and further selection of the operating parameters (e.g., velocity of fluidic medium 180) can prevent contamination of the isolation region 240 of sequestration pen 224 by materials from the microfluidic channel 122 or another sequestration pen 226 or 228. It should be noted, however, that for many microfluidic chip configurations, there is no need to worry about $V_{max}$ per se, because the chip will break from the pressure associated with flowing fluidic medium 180 at high velocity through the chip before $V_{max}$ can be achieved.

Components (not shown) in the first fluidic medium 180 in the microfluidic channel 122 can mix with the second fluidic medium 248 in the isolation region 240 substantially only by diffusion of components of the first medium 180 from the microfluidic channel 122 through the connection region 236 and into the second fluidic medium 248 in the isolation region 240. Similarly, components (not shown) of the second medium 248 in the isolation region 240 can mix with the first medium 180 in the microfluidic channel 122 substantially only by diffusion of components of the second medium 248 from the isolation region 240 through the connection region 236 and into the first medium 180 in the microfluidic channel 122. In some embodiments, the extent of fluidic medium exchange between the isolation region of a sequestration pen and the flow region by diffusion is greater than about 90%, 91%, 92%, 93%, 94% 95%, 96%, 97%, 98%, or greater than about 99% of fluidic exchange.

In some embodiments, the first medium 180 can be the same medium or a different medium than the second medium 248. In some embodiments, the first medium 180 and the second medium 248 can start out being the same, then become different (e.g., through conditioning of the second medium 248 by one or more cells in the isolation region 240, or by changing the medium 180 flowing through the microfluidic channel 122).

As illustrated in FIG. 2C, the width $W_{con}$ of the connection region 236 can be uniform from the proximal opening 234 to the distal opening 238. The width $W_{con}$ of the connection region 236 at the distal opening 238 can be any of the values identified herein for the width $W_{con}$ of the connection region 236 at the proximal opening 234. In some embodiments, the width of the isolation region 240 at the distal opening 238 can be substantially the same as the width $W_{con}$ of the connection region 236 at the proximal opening 234. Alternatively, the width $W_{con}$ of the connection region 236 at the distal opening 238 can be different (e.g., larger or smaller) than the width $W_{con}$ of the connection region 236 at the proximal opening 234. In some embodiments, the width $W_{con}$ of the connection region 236 may be narrowed or widened between the proximal opening 234 and distal opening 238. For example, the connection region 236 may be narrowed or widened between the proximal opening and the distal opening, using a variety of different geometries (e.g., chamfering the connection region, beveling the connection region). Further, any part or subpart of the connection region 236 may be narrowed or widened (e.g., a portion of the connection region adjacent to the proximal opening 234).

Figure 3:
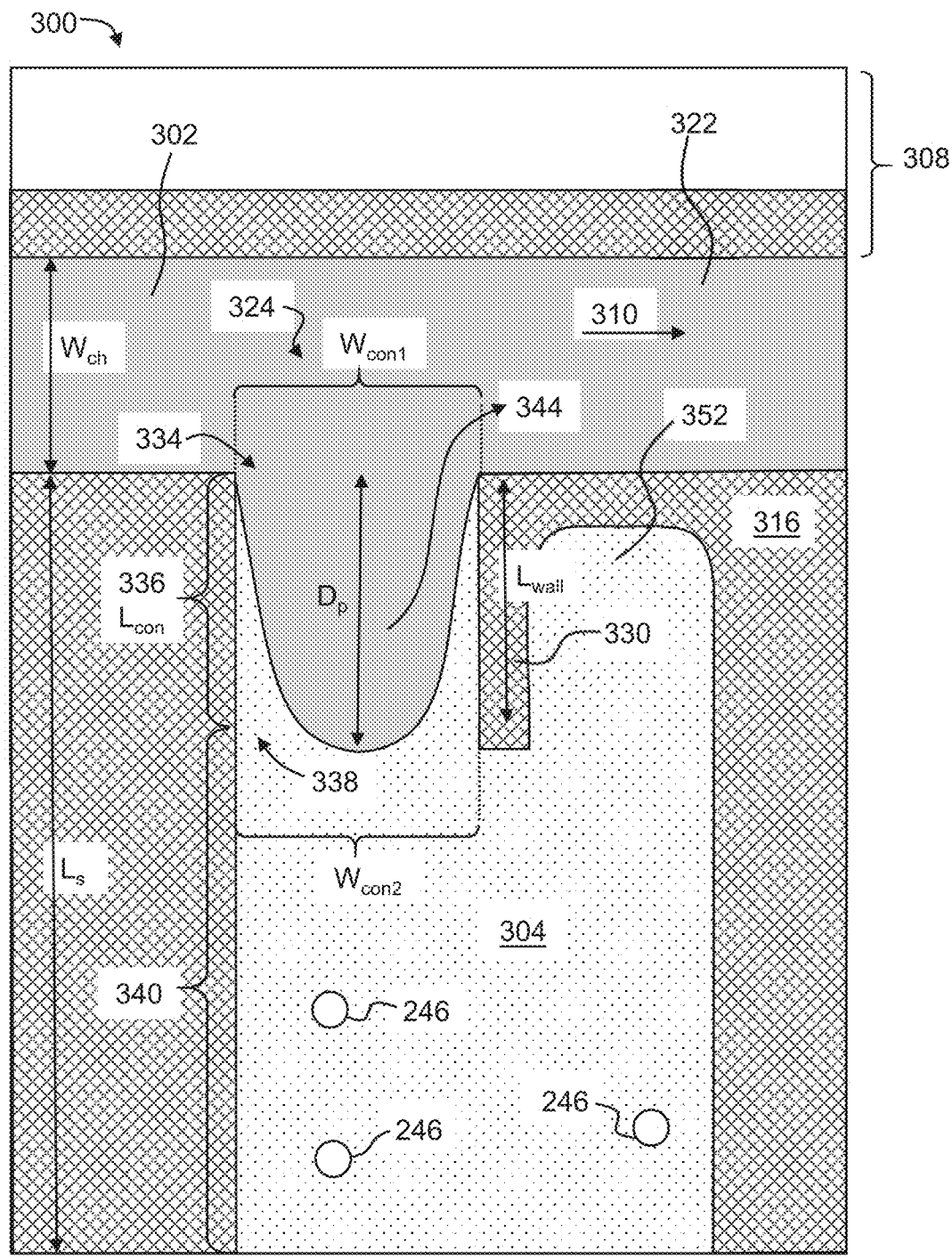
FIG. 3 illustrates a sequestration pen of a microfluidic device according to some embodiments of the disclosure.

FIG. 3 depicts another exemplary embodiment of a microfluidic device 300 containing microfluidic circuit structure 308, which includes a channel 322 and sequestration pen 324, which has features and properties like any of the sequestration pens described herein for microfluidic devices 100, 175, 200, 400, 520 and any other microfluidic devices described herein.

The exemplary microfluidic devices of FIG. 3 includes a microfluidic channel 322, having a width $W_{ch}$, as described herein, and containing a flow 310 of first fluidic medium 302 and one or more sequestration pens 324 (only one illustrated in FIG. 3). The sequestration pens 324 each have a length $L_s$, a connection region 336, and an isolation region 340, where the isolation region 340 contains a second fluidic medium 304. The connection region 336 has a proximal opening 334, having a width $W_{con1}$, which opens to the microfluidic channel 322, and a distal opening 338, having a width $W_{con2}$, which opens to the isolation region 340. The width $W_{con1}$ may or may not be the same as $W_{con2}$, as described herein. The walls of each sequestration pen 324 may be formed of microfluidic circuit material 316, which may further form the connection region walls 330. A connection region wall 330 can correspond to a structure that is laterally positioned with respect to the proximal opening 334 and at least partially extends into the enclosed portion of the sequestration pen 324. In some embodiments, the length $L_{con}$ of the connection region 336 is at least partially defined by length $L_{wall}$ of the connection region wall 330. The connection region wall 330 may have a length $L_{wall}$, selected to be more than the penetration depth $D_p$ of the secondary flow 344. Thus, the secondary flow 344 can be wholly contained within the connection region without extending into the isolation region 340.

The connection region wall 330 may define a hook region 352, which is a sub-region of the isolation region 340 of the sequestration pen 324. Since the connection region wall 330 extends into the inner cavity of the sequestration pen, the connection region wall 330 can act as a physical barrier to shield hook region 352 from secondary flow 344, with selection of the length of $L_{wall}$, contributing to the extent of the hook region. In some embodiments, the longer the length $L_{wall}$ of the connection region wall 330, the more sheltered the hook region 352.

In sequestration pens configured like those of FIGS. 2A-2C and 3, the isolation region may have a shape and size of any type, and may be selected to regulate diffusion of nutrients, reagents, and/or media into the sequestration pen to reach to a far wall of the sequestration pen, e.g., opposite the proximal opening of the connection region to the flow region (or microfluidic channel). The size and shape of the isolation region may further be selected to regulate diffusion of waste products and/or secreted products of a biological micro-object out from the isolation region to the flow region via the proximal opening of the connection region of the sequestration pen. In general, the shape of the isolation region is not critical to the ability of the sequestration pen to isolate micro-objects from direct flow in the flow region.

In some other embodiments of sequestration pens, the isolation region may have more than one opening fluidically connecting the isolation region with the flow region of the microfluidic device. However, for an isolation region having a number of n openings fluidically connecting the isolation region to the flow region (or two or more flow regions), n−1 openings can be valved. When the n−1 valved openings are closed, the isolation region has only one effective opening, and exchange of materials into/out of the isolation region occurs only by diffusion.

Examples of microfluidic devices having pens in which biological micro-objects can be placed, cultured, and/or monitored have been described, for example, in U.S. Pat. No. 9,857,333 (Chapman, et al.), U.S. Pat. No. 10,010,882 (White, et al.), and U.S. Pat. No. 9,889,445 (Chapman, et al.), each of which is incorporated herein by reference in its entirety.

Sequestration pen dimensions. Various dimensions and/or features of the sequestration pens and the microfluidic channels to which the sequestration pens open, as described herein, may be selected to limit introduction of contaminants or unwanted micro-objects into the isolation region of a sequestration pen from the flow region/microfluidic channel; limit the exchange of components in the fluidic medium from the channel or from the isolation region to substantially only diffusive exchange; facilitate the transfer of micro-objects into and/or out of the sequestration pens; and/or facilitate growth or expansion of the biological cells. Microfluidic channels and sequestration pens, for any of the embodiments described herein, may have any suitable combination of dimensions, may be selected by one of skill from the teachings of this disclosure, as follows.

The proximal opening of the connection region of a sequestration pen may have a width (e.g., $W_{con}$ or $W_{con1}$) that is at least as large as the largest dimension of a micro-object (e.g., a biological cell, which may be a plant cell, such as a plant protoplast) for which the sequestration pen is intended. In some embodiments, the proximal opening has a width (e.g., $W_{con}$ or $W_{con1}$) of about 20 microns, about 40 microns, about 50 microns, about 60 microns, about 75 microns, about 100 microns, about 150 microns, about 200 microns, or about 300 microns. The foregoing are examples only, and the width (e.g., $W_{con}$ or $W_{con1}$) of a proximal opening can be selected to be a value between any of the values listed above (e.g., about 20-200 microns, about 20-150 microns, about 20-100 microns, about 20-75 microns, about 20-60 microns, about 50-300 microns, about 50-200 microns, about 50-150 microns, about 50-100 microns, about 50-75 microns, about 75-150 microns, about 75-100 microns, about 100-300 microns, about 100-200 microns, or about 200-300 microns).

In some embodiments, the connection region of the sequestration pen may have a length (e.g., $L_{con}$) from the proximal opening to the distal opening to the isolation region of the sequestration pen that is at least 0.5 times, at least 0.6 times, at least 0.7 times, at least 0.8 times, at least 0.9 times, at least 1.0 times, at least 1.1 times, at least 1.2 times, at least 1.3 times, at least 1.4 times, at least 1.5 times, at least 1.75 times, at least 2.0 times, at least 2.25 times, at least 2.5 times, at least 2.75 times, at least 3.0 times, at least 3.5 times, at least 4.0 times, at least 4.5 times, at least 5.0 times, at least 6.0 times, at least 7.0 times, at least 8.0 times, at least 9.0 times, or at least 10.0 times the width (e.g., $W_{con}$ or $W_{con1}$) of the proximal opening. Thus, for example, the proximal opening of the connection region of a sequestration pen may have a width (e.g., $W_{con}$ or $W_{con1}$) from about 20 microns to about 200 microns (e.g., about 50 microns to about 150 microns), and the connection region may have a length $L_{con}$ that is at least 1.0 times (e.g., at least 1.5 times, or at least 2.0 times) the width of the proximal opening. As another example, the proximal opening of the connection region of a sequestration pen may have a width (e.g., $W_{con}$ or $W_{con1}$) from about 20 microns to about 100 microns (e.g., about 20 microns to about 60 microns), and the connection region may have a length $L_{con}$ that is at least 1.0 times (e.g., at least 1.5 times, or at least 2.0 times) the width of the proximal opening.

The microfluidic channel of a microfluidic device to which a sequestration pen opens may have specified size (e.g., width or height). In some embodiments, the height (e.g., $H_{ch}$) of the microfluidic channel at a proximal opening to the connection region of a sequestration pen can be within any of the following ranges: 20-100 microns, 20-90 microns, 20-80 microns, 20-70 microns, 20-60 microns, 20-50 microns, 30-100 microns, 30-90 microns, 30-80 microns, 30-70 microns, 30-60 microns, 30-50 microns, 40-100 microns, 40-90 microns, 40-80 microns, 40-70 microns, 40-60 microns, or 40-50 microns. The foregoing are examples only, and the height (e.g., $H_{ch}$) of the microfluidic channel (e.g., 122) can be selected to be between any of the values listed above. Moreover, the height (e.g., $H_{ch}$) of the microfluidic channel 122 can be selected to be any of these heights in regions of the microfluidic channel other than at a proximal opening of a sequestration pen.

The width (e.g., $W_{ch}$) of the microfluidic channel at the proximal opening to the connection region of a sequestration pen can be within any of the following ranges: about 20-500 microns, 20-400 microns, 20-300 microns, 20-200 microns, 20-150 microns, 20-100 microns, 20-80 microns, 20-60 microns, 30-400 microns, 30-300 microns, 30-200 microns, 30-150 microns, 30-100 microns, 30-80 microns, 30-60 microns, 40-300 microns, 40-200 microns, 40-150 microns, 40-100 microns, 40-80 microns, 40-60 microns, 50-1000 microns, 50-500 microns, 50-400 microns, 50-300 microns, 50-250 microns, 50-200 microns, 50-150 microns, 50-100 microns, 50-80 microns, 60-300 microns, 60-200 microns, 60-150 microns, 60-100 microns, 60-80 microns, 70-500 microns, 70-400 microns, 70-300 microns, 70-250 microns, 70-200 microns, 70-150 microns, 70-100 microns, 80-100 microns, 90-400 microns, 90-300 microns, 90-250 microns, 90-200 microns, 90-150 microns, 100-300 microns, 100-250 microns, 100-200 microns, 100-150 microns, 100-120 microns, 200-800 microns, 200-700 microns, or 200-600 microns. The foregoing are examples only, and the width (e.g., $W_{ch}$) of the microfluidic channel can be a value selected to be between any of the values listed above. Moreover, the width (e.g., $W_{ch}$) of the microfluidic channel can be selected to be in any of these widths in regions of the microfluidic channel other than at a proximal opening of a sequestration pen. In some embodiments, the width $W_{ch}$ of the microfluidic channel at the proximal opening to the connection region of the sequestration pen (e.g., taken transverse to the direction of bulk flow of fluid through the channel) can be substantially perpendicular to a width (e.g., $W_{con}$ or $W_{con1}$) of the proximal opening.

A cross-sectional area of the microfluidic channel at a proximal opening to the connection region of a sequestration pen can be about 500-50,000 square microns, 500-40,000 square microns, 500-30,000 square microns, 500-25,000 square microns, 500-20,000 square microns, 500-15,000 square microns, 500-10,000 square microns, 500-7,500 square microns, 500-5,000 square microns, 1,000-25,000 square microns, 1,000-20,000 square microns, 1,000-15,000 square microns, 1,000-10,000 square microns, 1,000-7,500 square microns, 1,000-5,000 square microns, 2,000-20,000 square microns, 2,000-15,000 square microns, 2,000-10,000 square microns, 2,000-7,500 square microns, 2,000-6,000 square microns, 3,000-20,000 square microns, 3,000-15,000 square microns, 3,000-10,000 square microns, 3,000-7,500 square microns, or 3,000 to 6,000 square microns. The foregoing are examples only, and the cross-sectional area of the microfluidic channel at the proximal opening can be selected to be between any of the values listed above. In various embodiments, and the cross-sectional area of the microfluidic channel at regions of the microfluidic channel other than at the proximal opening can also be selected to be between any of the values listed above. In some embodiments, the cross-sectional area is selected to be a substantially uniform value for the entire length of the microfluidic channel.

In some embodiments, the microfluidic chip is configured such that the proximal opening (e.g., 234 or 334) of the connection region of a sequestration pen may have a width (e.g., $W_{con}$ or $W_{con1}$) from about 20 microns to about 200 microns (e.g., about 50 microns to about 150 microns), the connection region may have a length $L_{con}$ (e.g., 236 or 336) that is at least 1.0 times (e.g., at least 1.5 times, or at least 2.0 times) the width of the proximal opening, and the microfluidic channel may have a height (e.g., $H_{ch}$) at the proximal opening of about 30 microns to about 60 microns. As another example, the proximal opening (e.g., 234 or 334) of the connection region of a sequestration pen may have a width (e.g., $W_{con}$ or $W_{con1}$) from about 20 microns to about 100 microns (e.g., about 20 microns to about 60 microns), the connection region may have a length $L_{con}$ (e.g., 236 or 336) that is at least 1.0 times (e.g., at least 1.5 times, or at least 2.0 times) the width of the proximal opening, and the microfluidic channel may have a height (e.g., $H_{ch}$) at the proximal opening of about 30 microns to about 60 microns. The foregoing are examples only, and the width (e.g., $W_{con}$ or $W_{con1}$) of the proximal opening (e.g., 234 or 274), the length (e.g., $L_{con}$) of the connection region, and/or the width (e.g., $W_{ch}$) of the microfluidic channel (e.g., 122 or 322), can be a value selected to be between any of the values listed above.

In some embodiments, the proximal opening (e.g., 234 or 334) of the connection region of a sequestration pen has a width (e.g., $W_{con}$ or $W_{con1}$) that is 2.0 times or less (e.g., 2.0, 1.9, 1.8, 1.5, 1.3, 1.0, 0.8, 0.5, or 0.1 times) the height (e.g., $H_{ch}$) of the flow region/microfluidic channel at the proximal opening, or has a value that lies within a range defined by any two of the foregoing values.

In some embodiments, the width $W_{con1}$ of a proximal opening (e.g., 234 or 334) of a connection region of a sequestration pen may be the same as a width $W_{con2}$ of the distal opening (e.g., 238 or 338) to the isolation region thereof. In some embodiments, the width $W_{con1}$ of the proximal opening may be different than a width $W_{con2}$ of the distal opening, and $W_{con1}$ and/or $W_{con2}$ may be selected from any of the values described for $W_{con}$ or $W_{con1}$. In some embodiments, the walls (including a connection region wall) that define the proximal opening and distal opening may be substantially parallel with respect to each other. In some embodiments, the walls that define the proximal opening and distal opening may be selected to not be parallel with respect to each other.

The length (e.g., $L_{con}$) of the connection region can be about 1-600 microns, 5-550 microns, 10-500 microns, 15-400 microns, 20-300 microns, 20-500 microns, 40-400 microns, 60-300 microns, 80-200 microns, about 100-150 microns, about 20-300 microns, about 20-250 microns, about 20-200 microns, about 20-150 microns, about 20-100 microns, about 30-250 microns, about 30-200 microns, about 30-150 microns, about 30-100 microns, about 30-80 microns, about 30-50 microns, about 45-250 microns, about 45-200 microns, about 45-100 microns, about 45-80 microns, about 45-60 microns, about 60-200 microns, about 60-150 microns, about 60-100 microns or about 60-80 microns. The foregoing are examples only, and length (e.g., $L_{con}$) of a connection region can be selected to be a value that is between any of the values listed above.

The connection region wall of a sequestration pen may have a length (e.g., $L_{wall}$) that is at least 0.5 times, at least 0.6 times, at least 0.7 times, at least 0.8 times, at least 0.9 times, at least 1.0 times, at least 1.1 times, at least 1.2 times, at least 1.3 times, at least 1.4 times, at least 1.5 times, at least 1.75 times, at least 2.0 times, at least 2.25 times, at least 2.5 times, at least 2.75 times, at least 3.0 times, or at least 3.5 times the width (e.g., $W_{con}$ or $W_{con1}$) of the proximal opening of the connection region of the sequestration pen. In some embodiments, the connection region wall may have a length $L_{wall}$ of about 20-200 microns, about 20-150 microns, about 20-100 microns, about 20-80 microns, or about 20-50 microns. The foregoing are examples only, and a connection region wall may have a length $L_{wall}$ selected to be between any of the values listed above.

A sequestration pen may have a length $L_s$ of about 40-600 microns, about 40-500 microns, about 40-400 microns, about 40-300 microns, about 40-200 microns, about 40-100 microns or about 40-80 microns. The foregoing are examples only, and a sequestration pen may have a length $L_s$ selected to be between any of the values listed above.

According to some embodiments, a sequestration pen may have a specified height (e.g., $H_s$). In some embodiments, a sequestration pen has a height $H_s$ of about 20 microns to about 200 microns (e.g., about 20 microns to about 150 microns, about 20 microns to about 100 microns, about 20 microns to about 60 microns, about 30 microns to about 150 microns, about 30 microns to about 100 microns, about 30 microns to about 60 microns, about 40 microns to about 150 microns, about 40 microns to about 100 microns, or about 40 microns to about 60 microns). The foregoing are examples only, and a sequestration pen can have a height $H_s$ selected to be between any of the values listed above.

The height $H_{con}$ of a connection region at a proximal opening of a sequestration pen can be a height within any of the following heights: 20-100 microns, 20-90 microns, 20-80 microns, 20-70 microns, 20-60 microns, 20-50 microns, 30-100 microns, 30-90 microns, 30-80 microns, 30-70 microns, 30-60 microns, 30-50 microns, 40-100 microns, 40-90 microns, 40-80 microns, 40-70 microns, 40-60 microns, or 40-50 microns. The foregoing are examples only, and the height $H_{con}$ of the connection region can be selected to be between any of the values listed above. Typically, the height $H_{con}$ of the connection region is selected to be the same as the height $H_{ch}$ of the microfluidic channel at the proximal opening of the connection region. Additionally, the height $H_s$ of the sequestration pen is typically selected to be the same as the height $H_{con}$ of a connection region and/or the height $H_{ch}$ of the microfluidic channel. In some embodiments, $H_s$, $H_{con}$, and $H_{ch}$ may be selected to be the same value of any of the values listed above for a selected microfluidic device.

The isolation region can be configured to contain only one, two, three, four, five, or a similar relatively small number of micro-objects. In other embodiments, the isolation region may contain more than 10, more than 50 or more than 100 micro-objects. Accordingly, the volume of an isolation region can be, for example, at least $1\times10^4$, $1\times10^5$, $5\times10^5$, $8\times10^5$, $1\times10^6$, $2\times10^6$, $4\times10^6$, $6\times10^6$, $1\times10^7$, $3\times10^7$, $5\times10^7$ $1\times10^8$, $5\times10^8$, or $8\times10^8$ cubic microns, or more. The foregoing are examples only, and the isolation region can be configured to contain numbers of micro-objects and volumes selected to be between any of the values listed above (e.g., a volume between $1\times10^5$ cubic microns and $5\times10^5$ cubic microns, between $5\times10^5$ cubic microns and $1\times10^6$ cubic microns, between $1\times10^6$ cubic microns and $2\times10^6$ cubic microns, or between $2\times10^6$ cubic microns and $1\times10^7$ cubic microns).

According to some embodiments, a sequestration pen of a microfluidic device may have a specified volume. The specified volume of the sequestration pen (or the isolation region of the sequestration pen) may be selected such that a single cell or a small number of cells (e.g., 2-10 or 2-5) can rapidly condition the medium and thereby attain favorable (or optimal) growth conditions. In some embodiments, the sequestration pen has a volume of about $5 \times 10^5$, $6 \times 10^5$, $8 \times 10^5$, $1 \times 10^6$, $2 \times 10^6$, $4 \times 10^6$, $8 \times 10^6$, $1 \times 10^7$, $3 \times 10^7$, $5 \times 10^7$, or about $8 \times 10^7$ cubic microns, or more. In some embodiments, the sequestration pen has a volume of about 1 nanoliter to about 50 nanoliters, 2 nanoliters to about 25 nanoliters, 2 nanoliters to about 20 nanoliters, about 2 nanoliters to about 15 nanoliters, or about 2 nanoliters to about 10 nanoliters. The foregoing are examples only, and a sequestration pen can have a volume selected to be any value that is between any of the values listed above.

According to some embodiments, the flow of fluidic medium within the microfluidic channel (e.g., 122 or 322) may have a specified maximum velocity (e.g., $V_{max}$). In some embodiments, the maximum velocity (e.g., $V_{max}$) may be set at around 0.2, 0.5, 0.7, 1.0, 1.3, 1.5, 2.0, 2.5, 3.0, 3.5, 4.0, 4.5, 5.0, 5.5, 6.0, 6.7, 7.0, 7.5, 8.0, 8.5, 9.0, 10, 11, 12, 13, 14, 15, 16, 17, 18, 19, or 20 microliters/sec. The foregoing are examples only, and the flow of fluidic medium within the microfluidic channel can have a maximum velocity (e.g., $V_{max}$) selected to be a value between any of the values listed above.

In various embodiment, the microfluidic device has sequestration pens configured as in any of the embodiments discussed herein where the microfluidic device has about 5 to about 10 sequestration pens, about 10 to about 50 sequestration pens, about 25 to about 200 sequestration pens, about 100 to about 500 sequestration pens, about 200 to about 1000 sequestration pens, about 500 to about 1500 sequestration pens, about 1000 to about 2500 sequestration pens, about 2000 to about 5000 sequestration pens, about 3500 to about 7000 sequestration pens, about 5000 to about 10,000 sequestration pens, about 7,500 to about 15,000 sequestration pens, about 12,500 to about 20,000 sequestration pens, about 15,000 to about 25,000 sequestration pens, about 20,000 to about 30,000 sequestration pens, about 25,000 to about 35,000 sequestration pens, about 30,000 to about 40,000 sequestration pens, about 35,000 to about 45,000 sequestration pens, or about 40,000 to about 50,000 sequestration pens. The sequestration pens need not all be the same size and may include a variety of configurations (e.g., different widths, different features within the sequestration pen).

Coating solutions and coating agents. In some embodiments, at least one inner surface of the microfluidic device includes a coating material that provides a layer of organic and/or hydrophilic molecules suitable for maintenance, expansion and/or movement of biological micro-object(s) (i.e., the biological micro-object exhibits increased viability, greater expansion and/or greater portability within the microfluidic device). The conditioned surface may reduce surface fouling, participate in providing a layer of hydration, and/or otherwise shield the biological micro-objects from contact with the non-organic materials of the microfluidic device interior.

In some embodiments, substantially all the inner surfaces of the microfluidic device include the coating material. The coated inner surface(s) may include the surface of a flow region (e.g., channel), chamber, or sequestration pen, or a combination thereof. In some embodiments, each of a plurality of sequestration pens has at least one inner surface coated with coating materials. In other embodiments, each of a plurality of flow regions or channels has at least one inner surface coated with coating materials. In some embodiments, at least one inner surface of each of a plurality of sequestration pens and each of a plurality of channels is coated with coating materials. The coating may be applied before or after introduction of biological micro-object(s), or may be introduced concurrently with the biological micro-object(s). In some embodiments, the biological micro-object(s) may be imported into the microfluidic device in a fluidic medium that includes one or more coating agents. In other embodiments, the inner surface(s) of the microfluidic device (e.g., a microfluidic device having an electrode activation substrate such as, but not limited to, a device including dielectrophoresis (DEP) electrodes) may be treated or "primed" with a coating solution comprising a coating agent prior to introduction of the biological micro-object(s) into the microfluidic device. Any convenient coating agent/coating solution can be used, including but not limited to: serum or serum factors, bovine serum albumin (BSA), polymers, detergents, enzymes, and any combination thereof.

Synthetic polymer-based coating materials. The at least one inner surface may include a coating material that comprises a polymer. The polymer may be non-covalently bound (e.g., it may be non-specifically adhered) to the at least one surface. The polymer may have a variety of structural motifs, such as found in block polymers (and copolymers), star polymers (star copolymers), and graft or comb polymers (graft copolymers), all of which may be suitable for the methods disclosed herein. A wide variety of alkylene ether containing polymers may be suitable for use in the microfluidic devices described herein, including but not limited to Pluronic® polymers such as Pluronic® L44, L64, P85, and F127 (including F127NF). Other examples of suitable coating materials are described in US2016/0312165, the contents of which are herein incorporated by reference in their entirety.

Covalently linked coating materials. In some embodiments, the at least one inner surface includes covalently linked molecules that provide a layer of organic and/or hydrophilic molecules suitable for maintenance/expansion of biological micro-object(s) within the microfluidic device, providing a conditioned surface for such cells. The covalently linked molecules include a linking group, wherein the linking group is covalently linked to one or more surfaces of the microfluidic device, as described below. The linking group is also covalently linked to a surface modifying moiety configured to provide a layer of organic and/or hydrophilic molecules suitable for maintenance/expansion/movement of biological micro-object(s).

In some embodiments, the covalently linked moiety configured to provide a layer of organic and/or hydrophilic molecules suitable for maintenance/expansion of biological micro-object(s) may include alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocylic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acids; or amino acids.

In various embodiments, the covalently linked moiety configured to provide a layer of organic and/or hydrophilic molecules suitable for maintenance/expansion of biological micro-object(s) in the microfluidic device may include non-polymeric moieties such as an alkyl moiety, amino acid moiety, alcohol moiety, amino moiety, carboxylic acid moiety, phosphonic acid moiety, sulfonic acid moiety, sulfamic acid moiety, or saccharide moiety. Alternatively, the covalently linked moiety may include polymeric moieties, which may include any of these moieties.

In some embodiments, a microfluidic device may have a hydrophobic layer upon the inner surface of the base which includes a covalently linked alkyl moiety. The covalently linked alkyl moiety may comprise carbon atoms forming a linear chain (e.g., a linear chain of at least 10 carbons, or at least 14, 16, 18, 20, 22, or more carbons) and may be an unbranched alkyl moiety. In some embodiments, the alkyl group may include a substituted alkyl group (e.g., some of the carbons in the alkyl group can be fluorinated or perfluorinated). In some embodiments, the alkyl group may include a first segment, which may include a perfluoroalkyl group, joined to a second segment, which may include a non-substituted alkyl group, where the first and second segments may be joined directly or indirectly (e.g., by means of an ether linkage). The first segment of the alkyl group may be located distal to the linking group, and the second segment of the alkyl group may be located proximal to the linking group.

In other embodiments, the covalently linked moiety may include at least one amino acid, which may include more than one type of amino acid. Thus, the covalently linked moiety may include a peptide or a protein. In some embodiments, the covalently linked moiety may include an amino acid which may provide a zwitterionic surface to support cell growth, viability, portability, or any combination thereof.

In other embodiments, the covalently linked moiety may further include a streptavidin or biotin moiety. In some embodiments, a modified biological moiety such as, for example, a biotinylated protein or peptide may be introduced to the inner surface of a microfluidic device bearing covalently linked streptavidin, and couple via the covalently linked streptavidin to the surface, thereby providing a modified surface presenting the protein or peptide.

In other embodiments, the covalently linked moiety may include at least one alkylene oxide moiety and may include any alkylene oxide polymer as described above. One useful class of alkylene ether containing polymers is polyethylene glycol (PEG $M_w$<100,000 Da) or alternatively polyethylene oxide (PEO, $M_w$>100,000). In some embodiments, a PEG may have an $M_w$ of about 1000 Da, 5000 Da, 10,000 Da or 20,000 Da. In some embodiments, the PEG polymer may further be substituted with a hydrophilic or charged moiety, such as but not limited to an alcohol functionality or a carboxylic acid moiety.

The covalently linked moiety may include one or more saccharides. The covalently linked saccharides may be mono-, di-, or polysaccharides. The covalently linked saccharides may be modified to introduce a reactive pairing moiety which permits coupling or elaboration for attachment to the surface. One exemplary covalently linked moiety may include a dextran polysaccharide, which may be coupled indirectly to a surface via an unbranched linker.

The coating material providing a conditioned surface may comprise only one kind of covalently linked moiety or may include more than one different kind of covalently linked moiety. For example, a polyethylene glycol conditioned surface may have covalently linked alkylene oxide moieties having a specified number of alkylene oxide units which are all the same, e.g., having the same linking group and covalent attachment to the surface, the same overall length, and the same number of alkylene oxide units. Alternatively, the coating material may have more than one kind of covalently linked moiety attached to the surface. For example, the coating material may include the molecules having covalently linked alkylene oxide moieties having a first specified number of alkylene oxide units and may further include a further set of molecules having bulky moieties such as a protein or peptide connected to a covalently attached alkylene oxide linking moiety having a greater number of alkylene oxide units. The different types of molecules may be varied in any suitable ratio to obtain the surface characteristics desired. For example, the conditioned surface having a mixture of first molecules having a chemical structure having a first specified number of alkylene oxide units and second molecules including peptide or protein moieties, which may be coupled via a biotin/streptavidin binding pair to the covalently attached alkylene linking moiety, may have a ratio of first molecules:second molecules of about 99:1; about 90:10; about 75:25; about 50:50; about 30:70; about 20:80; about 10:90; or any ratio selected to be between these values. In this instance, the first set of molecules having different, less sterically demanding termini and fewer backbone atoms can help to functionalize the entire substrate surface and thereby prevent undesired adhesion or contact with the silicon/silicon oxide, hafnium oxide or alumina making up the substrate itself. The selection of the ratio of mixture of first molecules to second molecules may also modulate the surface modification introduced by the second molecules bearing peptide or protein moieties.

Conditioned surface properties. Various factors can alter the physical thickness of the conditioned surface, such as the manner in which the conditioned surface is formed on the substrate (e.g. vapor deposition, liquid phase deposition, spin coating, flooding, and electrostatic coating). In some embodiments, the conditioned surface may have a thickness of about 1 nm to about 10 nm. In some embodiments, the covalently linked moieties of the conditioned surface may form a monolayer when covalently linked to the surface of the microfluidic device (which may include an electrode activation substrate having dielectrophoresis (DEP) or electrowetting (EW) electrodes) and may have a thickness of less than 10 nm (e.g., less than 5 nm, or about 1.5 to 3.0 nm). These values are in contrast to that of a surface prepared by spin coating, for example, which may typically have a thickness of about 30 nm. In some embodiments, the conditioned surface does not require a perfectly formed monolayer to be suitably functional for operation within a DEP-configured microfluidic device. In other embodiments, the conditioned surface formed by the covalently linked moieties may have a thickness of about 10 nm to about 50 nm.

Unitary or Multi-part conditioned surface. The covalently linked coating material may be formed by reaction of a molecule which already contains the moiety configured to provide a layer of organic and/or hydrophilic molecules suitable for maintenance/expansion of biological micro-object(s) in the microfluidic device, and may have a structure of Formula I, as shown below. Alternatively, the covalently linked coating material may be formed in a two-part sequence, having a structure of Formula II, by coupling the moiety configured to provide a layer of organic and/or hydrophilic molecules suitable for maintenance and/or expansion of biological micro-object(s) to a surface modifying ligand that itself has been covalently linked to the surface. In some embodiments, the surface may be formed in a two-part or three-part sequence, including a streptavidin/biotin binding pair, to introduce a protein, peptide, or mixed modified surface.

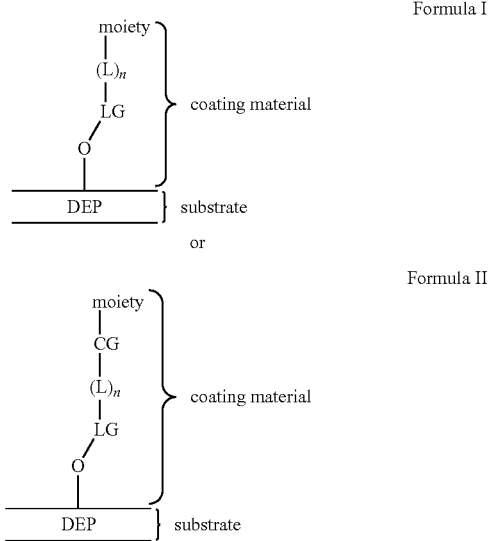

The coating material may be linked covalently to oxides of the surface of a DEP-configured or EW-configured substrate. The coating material may be attached to the oxides via a linking group ("LG"), which may be a siloxy or phosphonate ester group formed from the reaction of a siloxane or phosphonic acid group with the oxides. The moiety configured to provide a layer of organic and/or hydrophilic molecules suitable for maintenance/expansion of biological micro-object(s) in the microfluidic device can be any of the moieties described herein. The linking group LG may be directly or indirectly connected to the moiety configured to provide a layer of organic and/or hydrophilic molecules suitable for maintenance/expansion of biological micro-object(s) in the microfluidic device. When the linking group LG is directly connected to the moiety, optional linker ("L") is not present and n is 0. When the linking group LG is indirectly connected to the moiety, linker L is present and n is 1. The linker L may have a linear portion where a backbone of the linear portion may include 1 to 200 non-hydrogen atoms selected from any combination of silicon, carbon, nitrogen, oxygen, sulfur and/or phosphorus atoms, subject to chemical bonding limitations as is known in the art. It may be interrupted with any combination of one or more moieties, which may be chosen from ether, amino, carbonyl, amido, and/or phosphonate groups, arylene, heteroarylene, or heterocyclic groups. In some embodiments, the coupling group CG represents the resultant group from reaction of a reactive moiety $R_x$ and a reactive pairing moiety $R_{px}$ (i.e., a moiety configured to react with the reactive moiety $R_x$). CG may be a carboxamidyl group, a triazolylene group, substituted triazolylene group, a carboxamidyl, thioamidyl, an oxime, a mercaptyl, a disulfide, an ether, or alkenyl group, or any other suitable group that may be formed upon reaction of a reactive moiety with its respective reactive pairing moiety. In some embodiments, CG may further represent a streptavidin/biotin binding pair.

Further details of suitable coating treatments and modifications, as well as methods of preparation, may be found at U.S. Patent Application Publication No. US2016/0312165 (Lowe, Jr., et al.), U.S. Patent Application Publication No US2017/0173580 (Lowe, Jr., et al), International Patent Application Publication WO2017/205830 (Lowe, Jr., et al.), and International Patent Application Publication WO2019/01880 (Beemiller et al.), each of which disclosures is herein incorporated by reference in its entirety.

Microfluidic device motive technologies. The microfluidic devices described herein can be used with any type of motive technology. As described herein, the control and monitoring equipment of the system can comprise a motive module for selecting and moving objects, such as micro-objects or droplets, in the microfluidic circuit of a microfluidic device. The motive technology (ies) may include, for example, dielectrophoresis (DEP), electrowetting (EW), and/or other motive technologies. The microfluidic device can have a variety of motive configurations, depending upon the type of object being moved and other considerations. Returning to FIG. 1A, for example, the support structure 104 and/or cover 110 of the microfluidic device 100 can comprise DEP electrode activation substrates for selectively inducing motive forces on micro-objects in the fluidic medium 180 in the microfluidic circuit 120 and thereby select, capture, and/or move individual micro-objects or groups of micro-objects.

In some embodiments, motive forces are applied across the fluidic medium 180 (e.g., in the flow path and/or in the sequestration pens) via one or more electrodes (not shown) to manipulate, transport, separate and sort micro-objects located therein. For example, in some embodiments, motive forces are applied to one or more portions of microfluidic circuit 120 in order to transfer a single micro-object from the flow path 106 into a desired microfluidic sequestration pen. In some embodiments, motive forces are used to prevent a micro-object within a sequestration pen from being displaced therefrom. Further, in some embodiments, motive forces are used to selectively remove a micro-object from a sequestration pen that was previously collected in accordance with the embodiments of the current disclosure.

In some embodiments, the microfluidic device is configured as an optically-actuated electrokinetic device, such as in optoelectronic tweezer (OET) and/or optoelectrowetting (OEW) configured device. Examples of suitable OET configured devices (e.g., containing optically actuated dielectrophoresis electrode activation substrates) can include those illustrated in U.S. Pat. No. RE 44,711 (Wu, et al.) (originally issued as U.S. Pat. No. 7,612,355), U.S. Pat. No. 7,956,339 (Ohta, et al.), U.S. Pat. No. 9,908,115 (Hobbs et al.), and U.S. Pat. No. 9,403,172 (Short et al), each of which is incorporated herein by reference in its entirety. Examples of suitable OEW configured devices can include those illustrated in U.S. Pat. No. 6,958,132 (Chiou, et al.), and U.S. Pat. No. 9,533,306 (Chiou, et al.), each of which is incorporated herein by reference in its entirety. Examples of suitable optically-actuated electrokinetic devices that include combined OET/OEW configured devices can include those illustrated in U.S. Patent Application Publication No. 2015/0306598 (Khandros, et al.), U.S. Patent Application Publication No 2015/0306599 (Khandros, et al.), and U.S. Patent Application Publication No. 2017/0173580 (Lowe, et al.), each of which is incorporated herein by reference in its entirety.

It should be understood that, for purposes of simplicity, the various examples of FIGS. 1-5B may illustrate portions of microfluidic devices while not depicting other portions. Further, FIGS. 1-5B may be part of, and implemented as, one or more microfluidic systems. In one non-limiting example, FIGS. 4A and 4B show a side cross-sectional view and a top cross-sectional view, respectively, of a portion of an enclosure 102 of the microfluidic device 400 having a region/chamber 402, which may be part of a fluidic circuit element having a more detailed structure, such as a growth chamber, a sequestration pen (which may be like any sequestration pen described herein), a flow region, or a flow channel. For instance, microfluidic device 400 may be similar to microfluidic devices 100, 175, 200, 300, 520 or any other microfluidic device as described herein. Furthermore, the microfluidic device 400 may include other fluidic circuit elements and may be part of a system including control and monitoring equipment 152, described above, having one or more of the media module 160, motive module 162, imaging module 164, optional tilting module 166, and other modules 168. Microfluidic devices 175, 200, 300, 520 and any other microfluidic devices described herein may similarly have any of the features described in detail for FIGS. 1A-1B and 4A-4B.

Figure 4A:
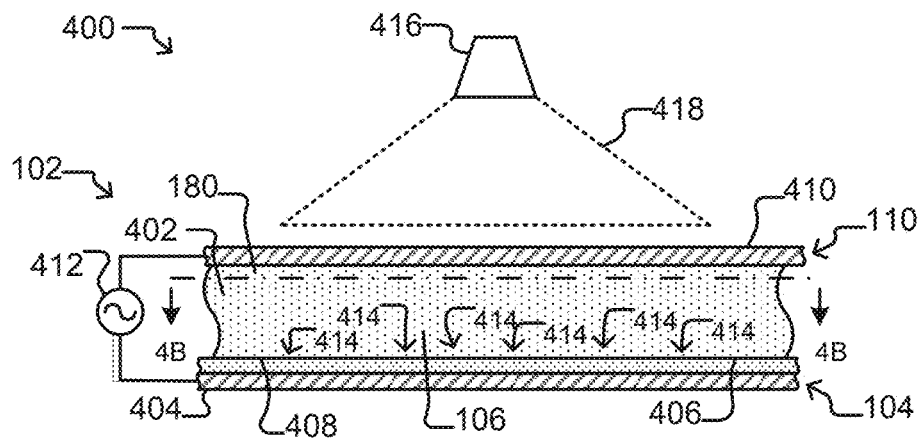
FIGS. 4A-4B illustrate electrokinetic features of a microfluidic device according to some embodiments of the disclosure.

As shown in the example of FIG. 4A, the microfluidic device 400 includes a support structure 104 having a bottom electrode 404 and an electrode activation substrate 406 overlying the bottom electrode 404, and a cover 110 having a top electrode 410, with the top electrode 410 spaced apart from the bottom electrode 404. The top electrode 410 and the electrode activation substrate 406 define opposing surfaces of the region/chamber 402. A fluidic medium 180 contained in the region/chamber 402 thus provides a resistive connection between the top electrode 410 and the electrode activation substrate 406. A power source 412 configured to be connected to the bottom electrode 404 and the top electrode 410 and create a biasing voltage between the electrodes, as required for the generation of DEP forces in the region/chamber 402, is also shown. The power source 412 can be, for example, an alternating current (AC) power source.

Figure 4B:
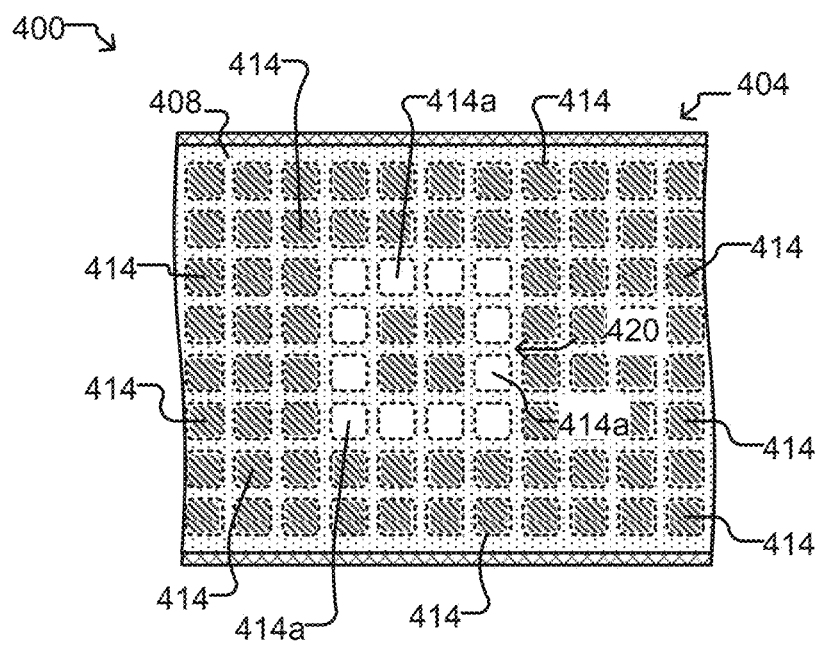

In certain embodiments, the microfluidic device 200 illustrated in FIGS. 4A and 4B can have an optically-actuated DEP electrode activation substrate. Accordingly, changing patterns of light 418 from the light source 416, which may be controlled by the motive module 162, can selectively activate and deactivate changing patterns of DEP electrodes at regions 414 of the inner surface 408 of the electrode activation substrate 406. (Hereinafter the regions 414 of a microfluidic device having a DEP electrode activation substrate are referred to as "DEP electrode regions.") As illustrated in FIG. 4B, a light pattern 418 directed onto the inner surface 408 of the electrode activation substrate 406 can illuminate select DEP electrode regions 414a (shown in white) in a pattern, such as a square. The non-illuminated DEP electrode regions 414 (cross-hatched) are hereinafter referred to as "dark" DEP electrode regions 414. The relative electrical impedance through the DEP electrode activation substrate 406 (i.e., from the bottom electrode 404 up to the inner surface 408 of the electrode activation substrate 406 which interfaces with the fluidic medium 180 in the flow region 106) is greater than the relative electrical impedance through the fluidic medium 180 in the region/chamber 402 (i.e., from the inner surface 408 of the electrode activation substrate 406 to the top electrode 410 of the cover 110) at each dark DEP electrode region 414. An illuminated DEP electrode region 414a, however, exhibits a reduced relative impedance through the electrode activation substrate 406 that is less than the relative impedance through the fluidic medium 180 in the region/chamber 402 at each illuminated DEP electrode region 414a.

With the power source 412 activated, the foregoing DEP configuration creates an electric field gradient in the fluidic medium 180 between illuminated DEP electrode regions 414a and adjacent dark DEP electrode regions 414, which in turn creates local DEP forces that attract or repel nearby micro-objects (not shown) in the fluidic medium 180. DEP electrodes that attract or repel micro-objects in the fluidic medium 180 can thus be selectively activated and deactivated at many different such DEP electrode regions 414 at the inner surface 408 of the region/chamber 402 by changing light patterns 418 projected from a light source 416 into the microfluidic device 400. Whether the DEP forces attract or repel nearby micro-objects can depend on such parameters as the frequency of the power source 412 and the dielectric properties of the fluidic medium 180 and/or micro-objects (not shown). Depending on the frequency of the power applied to the DEP configuration and selection of fluidic media (e.g., a highly conductive media such as PBS or other media appropriate for maintaining biological cells), negative DEP forces may be produced. Negative DEP forces may repel the micro-objects away from the location of the induced non-uniform electrical field. In some embodiments, a microfluidic device incorporating DEP technology may generate negative DEP forces.

The square pattern 420 of illuminated DEP electrode regions 414a illustrated in FIG. 4B is an example only. Any pattern of the DEP electrode regions 414 can be illuminated (and thereby activated) by the pattern of light 418 projected into the microfluidic device 400, and the pattern of illuminated/activated DEP electrode regions 414 can be repeatedly changed by changing or moving the light pattern 418.

In some embodiments, the electrode activation substrate 406 can comprise or consist of a photoconductive material. In such embodiments, the inner surface 408 of the electrode activation substrate 406 can be featureless. For example, the electrode activation substrate 406 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 μm. In such embodiments, the DEP electrode regions 414 can be created anywhere and in any pattern on the inner surface 408 of the electrode activation substrate 406, in accordance with the light pattern 418. The number and pattern of the DEP electrode regions 214 thus need not be fixed, but can correspond to the light pattern 418. Examples of microfluidic devices having a DEP configuration comprising a photoconductive layer such as discussed above have been described, for example, in U.S. Pat. No. RE 44,711 (Wu, et al.) (originally issued as U.S. Pat. No. 7,612,355), each of which is incorporated herein by reference in its entirety.

In other embodiments, the electrode activation substrate 406 can comprise a substrate comprising a plurality of doped layers, electrically insulating layers (or regions), and electrically conductive layers that form semiconductor integrated circuits, such as is known in semiconductor fields. For example, the electrode activation substrate 406 can comprise a plurality of phototransistors, including, for example, lateral bipolar phototransistors, with each phototransistor corresponding to a DEP electrode region 414. Alternatively, the electrode activation substrate 406 can comprise electrodes (e.g., conductive metal electrodes) controlled by phototransistor switches, with each such electrode corresponding to a DEP electrode region 414. The electrode activation substrate 406 can include a pattern of such phototransistors or phototransistor-controlled electrodes. The pattern, for example, can be an array of substantially square phototransistors or phototransistor-controlled electrodes arranged in rows and columns. Alternatively, the pattern can be an array of substantially hexagonal phototransistors or phototransistor-controlled electrodes that form a hexagonal lattice. Regardless of the pattern, electric circuit elements can form electrical connections between the DEP electrode regions 414 at the inner surface 408 of the electrode activation substrate 406 and the bottom electrode 404, and those electrical connections (i.e., phototransistors or electrodes) can be selectively activated and deactivated by the light pattern 418, as described above.

Examples of microfluidic devices having electrode activation substrates that comprise phototransistors have been described, for example, in U.S. Pat. No. 7,956,339 (Ohta et al.) and U.S. Pat. No. 9,908,115 (Hobbs et al.), the entire contents of each of which are incorporated herein by reference. Examples of microfluidic devices having electrode activation substrates that comprise electrodes controlled by phototransistor switches have been described, for example, in U.S. Pat. No. 9,403,172 (Short et al.), which is incorporated herein by reference in its entirety.

In some embodiments of a DEP configured microfluidic device, the top electrode 410 is part of a first wall (or cover 110) of the enclosure 402, and the electrode activation substrate 406 and bottom electrode 404 are part of a second wall (or support structure 104) of the enclosure 102. The region/chamber 402 can be between the first wall and the second wall. In other embodiments, the electrode 410 is part of the second wall (or support structure 104) and one or both of the electrode activation substrate 406 and/or the electrode 410 are part of the first wall (or cover 110). Moreover, the light source 416 can alternatively be used to illuminate the enclosure 102 from below.

With the microfluidic device 400 of FIGS. 4A-4B having a DEP electrode activation substrate, the motive module 162 of control and monitoring equipment 152, as described for FIG. 1A herein, can select a micro-object (not shown) in the fluidic medium 180 in the region/chamber 402 by projecting a light pattern 418 into the microfluidic device 400 to activate a first set of one or more DEP electrodes at DEP electrode regions 414a of the inner surface 408 of the electrode activation substrate 406 in a pattern (e.g., square pattern 420) that surrounds and captures the micro-object. The motive module 162 can then move the in situ-generated captured micro-object by moving the light pattern 418 relative to the microfluidic device 400 to activate a second set of one or more DEP electrodes at DEP electrode regions 414. Alternatively, the microfluidic device 400 can be moved relative to the light pattern 418.

In other embodiments, the microfluidic device 400 may be a DEP configured device that does not rely upon light activation of DEP electrodes at the inner surface 408 of the electrode activation substrate 406. For example, the electrode activation substrate 406 can comprise selectively addressable and energizable electrodes positioned opposite to a surface including at least one electrode (e.g., cover 110). Switches (e.g., transistor switches in a semiconductor substrate) may be selectively opened and closed to activate or inactivate DEP electrodes at DEP electrode regions 414, thereby creating a net DEP force on a micro-object (not shown) in region/chamber 402 in the vicinity of the activated DEP electrodes. Depending on such characteristics as the frequency of the power source 412 and the dielectric properties of the medium (not shown) and/or micro-objects in the region/chamber 402, the DEP force can attract or repel a nearby micro-object. By selectively activating and deactivating a set of DEP electrodes (e.g., at a set of DEP electrodes regions 414 that forms a square pattern 420), one or more micro-objects in region/chamber 402 can be selected and moved within the region/chamber 402. The motive module 162 in FIG. 1A can control such switches and thus activate and deactivate individual ones of the DEP electrodes to select, and move particular micro-objects (not shown) around the region/chamber 402. Microfluidic devices having a DEP electrode activation substrates that includes selectively addressable and energizable electrodes are known in the art and have been described, for example, in U.S. Pat. No. 6,294,063 (Becker, et al.) and U.S. Pat. No. 6,942,776 (Medoro), each of which is incorporated herein by reference in its entirety.

Regardless of whether the microfluidic device 400 has a dielectrophoretic electrode activation substrate, an electrowetting electrode activation substrate or a combination of both a dielectrophoretic and an electrowetting activation substrate, a power source 412 can be used to provide a potential (e.g., an AC voltage potential) that powers the electrical circuits of the microfluidic device 400. The power source 412 can be the same as, or a component of, the power source 192 referenced in FIG. 1A. Power source 412 can be configured to provide an AC voltage and/or current to the top electrode 410 and the bottom electrode 404. For an AC voltage, the power source 412 can provide a frequency range and an average or peak power (e.g., voltage or current) range sufficient to generate net DEP forces (or electrowetting forces) strong enough to select and move individual micro-objects (not shown) in the region/chamber 402, as discussed above, and/or to change the wetting properties of the inner surface 408 of the support structure 104 in the region/chamber 202, as also discussed above. Such frequency ranges and average or peak power ranges are known in the art. See, e.g., U.S. Pat. No. 6,958,132 (Chiou, et al.), U.S. Pat. No. RE44,711 (Wu, et al.) (originally issued as U.S. Pat. No. 7,612,355), and U.S. Patent Application Publication Nos. 2014/0124370 (Short, et al.), 2015/0306598 (Khandros, et al.), 2015/0306599 (Khandros, et al.), and 2017/0173580 (Lowe, Jr. et al.), each of which disclosures are herein incorporated by reference in its entirety.

Other forces may be utilized within the microfluidic devices, alone or in combination, to move selected micro-objects. Bulk fluidic flow within the microfluidic channel may move micro-objects within the flow region. Localized fluidic flow, which may be operated within the microfluidic channel, within a sequestration pen, or within another kind of chamber (e.g., a reservoir) can be also be used to move selected micro-objects. Localized fluidic flow can be used to move selected micro-objects out of the flow region into a non-flow region such as a sequestration pen or the reverse, from a non-flow region into a flow region. The localized flow can be actuated by deforming a deformable wall of the microfluidic device, as described in U.S. Pat. No. 10,058,865 (Breinlinger, et al.), which is incorporated herein by reference in its entirety.

Gravity may be used to move micro-objects within the microfluidic channel, into a sequestration pen, and/or out of a sequestration pen or other chamber, as described in U.S. Pat. No. 9,744,533 (Breinlinger, et al.), which is incorporated herein by reference in its entirety. Use of gravity (e.g., by tilting the microfluidic device and/or the support to which the microfluidic device is attached) may be useful for bulk movement of cells into or out of the sequestration pens from/to the flow region. Magnetic forces may be employed to move micro-objects including paramagnetic materials, which can include magnetic micro-objects attached to or associated with a biological micro-object. Alternatively, or in additional, centripetal forces may be used to move micro-objects within the microfluidic channel, as well as into or out of sequestration pens or other chambers in the microfluidic device.

In another alternative mode of moving micro-objects, laser-generated dislodging forces may be used to export micro-objects or assist in exporting micro-objects from a sequestration pen or any other chamber in the microfluidic device, as described in International Patent Publication No. WO2017/117408 (Kurz, et al.), which is incorporated herein by reference in its entirety.

In some embodiments, DEP forces are combined with other forces, such as fluidic flow (e.g., bulk fluidic flow in a channel or localized fluidic flow actuated by deformation of a deformable surface of the microfluidic device, laser generated dislodging forces, and/or gravitational force), so as to manipulate, transport, separate and sort micro-objects and/or droplets within the microfluidic circuit 120. In some embodiments, the DEP forces can be applied prior to the other forces. In other embodiments, the DEP forces can be applied after the other forces. In still other instances, the DEP forces can be applied at the same time as the other forces or in an alternating manner with the other forces.

System. Returning to FIG. 1A, a system 150 for operating and controlling microfluidic devices is shown, such as for controlling the microfluidic device 100. The electrical power source 192 can provide electric power to the microfluidic device 100, providing biasing voltages or currents as needed. The electrical power source 192 can, for example, comprise one or more alternating current (AC) and/or direct current (DC) voltage or current sources.

System 150 can further include a media source 178. The media source 178 (e.g., a container, reservoir, or the like) can comprise multiple sections or containers, each for holding a different fluidic medium 180. Thus, the media source 178 can be a device that is outside of and separate from the microfluidic device 100, as illustrated in FIG. 1A. Alternatively, the media source 178 can be located in whole or in part inside the enclosure 102 of the microfluidic device 100. For example, the media source 178 can comprise reservoirs that are part of the microfluidic device 100.

FIG. 1A also illustrates simplified block diagram depictions of examples of control and monitoring equipment 152 that constitute part of system 150 and can be utilized in conjunction with a microfluidic device 100. As shown, examples of such control and monitoring equipment 152 can include a master controller 154 comprising a media module 160 for controlling the media source 178, a motive module 162 for controlling movement and/or selection of micro-objects (not shown) and/or medium (e.g., droplets of medium) in the microfluidic circuit 120, an imaging module 164 for controlling an imaging device (e.g., a camera, microscope, light source or any combination thereof) for capturing images (e.g., digital images), and an optional tilting module 166 for controlling the tilting of the microfluidic device 100. The control equipment 152 can also include other modules 168 for controlling, monitoring, or performing other functions with respect to the microfluidic device 100. As shown, the monitoring equipment 152 can further include a display device 170 and an input/output device 172.

The master controller 154 can comprise a control module 156 and a digital memory 158. The control module 156 can comprise, for example, a digital processor configured to operate in accordance with machine executable instructions (e.g., software, firmware, source code, or the like) stored as non-transitory data or signals in the memory 158. Alternatively, or in addition, the control module 156 can comprise hardwired digital circuitry and/or analog circuitry. The media module 160, motive module 162, imaging module 164, optional tilting module 166, and/or other modules 168 can be similarly configured. Thus, functions, processes acts, actions, or steps of a process discussed herein as being performed with respect to the microfluidic device 100 or any other microfluidic apparatus can be performed by any one or more of the master controller 154, media module 160, motive module 162, imaging module 164, optional tilting module 166, and/or other modules 168 configured as discussed above. Similarly, the master controller 154, media module 160, motive module 162, imaging module 164, optional tilting module 166, and/or other modules 168 may be communicatively coupled to transmit and receive data used in any function, process, act, action or step discussed herein.

The media module 160 controls the media source 178. For example, the media module 160 can control the media source 178 to input a selected fluidic medium 180 into the enclosure 102 (e.g., through an inlet port 107). The media module 160 can also control removal of media from the enclosure 102 (e.g., through an outlet port (not shown)). One or more media can thus be selectively input into and removed from the microfluidic circuit 120. The media module 160 can also control the flow of fluidic medium 180 in the flow path 106 inside the microfluidic circuit 120. The media module 160 may also provide conditioning gaseous conditions to the media source 178, for example, providing an environment containing 5% $CO_2$ (or higher). The media module 160 may also control the temperature of an enclosure of the media source, for example, to provide feeder cells in the media source with proper temperature control.

Motive module. The motive module 162 can be configured to control selection and movement of micro-objects (not shown) in the microfluidic circuit 120. The enclosure 102 of the microfluidic device 100 can comprise one or more electrokinetic mechanisms including a dielectrophoresis (DEP) electrode activation substrate, optoelectronic tweezers (OET) electrode activation substrate, electrowetting (EW) electrode activation substrate, and/or an optoelectrowetting (OEW) electrode activation substrate, where the motive module 162 can control the activation of electrodes and/or transistors (e.g., phototransistors) to select and move micro-objects and/or droplets in the flow path 106 and/or within sequestration pens 124, 126, 128, and 130. The electrokinetic mechanism(s) may be any suitable single or combined mechanism as described within the paragraphs describing motive technologies for use within the microfluidic device. A DEP configured device may include one or more electrodes that apply a non-uniform electric field in the microfluidic circuit 120 sufficient to exert a dielectrophoretic force on micro-objects in the microfluidic circuit 120. An OET configured device may include photo-activatable electrodes to provide selective control of movement of micro-objects in the microfluidic circuit 120 via light-induced dielectrophoresis.

The imaging module 164 can control the imaging device. For example, the imaging module 164 can receive and process image data from the imaging device. Image data from the imaging device can comprise any type of information captured by the imaging device (e.g., the presence or absence of micro-objects, droplets of medium, accumulation of label, such as fluorescent label, etc.). Using the information captured by the imaging device, the imaging module 164 can further calculate the position of objects (e.g., micro-objects, droplets of medium) and/or the rate of motion of such objects within the microfluidic device 100.

The imaging device (part of imaging module 164, discussed below) can comprise a device, such as a digital camera, for capturing images inside microfluidic circuit 120. In some instances, the imaging device further comprises a detector having a fast frame rate and/or high sensitivity (e.g. for low light applications). The imaging device can also include a mechanism for directing stimulating radiation and/or light beams into the microfluidic circuit 120 and collecting radiation and/or light beams reflected or emitted from the microfluidic circuit 120 (or micro-objects contained therein). The emitted light beams may be in the visible spectrum and may, e.g., include fluorescent emissions. The reflected light beams may include reflected emissions originating from an LED or a wide spectrum lamp, such as a mercury lamp (e.g. a high-pressure mercury lamp) or a Xenon arc lamp. The imaging device may further include a microscope (or an optical train), which may or may not include an eyepiece.

Support Structure. System 150 may further comprise a support structure 190 configured to support and/or hold the enclosure 102 comprising the microfluidic circuit 120. In some embodiments, the optional tilting module 166 can be configured to activate the support structure 190 to rotate the microfluidic device 100 about one or more axes of rotation. The optional tilting module 166 can be configured to support and/or hold the microfluidic device 100 in a level orientation (i.e. at 0° relative to x- and y-axes), a vertical orientation (i.e. at 90° relative to the x-axis and/or the y-axis), or any orientation therebetween. The orientation of the microfluidic device 100 (and the microfluidic circuit 120) relative to an axis is referred to herein as the "tilt" of the microfluidic device 100 (and the microfluidic circuit 120). For example, support structure 190 can optionally be used to tilt the microfluidic device 100 (e.g., as controlled by optional tilting module 166) to 0.1°, 0.2°, 0.3°, 0.4°, 0.5°, 0.6°, 0.7°, 0.8°, 0.9°, 1°, 2°, 3°, 4°, 5°, 10°, 15°, 20°, 25°, 30°, 35°, 40°, 45°, 50°, 55°, 60°, 65°, 70°, 75°, 80°, 90° relative to the x-axis or any degree therebetween. When the microfluidic device is tilted at angles greater than about 15, tilting may be performed to create bulk movement of micro-objects into/out of sequestration pens from/into the flow region (e.g., microfluidic channel). In some embodiments, the support structure 190 can hold the microfluidic device 100 at a fixed angle of 0.1°, 0.2°, 0.3°, 0.4°, 0.5°, 0.6°, 0.7°, 0.8°, 0.9°, 1°, 2°, 3°, 4°, 5°, or 10° relative to the x-axis (horizontal), so long as DEP is an effective force to move micro-objects out of the sequestration pens into the microfluidic channel. Since the surface of the electrode activation substrate is substantially flat, DEP forces may be used even when the far end of the sequestration pen, opposite its opening to the microfluidic channel, is disposed at a position lower in a vertical direction than the microfluidic channel.

In some embodiments where the microfluidic device is tilted or held at a fixed angle relative to horizontal, the microfluidic device 100 may be disposed in an orientation such that the inner surface of the base of the flow path 106 is positioned at an angle above or below the inner surface of the base of the one or more sequestration pens opening laterally to the flow path. The term "above" as used herein denotes that the flow path 106 is positioned higher than the one or more sequestration pens on a vertical axis defined by the force of gravity (i.e. an object in a sequestration pen above a flow path 106 would have a higher gravitational potential energy than an object in the flow path), and inversely, for positioning of the flow path 106 below one or more sequestration pens. In some embodiments, the support structure 190 may be held at a fixed angle of less than about 5°, about 4°, about 3° or less than about 2° relative to the x-axis (horizontal), thereby placing the sequestration pens at a lower potential energy relative to the flow path. In some other embodiments, when long term culturing (e.g., for more than about 2, 3, 4, 5, 6, 7 or more days) is performed within the microfluidic device, the device may be supported on a culturing support and may be tilted at a greater angle of about 10°, 15°, 20°, 25°, 30°, or any angle therebetween to retain biological micro-objects within the sequestration pens during the long term culturing period. At the end of the culturing period, the microfluidic device containing the cultured biological micro-objects may be returned to the support 190 within system 150, where the angle of tilting is decreased to values as described above, affording the use of DEP to move the biological micro-objects out of the sequestration pens. Further examples of the use of gravitational forces induced by tilting are described in U.S. Pat. No. 9,744,533 (Breinlinger et al.), the contents of which are herein incorporated by reference in its entirety.

Figure 5A:
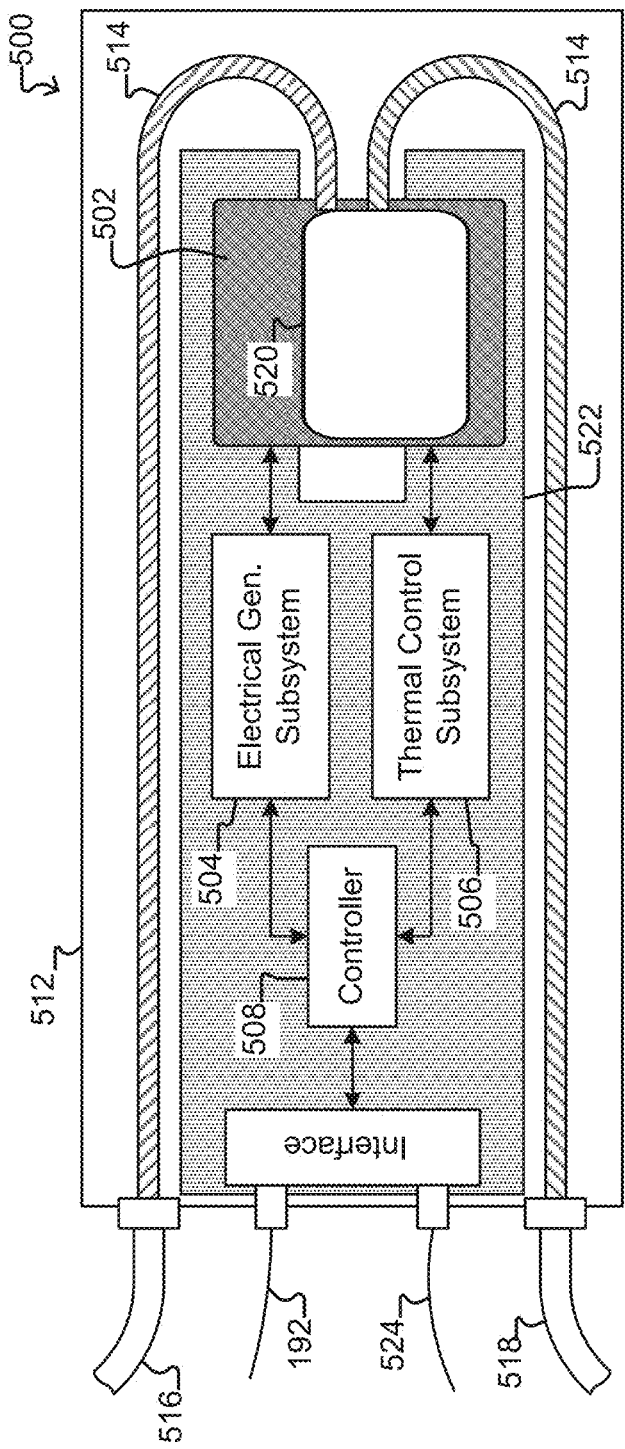
FIG. 5A illustrates a system for use with a microfluidic device and associated control equipment according to some embodiments of the disclosure.

Nest. Turning now to FIG. 5A, the system 150 can include a structure (also referred to as a "nest") 500 configured to hold a microfluidic device 520, which may be like microfluidic device 100, 200, or any other microfluidic device described herein. The nest 500 can include a socket 502 capable of interfacing with the microfluidic device 520 (e.g., an optically-actuated electrokinetic device 100, 200, etc.) and providing electrical connections from power source 192 to microfluidic device 520. The nest 500 can further include an integrated electrical signal generation subsystem 504. The electrical signal generation subsystem 504 can be configured to supply a biasing voltage to socket 502 such that the biasing voltage is applied across a pair of electrodes in the microfluidic device 520 when it is being held by socket 502. Thus, the electrical signal generation subsystem 504 can be part of power source 192. The ability to apply a biasing voltage to microfluidic device 520 does not mean that a biasing voltage will be applied at all times when the microfluidic device 520 is held by the socket 502. Rather, in most cases, the biasing voltage will be applied intermittently, e.g., only as needed to facilitate the generation of electrokinetic forces, such as dielectrophoresis or electrowetting, in the microfluidic device 520.

As illustrated in FIG. 5A, the nest 500 can include a printed circuit board assembly (PCBA) 522. The electrical signal generation subsystem 504 can be mounted on and electrically integrated into the PCBA 522. The exemplary support includes socket 502 mounted on PCBA 522, as well.

In some embodiments, the nest 500 can comprise an electrical signal generation subsystem 504 configured to measure the amplified voltage at the microfluidic device 520 and then adjust its own output voltage as needed such that the measured voltage at the microfluidic device 520 is the desired value. In some embodiments, the waveform amplification circuit can have a +6.5V to −6.5V power supply generated by a pair of DC-DC converters mounted on the PCBA 322, resulting in a signal of up to 13 Vpp at the microfluidic device 520.

In certain embodiments, the nest 500 further comprises a controller 508, such as a microprocessor used to sense and/or control the electrical signal generation subsystem 504. Examples of suitable microprocessors include the Arduino™ microprocessors, such as the Arduino Nano™. The controller 508 may be used to perform functions and analysis or may communicate with an external master controller 154 (shown in FIG. 1A) to perform functions and analysis. In the embodiment illustrated in FIG. 3A the controller 308 communicates with the master controller 154 (of FIG. 1A) through an interface (e.g., a plug or connector).

As illustrated in FIG. 5A, the support structure 500 (e.g., nest) can further include a thermal control subsystem 506. The thermal control subsystem 506 can be configured to regulate the temperature of microfluidic device 520 held by the support structure 500. For example, the thermal control subsystem 506 can include a Peltier thermoelectric device (not shown) and a cooling unit (not shown). In the embodiment illustrated in FIG. 5A, the support structure 500 comprises an inlet 516 and an outlet 518 to receive cooled fluid from an external reservoir (not shown) of the cooling unit, introduce the cooled fluid into the fluidic path 514 and through the cooling block, and then return the cooled fluid to the external reservoir. In some embodiments, the Peltier thermoelectric device, the cooling unit, and/or the fluidic path 514 can be mounted on a casing 512 of the support structure 500. In some embodiments, the thermal control subsystem 506 is configured to regulate the temperature of the Peltier thermoelectric device so as to achieve a target temperature for the microfluidic device 520. Temperature regulation of the Peltier thermoelectric device can be achieved, for example, by a thermoelectric power supply, such as a Pololu™ thermoelectric power supply (Pololu Robotics and Electronics Corp.). The thermal control subsystem 506 can include a feedback circuit, such as a temperature value provided by an analog circuit. Alternatively, the feedback circuit can be provided by a digital circuit.

The nest 500 can include a serial port 524 which allows the microprocessor of the controller 508 to communicate with an external master controller 154 via the interface. In addition, the microprocessor of the controller 508 can communicate (e.g., via a Plink tool (not shown)) with the electrical signal generation subsystem 504 and thermal control subsystem 506. Thus, via the combination of the controller 508, the interface, and the serial port 524, the electrical signal generation subsystem 504 and the thermal control subsystem 506 can communicate with the external master controller 154. In this manner, the master controller 154 can, among other things, assist the electrical signal generation subsystem 504 by performing scaling calculations for output voltage adjustments. A Graphical User Interface (GUI) (not shown) provided via a display device 170 coupled to the external master controller 154, can be configured to plot temperature and waveform data obtained from the thermal control subsystem 506 and the electrical signal generation subsystem 504, respectively. Alternatively, or in addition, the GUI can allow for updates to the controller 508, the thermal control subsystem 506, and the electrical signal generation subsystem 504.

Figure 5B:
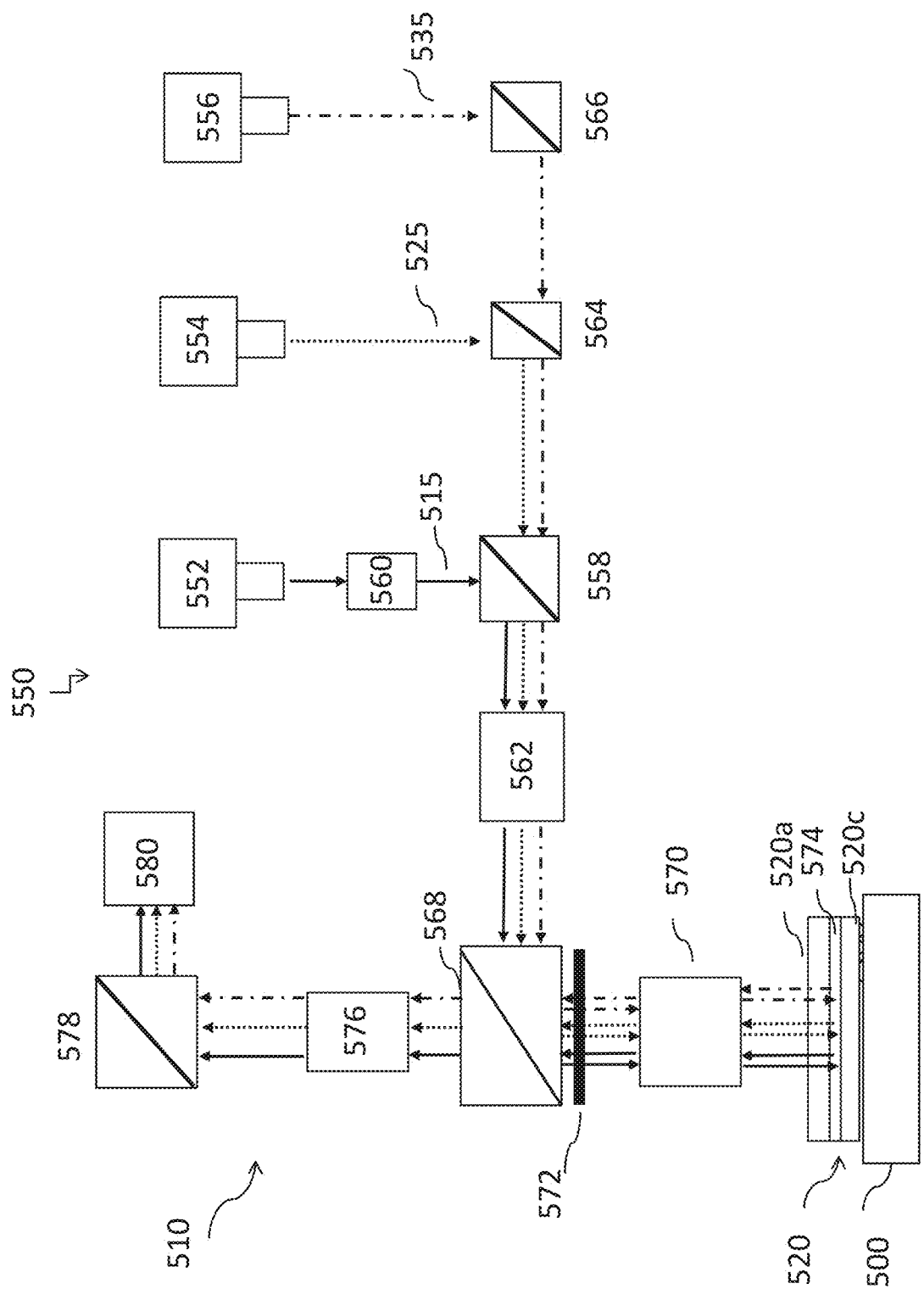
FIG. 5B illustrates an imaging device according to some embodiments of the disclosure.

Optical sub-system. FIG. 5B is a schematic of an optical sub-system 550 having an optical apparatus 510 for imaging and manipulating micro-objects in a microfluidic device 520, which can be any microfluidic device described herein. The optical apparatus 510 can be configured to perform imaging, analysis and manipulation of one or more micro-objects within the enclosure of the microfluidic device 520.

The optical apparatus 510 may have a first light source 552, a second light source 554, and a third light source 556. The first light source 552 can transmit light to a structured light modulator 560, which can include a digital mirror device (DMD) or a microshutter array system (MSA), either of which can be configured to receive light from the first light source 552 and selectively transmit a subset of the received light into the optical apparatus 510. Alternatively, the structured light modulator 560 can include a device that produces its own light (and thus dispenses with the need for a light source 552), such as an organic light emitting diode display (OLED), a liquid crystal on silicon (LCOS) device, a ferroelectric liquid crystal on silicon device (FLCOS), or a transmissive liquid crystal display (LCD). The structured light modulator 560 can be, for example, a projector. Thus, the structured light modulator 560 can be capable of emitting both structured and unstructured light. In certain embodiments, an imaging module and/or motive module of the system can control the structured light modulator 560.

In embodiments when the structured light modulator 560 includes a mirror, the modulator can have a plurality of mirrors. Each mirror of the plurality of mirrors can have a size of about 5 microns×5 microns to about 10 microns×10 microns, or any values therebetween. The structured light modulator 560 can include an array of mirrors (or pixels) that is 2000×1000, 2580×1600, 3000×2000, or any values therebetween. In some embodiments, only a portion of an illumination area of the structured light modulator 560 is used. The structured light modulator 560 can transmit the selected subset of light to a first dichroic beam splitter 558, which can reflect this light to a first tube lens 562.

The first tube lens 562 can have a large clear aperture, for example, a diameter larger than about 40 mm to about 50 mm, or more, providing a large field of view. Thus, the first tube lens 5621 can have an aperture that is large enough to capture all (or substantially all) of the light beams emanating from the structured light modulator 560.

The structured light 515 having a wavelength of about 400 nm to about 710 nm, may alternatively or in addition, provide fluorescent excitation illumination to the microfluidic device.

The second light source 554 may provide unstructured brightfield illumination. The brightfield illumination light 525 may have any suitable wavelength, and in some embodiments, may have a wavelength of about 400 nm to about 760 nm. The second light source 554 can transmit light to a second dichroic beam splitter 564 (which also may receive light 535 from the third light source 556), and the second light, brightfield illumination 525, may be transmitted therefrom to the first dichroic beam splitter 558. The second light, brightfield illumination 525, may then be transmitted from the first beam splitter 558 to the first tube lens 562.

The third light source 556 can transmit light through a matched pair relay lens (not shown) to a mirror 566. The third light illumination 535 may therefrom be reflected to the second dichroic beam splitter 5338 and be transmitted therefrom to the first beam splitter 5338, and onward to the first tube lens 5381. The third illumination light 535 may be a laser and may have any suitable wavelength. In some embodiments, the laser illumination 535 may have a wavelength of about 350 nm to about 900 nm. The laser illumination 535 may be configured to heat portions of one or more sequestration pens within the microfluidic device. The laser illumination 535 may be configured to heat fluidic medium, a micro-object, a wall or a portion of a wall of a sequestration pen, a metal target disposed within a microfluidic channel or sequestration pen of the microfluidic channel, or a photoreversible physical barrier within the microfluidic device, and described in more detail in U. S. Application Publication Nos. 2017/0165667 (Beaumont, et al.) and 2018/0298318 (Kurz, et al.), each of which disclosure is herein incorporated by reference in its entirety. In other embodiments, the laser illumination 535 may be configured to initiate photocleavage of surface modifying moieties of a modified surface of the microfluidic device or photocleavage of moieties providing adherent functionalities for micro-objects within a sequestration pen within the microfluidic device. Further details of photocleavage using a laser may be found in International Application Publication No. WO2017/205830 (Lowe, Jr. et al.), which disclosure is herein incorporated by reference in its entirety.

The light from the first, second, and third light sources (552, 554, 5560) passes through the first tube lens 562 and is transmitted to a third dichroic beam splitter 568 and filter changer 572. The third dichroic beam splitter 568 can reflect a portion of the light and transmit the light through one or more filters in the filter changer 572 and to the objective 570, which may be an objective changer with a plurality of different objectives that can be switched on demand. Some of the light (515, 525, and/or 535) may pass through the third dichroic beam splitter 568 and be terminated or absorbed by a beam block (not shown). The light reflected from the third dichroic beam splitter 568 passes through the objective 570 to illuminate the sample plane 574, which can be a portion of a microfluidic device 520 such as the sequestration pens described herein.

The nest 500, as described in FIG. 5A, can be integrated with the optical apparatus 510 and be a part of the apparatus 510. The nest 500 can provide electrical connection to the enclosure and be further configured to provide fluidic connections to the enclosure. Users may load the microfluidic apparatus 520 into the nest 500. In some other embodiments, the nest 500 can be a separate component independent of the optical apparatus 510.

Light can be reflected off and/or emitted from the sample plane 574 to pass back through the objective 570, through the filter changer 572, and through the third dichroic beam splitter 568 to a second tube lens 576. The light can pass through the second tube lens 576 (or imaging tube lens 576) and be reflected from a mirror 578 to an imaging sensor 580. Stray light baffles (not shown) can be placed between the first tube lens 562 and the third dichroic beam splitter 568, between the third dichroic beam splitter 568 and the second tube lens 576, and between the second tube lens 576 and the imaging sensor 580.

Objective. The optical apparatus can comprise the objective lens 570 that is specifically designed and configured for viewing and manipulating of micro-objects in the microfluidic device 520. For example, conventional microscope objective lenses are designed to view micro-objects on a slide or through 5 mm of aqueous fluid, while micro-objects in the microfluidic device 520 are inside the plurality of sequestration pens within the viewing plane 574 which have a depth of 20, 30, 40, 50, 60 70, 80 microns or any values therebetween. In some embodiments, a transparent cover 520a, for example, glass or ITO cover with a thickness of about 750 microns, can be placed on top of the plurality of sequestration pens, which are disposed above a microfluidic substrate 520c. Thus, the images of the micro-objects obtained by using the conventional microscope objective lenses may have large aberrations such as spherical and chromatic aberrations, which can degrade the quality of the images. The objective lens 570 of the optical apparatus 510 can be configured to correct the spherical and chromatic aberrations in the optical apparatus 1350. The objective lens 570 can have one or more magnification levels available such as, 4×, 10×, 20×.

Modes of illumination. In some embodiments, the structured light modulator 560 can be configured to modulate light beams received from the first light source 552 and transmits a plurality of illumination light beams 515, which are structured light beams, into the enclosure of the microfluidic device, e.g., the region containing the sequestration pens. The structured light beams can comprise the plurality of illumination light beams. The plurality of illumination light beams can be selectively activated to generate a plurality of illuminations patterns. In some embodiments, the structured light modulator 560 can be configured to generate an illumination pattern, similarly as described for FIGS. 4A-4B, which can be moved and adjusted. The optical apparatus 560 can further comprise a control unit (not shown) which is configured to adjust the illumination pattern to selectively activate the one or more of the plurality of DEP electrodes of a substrate 520c and generate DEP forces to move the one or more micro-objects inside the plurality of sequestration pens within the microfluidic device 520. For example, the plurality of illuminations patterns can be adjusted over time in a controlled manner to manipulate the micro-objects in the microfluidic device 520. Each of the plurality of illumination patterns can be shifted to shift the location of the DEP force generated and to move the structured light for one position to another in order to move the micro-objects within the enclosure of the microfluidic apparatus 520.

In some embodiments, the optical apparatus 510 may be configured such that each of the plurality of sequestration pens in the sample plane 574 within the field of view is simultaneously in focus at the image sensor 580 and at the structured light modulator 560. In some embodiments, the structured light modulator 560 can be disposed at a conjugate plane of the image sensor 580. In various embodiments, the optical apparatus 510 can have a confocal configuration or confocal property. The optical apparatus 510 can be further configured such that only each interior area of the flow region and/or each of the plurality of sequestration pens in the sample plane 574 within the field of view is imaged onto the image sensor 580 in order to reduce overall noise to thereby increase the contrast and resolution of the image.

In some embodiments, the first tube lens 562 can be configured to generate collimated light beams and transmit the collimated light beams to the objective lens 570. The objective 570 can receive the collimated light beams from the first tube lens 562 and focus the collimated light beams into each interior area of the flow region and each of the plurality of sequestration pens in the sample plane 574 within the field of view of the image sensor 580 or the optical apparatus 510. In some embodiments, the first tube lens 562 can be configured to generate a plurality of collimated light beams and transmit the plurality of collimated light beams to the objective lens 570. The objective 570 can receive the plurality of collimated light beams from the first tube lens 562 and converge the plurality of collimated light beams into each of the plurality of sequestration pens in the sample plane 574 within the field of view of the image sensor 580 or the optical apparatus 510.

In some embodiments, the optical apparatus 510 can be configured to illuminate the at least a portion of sequestration pens with a plurality of illumination spots. The objective 570 can receive the plurality of collimated light beams from the first tube lens 562 and project the plurality of illumination spots, which may form an illumination pattern, into each of the plurality of sequestration pens in the sample plane 574 within the field of view. For example, each of the plurality of illumination spots can have a size of about 5 microns×5 microns; 10 microns×10 microns; 10 microns× 30 microns, 30 microns×60 microns, 40 microns×40 microns, 40 microns×60 microns, 60 microns×120 microns, 80 microns×100 microns, 100 microns×140 microns and any values there between. The illumination spots may individually have a shape that is circular, square, or rectangular. Alternatively, the illumination spots may be grouped within a plurality of illumination spots (e.g., an illumination pattern) to form a larger polygonal shape such as a rectangle, square, or wedge shape. The illumination pattern may enclose (e.g., surround) an unilluminated space that may be square, rectangular or polygonal. For example, each of the plurality of illumination spots can have an area of about 150 to about 3000, about 4000 to about 10000, or 5000 to about 15000 square microns. An illumination pattern may have an area of about 1000 to about 8000, about 4000 to about 10000, 7000 to about 20000, 8000 to about 22000, 10000 to about 25000 square microns and any values there between.

The optical system 510 may be used to determine how to reposition micro-objects and into and out of the sequestration pens of the microfluidic device, as well as to count the number of micro-objects present within the microfluidic circuit of the device. Further details of repositioning and counting micro-objects are found in U. S. Application Publication No. 2016/0160259 (Du); U.S. Pat. No. 9,996,920 (Du et al.); and International Application Publication No. WO2017/102748 (Kim, et al.). The optical system 510 may also be employed in assay methods to determine concentrations of reagents/assay products, and further details are found in U.S. Pat. No. 8,921,055 (Chapman), U.S. Pat. No. 10,010,882 (White et al.), and U.S. Pat. No. 9,889,445 (Chapman et al.); International Application Publication No. WO2017/181135 (Lionberger, et al.); and International Application Serial No. PCT/US2018/055918 (Lionberger, et al.). Further details of the features of optical apparatuses suitable for use within a system for observing and manipulating micro-objects within a microfluidic device, as described herein, may be found in WO2018/102747 (Lundquist, et al), the disclosure of which is herein incorporated by reference in its entirety.

Additional system components for maintenance of viability of cells within the sequestration pens of the microfluidic device. In order to promote growth and/or expansion of cell populations, environmental conditions conducive to maintaining functional cells may be provided by additional components of the system. For example, such additional components can provide nutrients, cell growth signaling species, pH modulation, gas exchange, temperature control, and removal of waste products from cells.

EXAMPLES

General Materials and Methods.

System and Microfluidic device: An OptoSelect™ nanofluidic chip (Berkeley Lights, Inc.) was used with the BEACON® optofluidic instrument (Berkeley Lights, Inc.). The instrument included: a mounting stage for the chip coupled to a temperature controller; a pump and fluid medium conditioning component; and an optical train including a camera and a structured light source suitable for activating phototransistors within the chip. The OptoSelect™ chip included a substrate configured with OptoElectroPositioning (OEP™) technology, which provides a phototransistor-activated DEP force. The chip also included a plurality of microfluidic channels, each having a plurality of NanoPen™ chambers (or sequestration pens) fluidically connected thereto. The volume of each sequestration pen was around $1 \times 10^6$ cubic microns.

Priming solution: Complete growth medium containing 0.1% Pluronic® F127 ((Life Technologies® Cat #P6866).

Preparation for culturing: The microfluidic device having a modified surface was loaded onto the system and purged with 100% carbon dioxide at 15 psi for 5 min. Immediately following the carbon dioxide purge, the priming solution was perfused through the microfluidic device at 5 microliters/see for 8 min. Culture medium was then flowed through the microfluidic device at 5 microliters/see for 5 min.

Priming regime. 250 microliters of 100% carbon dioxide was flowed in at a rate of 12 microliters/sec. This was followed by 250 microliters of PBS containing 0.1% Pluronic® F27 (Life Technologies® Cat #P6866), flowed in at 12 microliters/sec. The final step of priming included 250 microliters of PBS, flowed in at 12 microliters/sec. Introduction of the culture medium follows.

Perfusion regime. The perfusion method was either of the following two methods:

1. Perfuse at 0.01 microliters/see for 2 h; perfuse at 2 microliters/see for 64 sec; and repeat.
2. Perfuse at 0.02 microliters/see for 100 sec; stop flow 500 sec; perfuse at 2 microliters/see for 64 sec; and repeat.

Figure 7A:
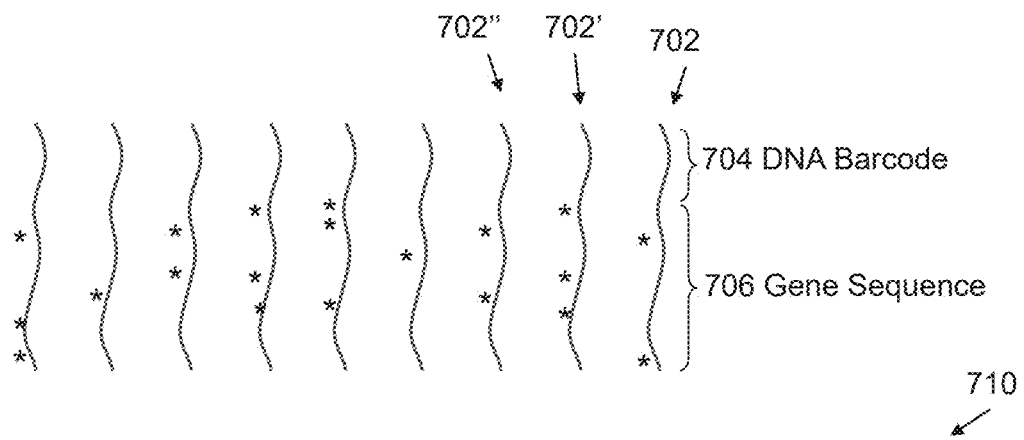
FIGS. 7A-7D illustrate a process for rapid protein evolution according to some embodiments of the disclosure.
Figure 7A:
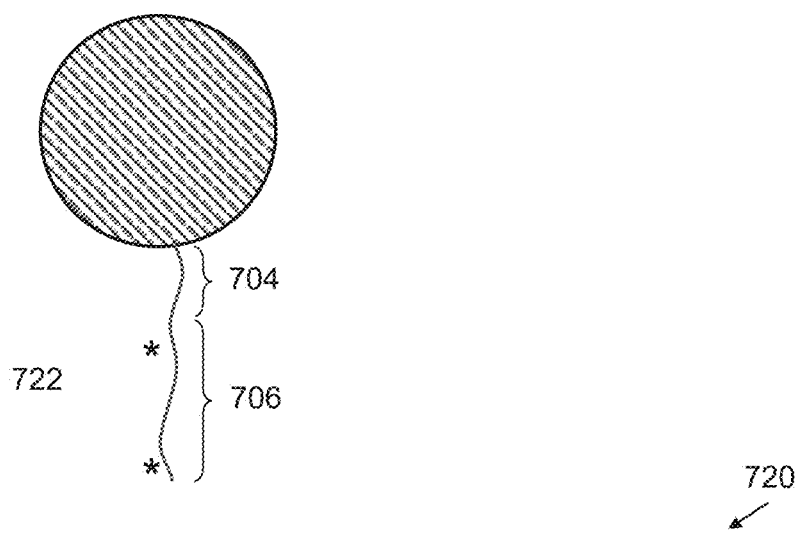

Experiment 1. Amylase Engineering. Turning to FIG. 7A, Boxes 710, 720 show design and construction of a nucleic acid library including nucleic acid sequences 702, 702', 702" introducing individual nucleic acid variations at one or more nucleic acid sites along the length of the gene sequence 706 encoding for Amylase. In other embodiments, the nucleic acid substitutions may be restricted to a portion of the gene sequence encoding for Amylase. For example, the substitutions may be restricted to the portion of the gene sequence that encodes the enzymatic active site of Amylase. The nucleic acid sequences may be designed manually, may be random, or may be selected by a computer-based algorithm. Any of these design processes 710 may be performed within the methods described herein. A DNA synthesis component such as a DNA writer (e.g., a Gen9 system, GeneArt, or the like) or DNA parallel synthesis system with off-machine ligation of smaller units may produce the gene-length variant sequences in box 720. The variant nucleic acid sequences may be produced already containing a nucleic acid sequence comprising a barcode 704 that may be constructed and detected as described in International Patent Application No. PCT/US2017/054628 filed on Sep. 29, 2017, entitled "DNA Barcode Compositions and Methods of In Situ Identification in a Microfluidic Device", and incorporated by reference herein for all purposes in its entirety. However, any suitable alternative barcode sequence 704 that may be detected by the hybridization flow method described in PCT/US2017/054628 may be used.

In another alternative, the barcode sequence may be determined by selectively exporting the nucleic acid labelled bead and sequencing the nucleic acid sequence of each bead rather than detecting it visually. In that alternative type of barcode determination, the variant nucleic acid sequence may also be determined by sequencing as well, and the variant nucleic acid sequence correlated to the phenotypic reporter readout by the known location.

After synthesis of the nucleic acid library, each different nucleic acid sequence is attached to a bead, which may be performed with the barcode already incorporated within each individual nucleic acid sequence or each different nucleic acid sequence may be attached via ligation to a unique barcode already attached to the individual bead, as part of Box 720. This may be performed within a nucleic acid synthesis component or may be performed by a separate instrument from the nucleic acid synthesis component. The barcode sequence is now identified with the specific nucleic acid variant sequence of the nucleic acid labeled bead 722, and this information may be stored in the memory of the computing component(s).

Figure 7B:
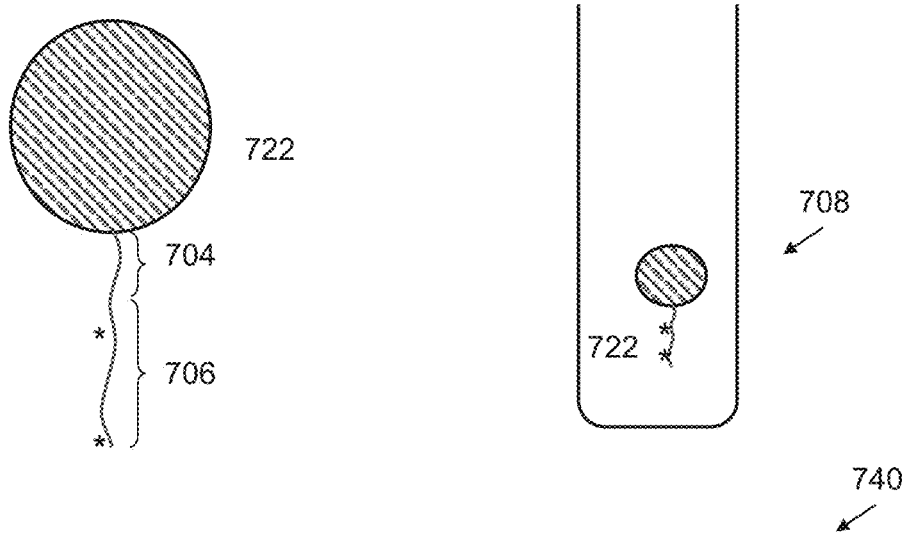
Figure 7B:
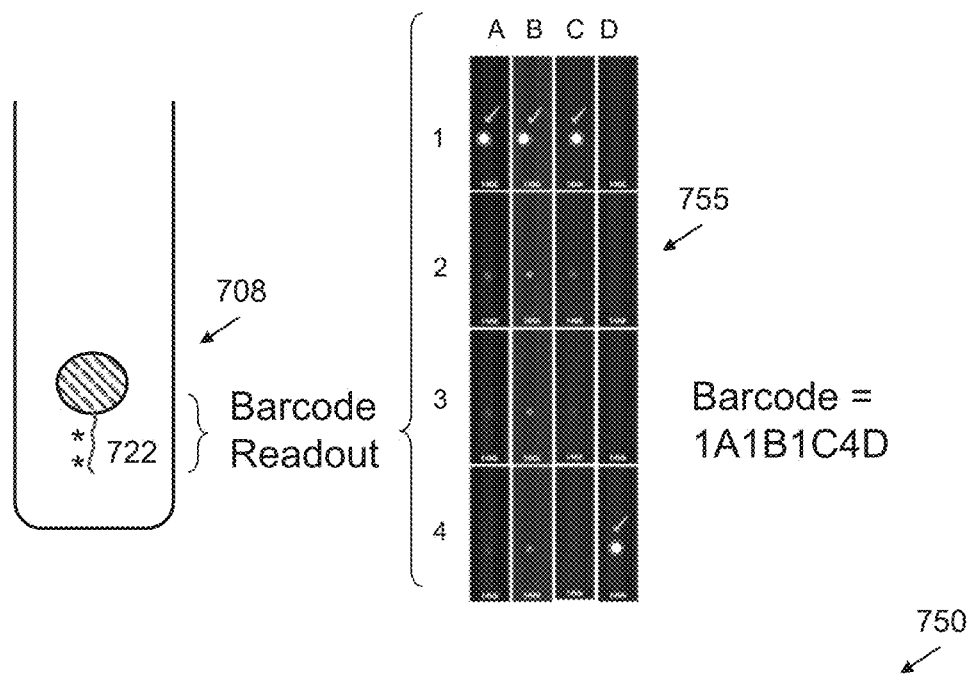

The bead-bound barcoded library of variant nucleic acid sequences is then imported into a microfluidic device having an enclosure, as described at Box 730 of FIG. 7A. In this experiment, the microfluidic device is a device as described in the general materials section above, but is not so limited. In this example, the nucleic acid bearing beads are introduced into a channel of the microfluidic device. The nucleic acid labeled beads including individual labeled bead 722 of FIG. 7A are then introduced into an unswept region 708 of the microfluidic device. In this example, the unswept region is an isolation region of a sequestration pen, which may be any sequestration pen as described herein. (See Box 740 of FIG. 7B). The introduction of a single bead 722 into the isolation region 708 of a sequestration pen may be accomplished using optically actuated dielectrophoresis or may be accomplished using other forces such as local fluidic flow actuation, magnetic forces or gravity.

Box 750 of FIG. 5B, shows determining the barcode of the bead 722 may be performed via introducing successive flows of fluorescent tagging agent into the flow channel of the microfluidic device, as described in PCT/US2017/054628. The result is shown for bead 722 in panel 755. Panel 755 is a photographic record of each flow of fluorescently labeled hybridization reagents, denoting which short barcode segment is present in the isolation region 708. For example, in the first flow of fluorescently tagged reagents, labeled as "1" along the left hand side of panel 755, four spectrally distinct hybridization sequences are permitted to diffuse from the microfluidic channel into the unswept region 708. For bead 722, each of the hybridization sequences of the A, B and C fluorescent detection channel is able to bind to the barcode sequence 704 of bead 722, while the hybridization reagent of the D fluorescent channel does not bind. In flows 2 and 3, four different and differentially fluorescently labeled hybridization probes are similarly introduced, but neither flow contains a hybridization probe that can bind to the remaining unidentified section of the barcode, which is captured in channel D. Finally, in flow 4, a hybridization reagent labeled in the D channel is introduced which is capable of binding to bead 722, and produces a fluorescent signal in the D channel. In this example, the barcode 704 of bead 722 has a sequence that is complementary to the sequence 1A1B1C4D of the hybridization probes. This visual detection can alternatively be performed at a later point it the experiment, but it is often convenient to identify the location of each specific barcode at the beginning of the experiment. This permits accurate identification of the location of a specific bead and the specific variant nucleic acid sequence it bears.

Box 760 of FIG. 5C shows introduction of a phenotypic reporter micro-object 724 into the sequestration pen, in proximity to the bead 722 within the isolation region of the sequestration pen, which is an unswept region 708. The phenotypic reporter micro-object 724 may be disposed within the isolation region of the sequestration pen. For this example, the phenotypic reporter micro-object 724 may be a bead comprising substrate which may be used in an Amylase assay or may not require a micro-object but may be a solution phase reagent such as EnzChek™ Ultra Amylase Assay (ThermoFisher Cat. No. E33651) in combination with a Ni-NTA magnetic bead-based assay using His6 tagged affinity tags.

Figure 7C:
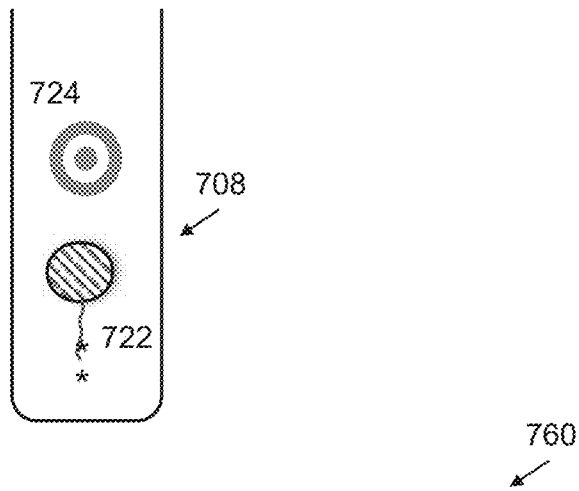
Figure 7C:
Figure 7C:
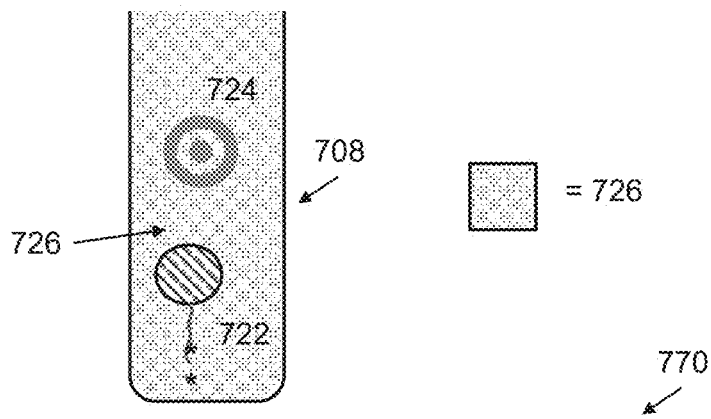

Box 770 of FIG. 7C shows the introduction of a reagent mixture 726 which may permit protein expression from the individual variant nucleic acid present on bead 722. This may be a cell free protein expression systems. As this reagent is a solution, it is introduced into the flow path of the channel of the microfluidic device and can diffuse into the isolation region of the sequestration pen.

Figure 7D:
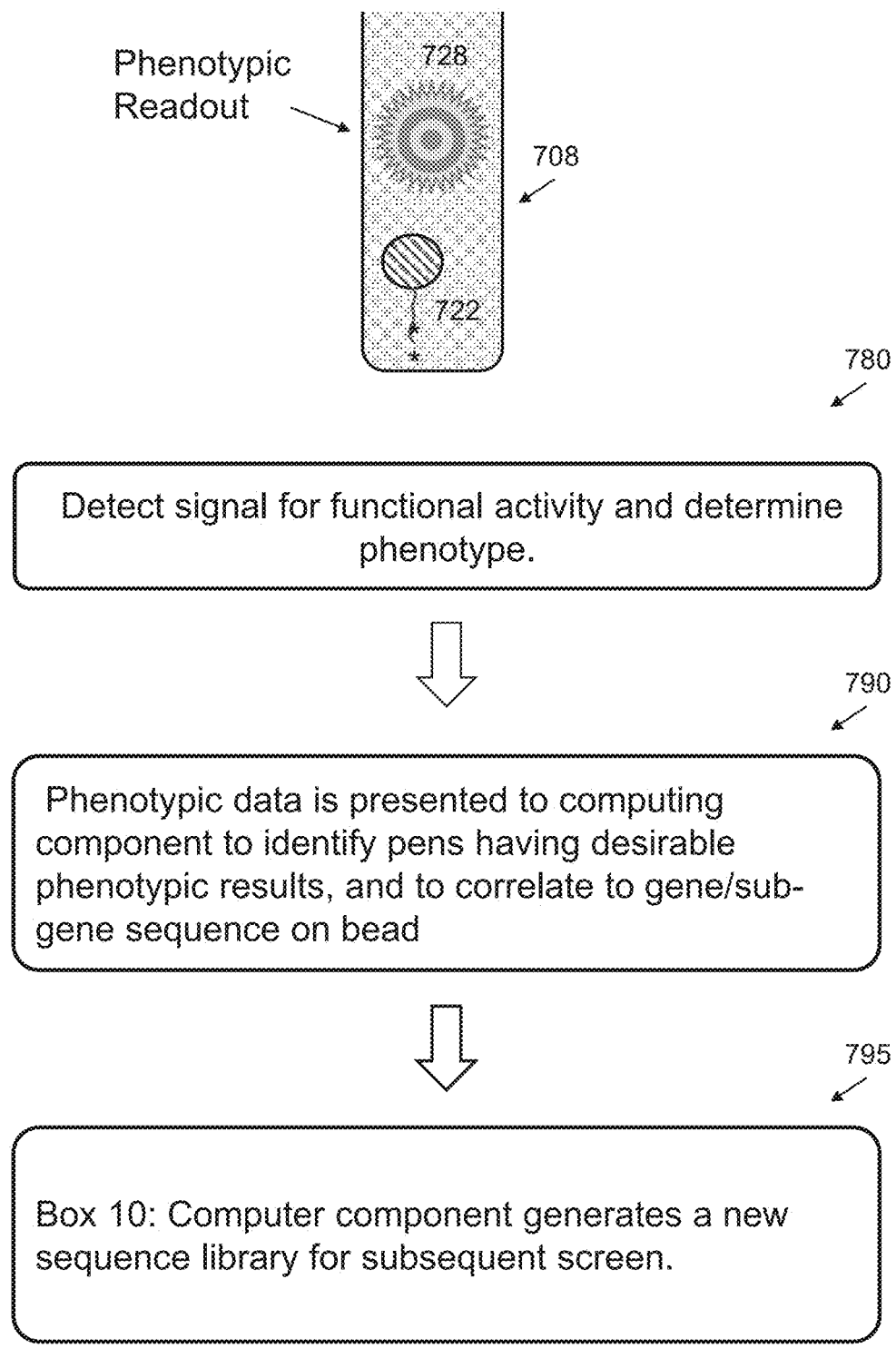

Box 780 of FIG. 7D shows the commencement of protein expression, and in the presence of the phenotype reporter, a signal 728 is detected for functional activity, and may be quantified. For example, the amount of signal detected by the enzymatic amylase assay may be divided by the results of a fluorescent His6 tagged affinity assay to provide a quantified level of function for the individual nucleic acid sequence of bead 722, providing the phenotypic readout. In some variations, a protein aggregation micro-object may also be present in each isolation region, proximal to the nucleic acid-labeled bead, which may capture expressed protein by capturing a protein aggregation tag included in the expressed protein, such as an epitope tag or a polyhistidine tag, thus concentrating expressed protein within the isolation region 708. The captured expressed protein is still capable of functioning in the functional assay and producing the signal 728.

Box 790 of FIG. 7D presents the phenotypic data to the computing component to identify pens having desirable phenotypic results and then correlates those results to the variant nucleic acid (gene or subgene) sequence present on bead 722, which is available from the stored correlation of variant nucleic acid sequence with the detected/determined barcode sequence.

Box 795 of FIG. 7D presents the correlation of phenotypic results with sequence to the same or different computing component, which uses those results to generate a new (second and further numbers of cycles) nucleic acid sequence library to continue to improve the phenotypic results in a succeeding round of experiments. The computing component may utilize an algorithm to generate the second nucleic acid sequence library. This method may also be performed manually, but the speed of the computing component can permit more rapid iteration of design 901/build 920 (synthesis)/test 930/learn 940 cycle of this method as shown in FIG. 9. Each portion of the cycle may be optimized to permit a cycle to be performed within a 24 hr period, permitting rapid protein evolution in the pursuit of novel, high functioning proteins.

Experiment 2. Antibody Engineering. The experiment may be performed similarly to Experiment 1, except that the phenotypic reporter may include an antibody functional assay such as a ligand blocking assay, a Green-fluorescent protein expression assay, or the like. The antibody can, for example, be a therapeutic antibody and/or may be a single chain antibody, e.g., having no disulfide bonds; a nanobody, e.g., a heavy chain antibody from a camelid species; or a single chain variable fragment; optionally having no sugar modifications. The concentration of the antibody may be determined, for example, as described in International Patent Application No. PCT/US2017/027795, filed on Apr. 14, 2017, entitled "Method, Systems, and Kits for In-Pen Assays", which is herein incorporated by reference for all purposes in its entirety. The phenotype reported out may be based on the functional assay or a combination of the functional assay and the concentration of the therapeutic antibody as defined by the in pen assay of PCT/US2017/027795.

Figure 8:
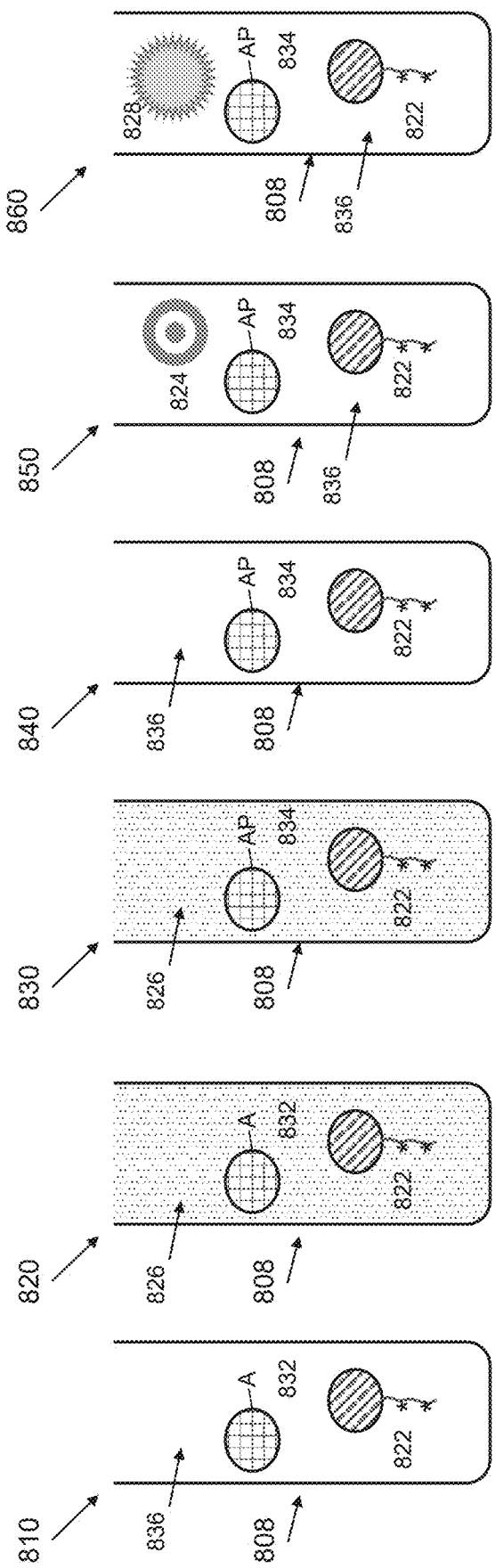
FIG. 8 illustrates a process for rapid protein evolution according to some embodiments of the disclosure.

Experiment 3. Amylase Engineering. Another method of performing a rapid protein evolution experiment is shown in FIG. 8. Nucleic acid labeled bead 822, which may be like nucleic acid bead 722, 622 and contains at least a barcode sequence and a variant nucleic acid sequence, is introduced into an unswept region 808, as shown at point 810 of FIG. 8, which may be an isolation region of a sequestration pen of the microfluidic device. The liquid medium 836 is any suitable liquid medium, which permits maintenance of the nucleic acid labeled bead 822 and other components of the assay. The nucleic acid sequence may further include a suitable promoter sequence permitting protein translation by a cell free expression system, which may be any suitable cell free expression system for producing amylase, as is known in the art. In some variations, the nucleic acid sequence may also include an adapter sequence configured to adapt the nucleic acid sequence of the barcode to be determined by sequencing by synthesis, or any highly parallel sequencing method. A protein aggregation bead 832 is also introduced into the isolation region 808, and is disposed proximal to the nucleic acid labeled bead 822.

At point 820 of FIG. 8, a reagent mixture 826 which may permit protein expression from the individual variant nucleic acid present on bead 822 is introduced into the microfluidic device and is permitted to diffuse into the unswept region 808. This may be a cell free protein expression system, as mentioned above. As protein is produced at point 830, it is captured to the protein aggregation bead, using any suitable protein tag included in the expressed protein. This is shown as protein ("P") captured to bead 834, thus concentrating expressed protein within the isolation region 808.

At point 840, sufficient protein has been produced. The reagent mixture 826 is displaced by introduction of fresh liquid medium 836, which diffuses into the isolation region 808, and not displacing nucleic acid bead 822 or protein labeled aggregation bead 834.

At point 850, a phenotypic reporter 824 is introduced into the isolation region 808, and disposed proximal to the protein-labeled aggregation bead 834.

At point 860, similarly to Experiment 1, a functional assay may be performed and the phenotypic reporter may produce a detectable signal 828, which may be quantifiable. The detected signal 828 is stored in memory and correlated to the location of the isolation region 808 of a specific sequestration pen of the microfluidic device.

Detection of the barcode of the nucleic acid labeled bead 822 may be performed in several ways and at several points. Detection may be made visually, as described above. When detection of the barcode is made visually, the visual detection can take place at any of points 810, 840, 850, 860. It may be less typically performed at points 820, 830, but detection may still be made.

In other variations, determination of the barcode may be made by sequencing the barcode nucleic acid sequence. This may be accomplished by exporting the nucleic acid labelled bead 822 selectively from a known location 808 within the microfluidic device, and sequencing the barcode sequence of one or more beads using any massively parallel sequencing method. The known location 808 may be stored in memory, and correlated with the sequence detected visually/determined by sequencing. The phenotype reporter assay result from the known location may be correlated with the detected barcode/sequence.

In some variations, the barcode sequence is previously correlated with the variant nucleic acid sequence during synthesis of the nucleic acid labeled bead, and the barcode/sequence correlation stored in memory. Sequencing the nucleic acid sequence of the labeled bead may then only require sequencing of the barcode itself. In other variations, the sequence of the variant nucleic acid sequence is obtained at the same time as the barcode sequence, and correlated to the phenotype readout resulting from that variant nucleic acid sequence.

In any case, nucleic acid labeled bead 822 may be exported for determination of the barcode sequence and/or the variant nucleic acid sequence at various points illustrated in FIG. 8. Typically, bead 822 may be exported selectively at any of points 840, 850, 860.

Additionally, protein-labelled protein aggregation bead 834 may be exported from the unswept region 808, e.g., isolation region of a sequestration pen, after the phenotypic reporter readout has been made. Bead 834 may be exported to retest in a second round of phenotypic reporter readout or be tested in another assay or type of analysis.

The correlation of the phenotypic results with variant nucleic sequence is then presented to the same or different computing component, as described above in Experiment 1, o generate a new set of further variant nucleic acid sequences, forming a second nucleic acid labeled bead library to continue to improve the phenotypic results in a succeeding round of experiments.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

LIST OF SOME EMBODIMENTS OF THE DISCLOSURE

1. A system for rapid protein evolution, including: a microfluidic device; and a microfluidic system component (e.g., instrument) configured to: import a plurality of beads into the microfluidic device, each bead of the plurality including (i) one nucleic acid sequence of a first plurality of nucleic acid sequences, and (ii) a barcode, wherein each nucleic acid sequence of the first plurality of nucleic acid sequences encodes for a sequence variant of a protein of interest (e.g., an original protein sequence of interest, which may be a naturally occurring protein of interest or a non-naturally occurring protein, in either case optionally having a defined activity); incubate the plurality of beads located within the microfluidic device under conditions conducive to expression of a corresponding protein encoded by the one nucleic acid sequence of each bead of the plurality of beads, thereby producing a plurality of corresponding proteins; and assay for a desired property in the plurality of corresponding proteins produced from the nucleic acid sequences of the plurality of beads.

2. The system of embodiment 1, further including a plurality of protein aggregation beads which specifically bind to an epitope of the protein of interest.

3. The system of embodiment 1, further including a plurality of protein aggregation beads which specifically bind to an epitope tags (e.g., a FLAG-tag, a metal chelating tag like His6, FlASH, ReAsH, or the like).

4. The system of any one of embodiments 1 to 3, further including a nucleic acid synthesis component configured to synthesize the first plurality of nucleic acid sequences (e.g., and, generally, any plurality of nucleic acid sequences, including subsequent pluralities of nucleic acids).

5. The system of any one of embodiments 1 to 4, wherein the system further includes a bead preparation component configured to connect a nucleic acid sequence to a bead (e.g., each nucleic acid sequence of the first plurality of nucleic acid sequences can be connected to a bead, thereby generating the first plurality of beads; more generally, any plurality of beads can be thus generated, including any subsequent plurality of beads).

6. The system of embodiment 5, wherein the bead preparation component is a separate apparatus from the nucleic acid synthesis component.

7. The system of any one of embodiments 1 to 6, further including a barcode detection component, configured to correlate the nucleic acid sequence of each bead of the plurality of beads with the location of the corresponding bead of the plurality of beads within the microfluidic device.

8. The system of embodiment 7, wherein the barcode detection component includes an optical subsystem of the microfluidic system component, configured to detect the barcode visually.

9. The system of embodiment 7, wherein the barcode detection component includes a nucleic acids sequencing component configured to determine the barcode by sequencing.

10. The system of any one of embodiments 1 to 9, further including a computational component (e.g., computer) configured to: correlate results from the desired property assay with individual nucleic acid sequences of the first plurality of nucleic acid sequences; and, based upon the correlation, design a second plurality of nucleic acid sequences, each encoding for a further sequence variant of the protein of interest.

11. The system of embodiment 10, wherein the computational component is further configured to communicate the design of the second plurality of nucleic acid sequences to the nucleic acids synthesis component.

12. The system of any one of embodiments 1 to 11, wherein the microfluidic device includes: a housing including a base and a microfluidic structure disposed on a surface of the base, wherein the base and the microfluidic structure define an interior chamber for holding a first liquid medium and micro-objects suspended therein.

13. The system of embodiment 12, wherein the microfluidic structure of the microfluidic device includes: a flow path for the first liquid medium; and a plurality of physical sequestration pens.

14. The system of embodiment 13, wherein each sequestration pen of the plurality includes: an enclosure; and a single opening to the flow path, and wherein the enclosure encloses an interior space structured to hold a micro-object suspended in a second liquid medium.

15. The system of embodiment 14, wherein each sequestration pen of the plurality further includes an inner wall extending from the opening into the enclosure.

16. The system of embodiment 14 or 15, wherein the opening of each sequestration pen of the plurality of sequestration pens of the microfluidic device is oriented such that no part is facing directly into the flow path, whereby, when the channel contains a flow of the first liquid medium and the sequestration pen contains the second liquid medium, a direct flow of the first liquid medium into the second liquid medium in the interior space is impeded while diffusive mixing of the first liquid medium with the second liquid medium in the interior space is allowed.

17. The system of any one of embodiments 14 to 16, wherein each sequestration pen of the plurality includes an isolation region and a connection region that fluidically connects the isolation region to the flow path, and wherein the isolation region is an unswept region in the microfluidic device.

18. The system of embodiment 17, wherein the connection region includes a proximal opening into the flow path having a width $W_{con}$ ranging from about 20 microns to about 100 microns and a distal opening into the isolation region, and wherein a length $L_{con}$ of the connection region from the proximal opening to the distal opening is as least 1.0 times the width $W_{con}$ of the proximal opening of the connection region.

19. The system of any one of embodiments 13 to 18, wherein the flow path includes a microfluidic channel, and wherein each sequestration pen of the plurality opens to the microfluidic channel.

20. The system of any one of embodiments 1 to 19, wherein the microfluidic device further includes a DEP configuration including: a first electrode; an electrode activation substrate; and a second electrode, wherein the first electrode is part of a first wall of the interior chamber and the electrode activation substrate and the second electrode are part of a second wall of the interior chamber, and wherein the electrode activation substrate comprises a photoconductive material, semiconductor integrated circuits, or phototransistors.

21. A process for evolving a protein, the process including: disposing a first library of nucleic acid sequences within a microfluidic device, wherein the microfluidic device includes: a housing including a base and a microfluidic structure disposed on a surface of the base, wherein the base and the microfluidic structure define an interior chamber for holding a first liquid medium and micro-objects suspended therein, and further wherein each nucleic acid sequence of the first library includes one or more variations from a nucleic acid sequence encoding a protein sequence of interest (e.g., an original protein sequence of interest, which may be a naturally occurring protein of interest or a non-naturally occurring protein, in either case optionally having a defined activity); introducing a phenotypic reporter into the microfluidic device and disposing it in proximity to each nucleic acid sequence of the first library, wherein the phenotypic reporter includes a solution phase reagent and/or a plurality of micro-objects, and is configured to provide a phenotypic readout from the protein sequence of interest; introducing a reagent mixture into the microfluidic device and disposing it in proximity to each nucleic acid sequence of the first library, wherein the reagent mixture is configured to express a corresponding protein sequence from each nucleic acid sequence of the first library; expressing the corresponding protein sequence from each nucleic acid sequence of the first library; detecting the phenotypic readout from a region proximal to one or more nucleic acid sequences of the first library; identifying individual nucleic acid sequences from the first library having a corresponding proximal region with a desired phenotypic readout; and determining the nucleotide sequence of the identified nucleic acid sequences of the first library.

22. The process of embodiment 21, further including: correlating the individual nucleic acid sequences of the first library with the phenotypic readout detected in the corresponding proximal regions; and designing a second library of nucleic acid sequences, wherein each nucleic acid sequence of the second library includes one or more variations from the nucleic acid sequence encoding the protein sequence of interest, the one or more variations of each nucleic acid sequence of the second library selected in light of the correlation.

23. The process of embodiment 21 or 22, wherein each nucleic acid sequence of the first library is linked to a corresponding bead of a first plurality of beads.

24. The process of embodiment 23, wherein each bead of the first plurality of beads includes a plurality of linked nucleic acids, each linked nucleic acid including the same variation of the nucleic acid sequence encoding the protein sequence of interest 25. The process of embodiment of any one of claims 21 to 24, wherein the process further includes: designing the nucleic acid sequences of the first library to vary from the nucleic acid sequence encoding the protein sequence of interest; synthesizing the nucleic acid sequences of the first library; and, optionally, connecting each nucleic acid sequence of the first library to a corresponding bead of the first plurality of beads, thereby forming a first library of nucleic acid bearing beads.

26. The process of any one of embodiments 23 to 25, wherein each bead of the first plurality of beads further includes a corresponding distinct barcode.

27. The process of embodiment 26, wherein the distinct barcodes include distinct nucleic acid sequences.

28. The process of embodiment 26 or 27, wherein the process further includes reading the barcode of each bead of the first plurality of beads after disposing the first library of nucleic acid sequences in the microfluidic device, thereby identifying a location of each bead and its corresponding nucleic acid sequence within the microfluidic device.

29. The process of embodiment 26 or 27, wherein the process further includes reading the barcode of each bead of the first plurality of beads (e.g., after detecting the phenotypic readout).

30. The process of any one of embodiments 21 to 29, wherein the process further includes: disposing a plurality of protein aggregation beads within the microfluidic device and disposing one or more protein aggregation beads of the plurality in proximity to each nucleic acid sequence of the first library, wherein the protein aggregation beads of the plurality specifically bind to (i) an epitope of the protein sequence of interest or (ii) a protein tag (e.g., an epitope tag) encoded by each nucleic acid sequence of the first library so as to functionally comprised by the corresponding protein sequence expressed therefrom.

31. The process of embodiment 30, further including capturing the corresponding protein expressed from each nucleic acid sequence of the first library to the one or more protein aggregation beads disposed in proximity thereto.

32. The process of embodiment 30 or 31, wherein the process further includes flowing a flushing medium through the microfluidic device after expressing the protein sequence, thereby displacing the reagent mixture, and wherein introducing the phenotypic reporter and disposing it in proximity to each nucleic acid of the first plurality is performed after flowing the flushing medium through the microfluidic device.

33. The process of embodiment 32, wherein flowing the flushing medium through the microfluidic device is performed before detecting the phenotypic reporter.

34. The process of any one of embodiments 21 to 33, wherein introducing the phenotypic reporter and disposing it in proximity to each nucleic acid of the first plurality is performed after disposing the reagent mixture in proximity to each nucleic acid sequence of the first library.

35. The process of any one of embodiments 21 to 34, wherein the microfluidic structure of the microfluidic device includes: (i) a flow path for the first liquid medium; and (ii) a plurality of physical sequestration pens.

36. The process of embodiment 35, wherein each sequestration pen of the plurality includes: an enclosure; and a single opening to the flow path; wherein the enclosure encloses an interior space structured to hold a biological micro-object suspended in a second liquid medium.

37. The process of embodiment 36, wherein each sequestration pen of the plurality further includes an inner wall extending from the opening into the enclosure.

38. The process of embodiment 36 or 37, wherein the opening of each sequestration pen of the plurality of sequestration pens of the microfluidic device is oriented such that no part is facing directly into the flow path, whereby, when the flow path contains a flow of the first liquid medium and the sequestration pen contains the second liquid medium, a direct flow of the first liquid medium into the second liquid medium in the interior space is impeded while diffusive mixing of the first liquid medium with the second liquid medium in the interior space is allowed.

39. The process of any one of embodiments 21 to 38, wherein the microfluidic device further includes a DEP configuration including: a first electrode; an electrode activation substrate; and a second electrode, wherein the first electrode is part of a first wall of the interior chamber and the electrode activation substrate and the second electrode are part of a second wall of the interior chamber, and wherein the electrode activation substrate comprises a photoconductive material, semiconductor integrated circuits, or phototransistors.

40. The process of any one of embodiments 35 to 38, wherein disposing the first library of nucleic acid sequences within the microfluidic device includes introducing individual beads of the first plurality of beads into individual sequestration pens of the plurality of sequestration pens.

41. The process of embodiment 40, wherein no more than one bead of the first plurality of beads is introduced into each sequestration pen of the plurality of sequestration pens.

42. The process of embodiment 40 or 41, wherein introducing the phenotypic reporter into the microfluidic device includes introducing one or more micro-objects of the plurality of micro-objects into individual sequestration pens containing a nucleic acid sequence of the first library of nucleic acid sequences.

43. The process of any one of embodiments 21 to 42, wherein the protein of interest includes an enzyme.

44. The process of any one of embodiments 21 to 42, wherein the protein of interest includes a domain which binds to a cell surface marker.

45. The process of embodiment 44, wherein the cell surface marker is a cell surface receptor (e.g., a receptor involved in intercellular signaling) or a glycoprotein.

46. The process of any one of embodiments 21 to 45, wherein the protein of interest includes an antibody (e.g., a single-chain antibody, a nanobody, or the like).

47. The process of any one of embodiments 210 to 46, wherein the phenotypic reporter includes a solution phase reagent providing a detectable signal when contacted by the protein of interest (e.g., the reagent could be cleaved by the protein of interest, and the cleavage could result in the emission of detectable light).

48. The process of any one of embodiments 21 to 46, wherein the phenotypic reporter includes micro-objects including binding sites for the protein of interest, reporter cells configured to report a function of the protein of interest, or micro-objects providing enzymatic substrates for an enzymatic activity of the protein of interest.

49. The process of any one of embodiments 21 to 48, wherein correlating the individual nucleic acid sequences of the first library with the phenotypic readout detected in the corresponding proximal regions is performed by a first computer component configured to identify a function of the expressed protein from the identified nucleic acid sequences that is more desirable than the function of the protein of interest.

50. The process of embodiment 49, wherein designing the second library of nucleic acid sequences is performed by a second computer component, based on the correlation of the expressed protein function with the nucleic acid sequences of the first library of nucleic acid sequences.

51. The process of embodiment 50, wherein the first computer component is the same as the second computer component.

52. The process of any one of embodiments 47 to 51, wherein the first computer component employs a machine learning algorithm to perform the correlation.

53. The process of any one of embodiments 47 to 52, wherein the second computer component employs a machine learning algorithm to design the second library of nucleic acid sequences.

54. The process of any one of embodiments 21 to 53, wherein the reagent mixture includes a cell free protein expression reaction mixture.

55. The process of any one of embodiments 35 to 54, wherein introducing the reagent mixture includes flowing the reagent mixture into the flow path and permitting the reagent mixture to diffuse into the sequestration pens.

56. The process of any one of embodiments 21 to 55, wherein the first (and/or the second) library of nucleic acid sequences is synthesized by a parallel nucleic acids synthesizer.

57. The process of embodiment 56, wherein the parallel nucleic acids synthesizer is a massively parallel nucleic acids synthesizer.

58 The process of embodiment 56 or 57, wherein the parallel nucleic acids synthesizer is configured to assemble a plurality of short-length synthesized nucleic acids into a longer conjoined nucleic acid.

59. The process of embodiment 58, wherein the parallel nucleic acids synthesizer configured to assemble longer conjoined nucleic acids is further configured to assemble a plurality of longer conjoined nucleic acids in parallel.

60. The process of any one of embodiment 22 to 59, wherein each of the second library of nucleic acid sequences is linked to a corresponding bead to form a second library of nucleic acid bearing beads.

61. The process of any one of embodiments 22 to 60, wherein the process of any one of embodiments 21 to 55 is repeated using the second library of nucleic acid sequences in place of the first library of nucleic acid sequences.

62. The process of embodiment 61, wherein a further library of nucleic acid sequences is designed and synthesized.

63. The process of embodiment 62, wherein the nucleic acid sequences of the further library of nucleic acid sequences are linked to corresponding beads to form a further library of nucleic acid bearing beads.

64. The process of embodiment 62 or 63, wherein the process of any one of embodiments 21 to 55 is performed using the further library of nucleic acid sequences in place of the first library of nucleic acid sequences.

65. The process of any one of embodiments 21 to 64, wherein the first library of nucleic acid sequences includes variations within a sub-region of the nucleic acid sequence encoding the protein of interest.

66. The process of embodiment 65, wherein the sub-region of the nucleic acid sequence encoding the protein of interest encodes for a region of the protein producing a function of interest.

67. The process of embodiment 66, wherein the sub-region encodes for an enzymatic active site or a binding site (e.g., an antigen recognition site or a protein-protein binding site) of the protein of interest.

68. The process of any one of embodiments 65 to 67, wherein the first library of nucleic acid sequences includes variations throughout the length of the nucleic acid sequence encoding the protein of interest.

69. The process of any one of embodiments 65 to 68, wherein the second library of nucleic acid sequences and/or the further library of nucleic acid sequences includes variations within a sub-region of the nucleic acid sequence encoding the protein of interest.

70. The process of embodiment 69, wherein the sub-region of the nucleic acid sequence encoding the protein of interest encodes for a region of the protein producing a function of interest.

71. The process of embodiment 70, wherein the sub-region encodes for an enzymatic active site or a binding site (e.g., an antigen recognition site or a protein-protein binding site) of the protein of interest.

72. The process of any one of embodiments 69 to 71, wherein the second library of nucleic acid sequences and/or the further library of nucleic acid sequences includes variations throughout the length of the nucleic acid sequence encoding the protein of interest.

73. A kit for rapid evolution of a protein of interest (e.g., an original protein sequence of interest, which may be a naturally occurring protein of interest or a non-naturally occurring protein, in either case optionally having a defined activity), the kit including: a microfluidic device, wherein the microfluidic device includes: a housing including a base and a microfluidic structure disposed on a surface of the base, wherein the base and the microfluidic structure define an interior chamber for holding a first liquid medium and micro-objects suspended therein; and a phenotypic reporter.

74. The kit of embodiment 73, wherein the phenotypic reporter includes a solution phase reagent providing a detectable signal when contacted by the protein of interest (e.g., the reagent could be cleaved by the protein of interest, and the cleavage could result in the emission of detectable light).

75. The kit of embodiment 73 or 74, wherein the phenotypic reporter includes: a plurality of micro-objects, each micro-object configured to provide a phenotypic readout from the protein sequence of interest.

76. The kit of embodiment 75, wherein the micro-objects of the plurality of micro-objects include binding sites for the protein of interest, include enzymatic substrates for an enzymatic activity of the original protein of interest, and/or are reporter cells configured to report a function of the protein of interest.

77. The kit of any one of embodiments 73 to 76, wherein the microfluidic structure of the microfluidic device includes: (i) a flow path for the first liquid medium; and (ii) a plurality of physical sequestration pens.

78. The kit of embodiment 77, wherein each sequestration pen of the plurality of sequestration pens includes: an enclosure; and a single opening to the flow path; wherein the enclosure encloses an interior space structured to hold a micro-object suspended in a second liquid medium.

79. The kit of embodiment 78, wherein the sequestration pen includes an inner wall extending from the opening into the enclosure.

80. The kit of any one of embodiments 73 to 79, wherein the opening of each sequestration pen of the plurality of sequestration pens of the microfluidic device is oriented such that no part is facing directly into the flow path of the channel, whereby, when the channel contains a flow of the first liquid medium and the sequestration pen contains the second liquid medium, a direct flow of the first liquid medium into the second liquid medium in the interior space is impeded while diffusive mixing of the first liquid medium with the second liquid medium in the interior space is allowed.

81. The kit of any one of embodiments 73 to 80, wherein the microfluidic device further includes a DEP configuration including: a first electrode; an electrode activation substrate; and a second electrode, wherein the first electrode is part of a first wall of the interior chamber and the electrode activation substrate and the second electrode are part of a second wall of the interior chamber, and wherein the electrode activation substrate comprises a photoconductive material, semiconductor integrated circuits, or phototransistors.

82. The kit of any one of embodiments 73 to 81, further including a reagent mixture for expressing protein from a nucleic acid sequence in vitro.

83. The kit of embodiment 82, wherein the reagent mixture is a cell free protein expression mixture.

84. The kit of any one of embodiments 73 to 83, wherein the kit further includes a plurality of beads, each configured to bind to a nucleic acid sequence.

85. The kit of embodiment 84, wherein each bead of the plurality of beads includes a unique barcode.

86. The kit of embodiment 85, wherein the unique barcode is a unique nucleic acid sequence.

87. The kit of any one of embodiments 73 to 86, wherein the kit further includes a plurality of protein aggregation beads.

88. The kit of embodiment 87, wherein each of the plurality of protein aggregation beads specifically bind an epitope of the original protein sequence of interest or a protein tag (e.g., an epitope tag).

89. The kit of any one of embodiments 73 to 88, further including machine readable instructions for a computer component or computer components.

90. The kit of embodiment 89, wherein the machine readable instructions enable the computer component or computer components to correlate individual nucleic acid sequences of a library of nucleic acid sequences with phenotypes associated with the individual nucleic acid sequences; and/or design a library of nucleic acid sequences, wherein each nucleic acid sequence of the library includes one or more variations from a nucleic acid sequence encoding an original protein sequence of interest and, optionally, wherein the library design is based upon a correlation between a plurality of individual nucleic acid sequences and phenotypes associated with the individual nucleic acid sequences.

What is claimed is:

1. A process for evolving a protein, the process comprising:
    disposing a first library of nucleic acid sequences within a microfluidic device, wherein the microfluidic device comprises: a housing comprising a base and a microfluidic structure disposed on a surface of the base, wherein the base and the microfluidic structure define a region for holding a first liquid medium and micro-objects suspended therein, and further wherein the microfluidic structure of the microfluidic device comprises a flow path for the first liquid medium and a plurality of chambers; wherein both the flow path and the plurality of chambers are fluidically interconnected with the region; and
    further wherein each nucleic acid sequence of the first library comprises one or more variations from a nucleic acid sequence encoding a protein sequence of interest;
    introducing a phenotypic reporter into the microfluidic device and disposing it in proximity to each nucleic acid sequence of the first library, wherein the phenotypic reporter comprises a solution phase reagent and/or a plurality of micro-objects, and is configured to provide a phenotypic readout from the protein sequence of interest;
    introducing a reagent mixture into the microfluidic device and disposing it in proximity to each nucleic acid sequence of the first library, wherein the reagent mixture is configured to express a corresponding protein sequence from each nucleic acid sequence of the first library;
    expressing the corresponding protein sequence from each nucleic acid sequence of the first library;
    detecting the phenotypic readout from a region proximal to one or more nucleic acid sequences of the first library;
    identifying individual nucleic acid sequences from the first library having a corresponding proximal region with a desired phenotypic readout; and
    determining the nucleotide sequence of the identified nucleic acid sequences of the first library.

2. The process of claim 1, further comprising:
    correlating the individual nucleic acid sequences of the first library with the phenotypic readout detected in the corresponding proximal regions; and
    designing a second library of nucleic acid sequences, wherein each nucleic acid sequence of the second library comprises one or more variations from the nucleic acid sequence encoding the protein sequence of interest, the one or more variations of each nucleic acid sequence of the second library selected in light of the correlation.

3. The process of claim 1, wherein each nucleic acid sequence of the first library is linked to a corresponding bead of a first plurality of beads.

4. The process of claim 1, wherein the process further comprises:
    designing the nucleic acid sequences of the first library to vary from the nucleic acid sequence encoding the protein sequence of interest;
    synthesizing the nucleic acid sequences of the first library; and
    connecting each nucleic acid sequence of the first library to a corresponding bead of a first plurality of beads, thereby forming a first library of nucleic acid bearing beads.

5. The process of claim 3, wherein each bead of the first plurality of beads further comprises a corresponding distinct barcode.

6. The process of claim 5, wherein the process further comprises reading the barcode of each bead of the first plurality of beads after disposing the first library of nucleic acid sequences in the microfluidic device, thereby identifying a location of each bead and its corresponding nucleic acid sequence within the microfluidic device.

7. The process of claim 1, wherein the process further comprises:
    disposing a plurality of protein aggregation beads within the microfluidic device and disposing one or more protein aggregation beads of the plurality in proximity to each nucleic acid sequence of the first library, wherein the protein aggregation beads of the plurality specifically bind to (i) an epitope of the protein sequence of interest or (ii) an epitope tag encoded by each nucleic acid sequence of the first library so as to be functionally comprised by the corresponding protein sequence expressed therefrom.

8. The process of claim 7, further comprising capturing the corresponding protein expressed from each nucleic acid sequence of the first library to the one or more protein aggregation beads disposed in proximity thereto.

9. The process of claim 8, wherein the process further comprises flowing a flushing medium through the microfluidic device after expressing the protein sequence, thereby displacing the reagent mixture, and wherein introducing the phenotypic reporter and disposing it in proximity to each nucleic acid of the first plurality is performed after flowing the flushing medium through the microfluidic device.

10. The process of claim 1, wherein introducing the phenotypic reporter and disposing it in proximity to each nucleic acid of the first plurality is performed after disposing the reagent mixture in proximity to each nucleic acid sequence of the first library.

11. The process of claim 1, wherein each chamber of the plurality comprises a sequestration pen.

12. The process of claim 11, wherein the sequestration pen comprises:
an enclosure; and
a single opening to the flow path;
wherein the enclosure encloses an interior space structured to hold a biological micro-object suspended in a second liquid medium.

13. The process of claim 10, wherein the microfluidic device further comprises a DEP configuration comprising:
a first electrode;
an electrode activation substrate; and
a second electrode,
wherein the first electrode is part of a first wall of the housing and the electrode activation substrate and the second electrode are part of a second wall of the housing, and wherein the electrode activation substrate comprises a photoconductive material, semiconductor integrated circuits, or phototransistors.

14. The process of claim 3, wherein disposing the first library of nucleic acid sequences within the microfluidic device comprises introducing individual beads of the first plurality of beads into each of the plurality of chambers.

15. The process of claim 1, wherein the protein sequence of interest comprises an enzyme or comprises a domain which binds to a cell surface marker.

16. The process of claim 1, wherein
the phenotypic reporter comprises a solution phase reagent providing a detectable signal when contacted by the protein sequence of interest; or
the phenotypic reporter comprises micro-objects comprising binding sites for the original protein sequence of interest, reporter cells configured to report a function of the original protein sequence of interest, or micro-objects providing enzymatic substrates for an enzymatic activity of the protein sequence of interest.

17. The process of claim 2, wherein correlating the individual nucleic acid sequences of the first library with the phenotypic readout detected in the corresponding proximal regions is performed by a first computer component configured to identify a function of the corresponding protein sequence expressed from the identified nucleic acid sequences that is more desirable than the function of the protein sequence of interest, wherein the first computer component employs a machine learning algorithm to perform the correlation.

18. The process of claim 17, wherein designing the second library of nucleic acid sequences is performed by a second computer component, based on the correlation of the expressed protein function with the nucleic acid sequences of the first library of nucleic acid sequences.

19. The process of claim 1, wherein the reagent mixture comprises a cell free protein expression reaction mixture.

20. The process of claim 2, wherein each of the second library of nucleic acid sequences is linked to a corresponding bead to form a second library of nucleic acid bearing beads.

21. The process of claim 1, wherein the first library of nucleic acid sequences comprises variations within a sub-region of the nucleic acid sequence encoding the protein sequence of interest, wherein the sub-region of the nucleic acid sequence encoding the protein sequence of interest encodes for a region of the protein producing a function of interest.

22. The process of claim 21, wherein the sub-region encodes for an enzymatic active site or a binding site of the original protein sequence of interest.

* * * * *